(12) United States Patent
Boehm et al.

(10) Patent No.: US 7,550,480 B2
(45) Date of Patent: Jun. 23, 2009

(54) COMPOUNDS

(75) Inventors: Jeffrey Charles Boehm, King of Prussia, PA (US); James Francis Callahan, King of Prussia, PA (US); Ralph F. Hall, King of Prussia, PA (US); Xichen Lin, King of Prussia, PA (US); Katherine Louise Widdowson, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 378 days.

(21) Appl. No.: 10/545,565

(22) PCT Filed: Feb. 13, 2004

(86) PCT No.: PCT/US2004/004406

§ 371 (c)(1),
(2), (4) Date: Aug. 12, 2005

(87) PCT Pub. No.: WO2004/073628

PCT Pub. Date: Sep. 2, 2004

(65) Prior Publication Data

US 2006/0211727 A1     Sep. 21, 2006

Related U.S. Application Data

(60) Provisional application No. 60/447,410, filed on Feb. 14, 2003, provisional application No. 60/538,095, filed on Jan. 21, 2004.

(51) Int. Cl.
*A01N 43/42* (2006.01)
*A61K 31/44* (2006.01)
*C07D 471/02* (2006.01)

(52) U.S. Cl. ...................... 514/300; 546/122

(58) Field of Classification Search ................. 546/122; 514/300
See application file for complete search history.

(56) References Cited

U.S. PATENT DOCUMENTS

| | | | |
|---|---|---|---|
| 3,843,663 A | | 10/1974 | Williams et al. |
| 3,962,262 A | * | 6/1976 | Williams et al. ............ 546/122 |
| 4,031,103 A | * | 6/1977 | Williams et al. ............ 546/122 |
| 4,560,691 A | | 12/1985 | Lesher et al. |
| 4,897,395 A | | 1/1990 | Duch et al. |
| 5,409,930 A | | 4/1995 | Spada et al. |
| 5,426,110 A | | 6/1995 | Gossett et al. |
| 5,547,954 A | | 8/1996 | Henrie, II et al. |
| 5,597,776 A | | 1/1997 | Bratz et al. |
| 5,620,981 A | | 4/1997 | Blankley et al. |
| 5,733,914 A | | 3/1998 | Blankley et al. |
| 5,817,670 A | | 10/1998 | Takayama et al. |
| 5,945,422 A | | 8/1999 | Doherty et al. |
| 5,989,588 A | | 11/1999 | Korn et al. |
| 6,200,977 B1 | | 3/2001 | Cushing et al. |
| 6,498,163 B1 | | 12/2002 | Boschelli et al. |
| 6,528,513 B2 | | 3/2003 | Cushing et al. |
| 6,809,199 B2 | | 10/2004 | Doherty et al. |
| 6,875,769 B2 | | 4/2005 | Chen |
| 2003/0092712 A1 | * | 5/2003 | Doherty et al. .......... 514/230.5 |
| 2003/0114671 A1 | | 6/2003 | Chen |

FOREIGN PATENT DOCUMENTS

| | | |
|---|---|---|
| EP | 0 168 037 | 1/1986 |
| EP | 0 278 686 | 5/1988 |
| JP | 1-261306 | 10/1989 |
| JP | 2003/127542 A | 5/2003 |
| WO | WO 02/058695 | 8/2002 |

OTHER PUBLICATIONS

Ferrarini et al., Farmaco (1998), 53(12), 741-746.*
Carboni et al., Gazzetta Chimica Italiana (1967), 97(8), 1262-73.*
Ferrarini et al., Journal of heterocyclic chemistry, 1984, 21(2), 417-19.*
Ferrarini et al., Annali di Chimica, 1971, 61(5), 318-25.*
Carboni et al., Gazzetta Chimica Italiana (1968), 98(10), 1174-88.*
Anderson et al., J. Org. Chem., vol. 42(6) pp. 993-996 (1977).
Baker et al., J. Heterocyclic Chem., 1964, vol. 1, pp. 263-270.
Carboni et al., *Gazzetta Chimica Italiana*, vol. 97(8) pp. 1262-1273 (1967).
Carboni et al., *Gazzetta Chimica Italiana*, vol. 98(10) pp. 1174-1188 (1968).
Ferrarini et al., *Journal of Heterocyclic Chemistry*, vol. 21(2) pp. 417-419 (1984).
Ferrarini et al., *Journal of Heterocyclic Chemistry*, vol. 34(5) pp. 1501-1510 (1997).
Hurlbert, et al., J. Med. Chem., 1968, vol. 11, pp. 703-707.
Rewcastle et al., Journal of Medicinal Chemistry, 1996 39(6), pp. 1823-1835.
Schoffstall et al., J. Org. Chem., 1971, 36(16), pp. 2385-2387.

(Continued)

*Primary Examiner*—D. Margaret Seaman
*Assistant Examiner*—Niloofar Rahmani
(74) *Attorney, Agent, or Firm*—Dara L. Dinner; Charles M. Kinzig

(57) ABSTRACT

Novel substituted 1,5,7-trisubstituted-1,8-napthyridin-2(1H)-one compounds; 1,5,7 trisubstituted-1,6-napthyridine-2-(1H)-one compounds and 1,5,7-trisubstituted quinoline-2(1H)-one compounds, processes for the preparation thereof, the use thereof in treating CSBP/p38 kinase mediated diseases and pharmaceutical compositions for use in such therapy.

21 Claims, 1 Drawing Sheet

OTHER PUBLICATIONS

Victory et al., J. Heterocycl. Chem, 1988, vol. 25, pp. 245-247.
Belled, et al., *Anales De Quimica*, vol. 86 (4) pp. 431-435 (1990).
Ferrarini et al., *Societa Chimica Italiana*, vol. 44 (6) pp. 579-584 (1989).
Ferrarini et al., *Societa Chimica Italiana*, vol. 53 (12) pp. 741-746 (1998).
Savarin, et al., *Organic Letters*, vol. 4 (12) pp. 2071-2074 (2002).
Singh, et al., *Am. Chem. Soc.*, vol. 35 (26) pp. 4858-4865 (1992).
Wenji Yin, et al., *Drug Metabolism and Disposition*, vol. 31 (2) pp. 215-223 (2003).

* cited by examiner

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Epidermal Growth Factor Receptor-Derived Peptide

<400> SEQUENCE: 1

Lys Arg Glu Leu Val Glu Pro Leu Thr Pro Ser Gly Glu Ala Pro Asn
1               5                   10                  15

Gln Ala Leu Leu Arg
            20

COMPOUNDS

This application is the §371 national stage entry of PCT/US2004004406, filed 14 Feb. 2004 and which claims the benefit of U.S. Provisional Applications U.S. Ser. No. 60/447,410, filed 14 Feb. 2003, and U.S. Ser. No. 60/538,095 filed 21 Jan. 2004.

FIELD OF THE INVENTION

This invention relates to a novel group of 1,5,7-trisubstituted-1,8-napthyridin-2(1H)-one compounds; 1,5,7 trisubstituted-1,6-napthyridine-2-(1H)-one compounds and 1,5,7-trisubstituted quinoline-2(1H)-one compounds, processes for the preparation thereof, the use thereof in treating CSBP/p38 kinase mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phopholipases are the essential machinery by which the signal is further transmitted within the cell [Marshall, J. C. Cell, 80, 179-278 (1995)]. Protein kinases can be categorized into five classes with the two major classes being, tyrosine kinases and serine/threonine kinases depending upon whether the enzyme phosphorylates its substrate(s) on specific tyrosine(s) or serine/threonine(s) residues [Hunter, T., Methods in Enzymology (Protein Kinase Classification) p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. Cell, 80, 179 (1995); Herskowitz, I. Cell, 80, 187 (1995); Hunter, T. Cell, 80, 225 (1995); Seger, R., and Krebs, E. G. FASEB J., 726-735 (1995)].

While many signaling pathways are part of cell homeostasis, numerous cytokines (e.g., IL-1 and TNF) and certain other mediators of inflammation (e.g., COX-2, and iNOS) are produced only as a response to stress signals such as bacterial lipopolysaccharide (LPS). The first indications suggesting that the signal transduction pathway leading to LPS-induced cytokine biosynthesis involved protein kinases came from studies of Weinstein [Weinstein, et al., J. Immunol. 151, 3829 (1993)] but the specific protein kinases involved were not identified. Working from a similar perspective, Han [Han, et al., Science 265, 808 (1994)] identified murine p38 as a kinase which is tyrosine phosphorylated in response to LPS. Definitive proof of the involvement of the p38 kinase in LPS-stimulated signal transduction pathway leading to the initiation of proinflammatory cytokine biosynthesis was provided by the independent discovery of p38 kinase by Lee [Lee; et al., Nature, 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in the low uM range [Lee, et al., Int. J. Immunopharmac. 10(7), 835(1988)] and exhibited activity in animal models which are refractory to cyclooxygenase inhibitors [Lee; et al., Annals N.Y. Acad. Sci., 696, 149(1993)].

It is now firmly established that CSBP/p38 is a one of several kinases involved in a stress-response signal transduction pathway, which is parallel to and largely independent of the analogous mitogen-activated protein kinase (MAP) kinase cascade. Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 1). Additional downstream substrates known to be phosphorylated by p38 include kinases (Mnk1/2, MSK1/2 and PRAK) and transcription factors (CHOP, MEF2, ATF2 and CREB). While many of the signaling pathways required for cytokine biosynthesis remain unknown it appears clear that many of the substrates for p38 listed above are involved. [Cohen, P. Trends Cell Biol., 353-361(1997) and Lee, J. C. et al, Pharmacol. Ther. vol. 82, nos. 2-3, pp. 389-397, 1999].

What is known, however, is that in addition to inhibiting IL-1 and TNF, CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. Trends Cell Biol., 353-361(1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Evidence also links IL-1 activity to diabetes and pancreatic β cells [review of the biological activities which have been attributed to IL-1 Dinarello, J. Clinical Immunology, 5 (5), 287-297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcososis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

In addition to the involvement of CSBP/p38 signaling in the production of IL-1, TNF, IL-8, IL-6, GM-CSF, COX-2, collagenase and stromelysin, signal transduction via CSBP/p38 is required for the action of several of these same pro-inflammatory proteins plus many others (VEGF, PDGF, NGF) [Ono, K. and Han, J., Cellular Signalling, 12 1-13 (2000)]. The involvement of CSBP/p38 in multiple stress-induced signal transduction pathways provides additional rationale for the potential utility of CSBP/p38 in the treatment of diseases resulting from the excessive and destructive activation of the immune system. This expectation is supported by the potent and diverse activities described for CSBP/p38 kinase inhibitors [Badger, et al., *J. Pharm. Exp. Thera.* 279 (3): 1453-1461.(1996); Griswold, et al, *Pharmacol. Comm.* 7, 323-229 (1996); Jackson, et al., J. Pharmacol. Exp. Ther. 284, 687-692 (1998); Underwood, et al., J. Pharmacol. Exp. Ther. 293, 281-288 (2000); Badger, et al., Arthritis Rheum. 43, 175-183 (2000)].

There remains a need for treatment, in this field, for compounds which are cytokine suppressive anti-inflammatory drugs, i.e. compounds which are capable of inhibiting the CSBP/p38/RK kinase.

Other containing pharmacophores having varying pharmaceutical, insecticidal, and herbicidal activity may be found in the art, such as in WO 98/33798; WO 98/23613; WO 95/19774, now U.S. Pat. No. 6,265,410; WO 00/23444; WO 01/19828; U.S. Pat. No. 5,532,370; U.S. Pat. No. 5,597,776; JP 2000-38350; WO 00/43374; WO 98/08846; WO 01/55147, WO 01/64679, WO 01/38312, WO 01/37837 and WO 02/059083.

SUMMARY OF THE INVENTION

Figure 1:
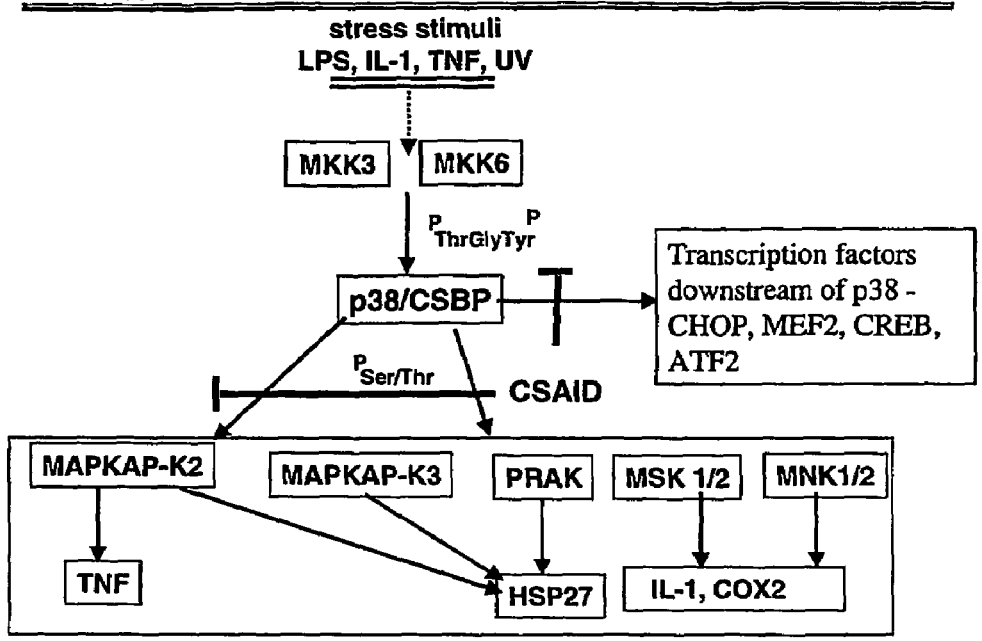
FIG. 1 demonstrates the p38 kinase cascade.

This invention relates to the novel compounds of Formula (I) and (Ia), and pharmaceutical compositions comprising a compound of Formula (I) and (Ia), and a pharmaceutically acceptable diluent or carrier.

This invention relates to a method of treating a CSBP/RK/p38 kinase mediated disease in a mammal in need thereof, which comprises administering to said mammal an effective amount of a compound of Formula (I) and (Ia).

This invention also relates to a method of inhibiting cytokines and the treatment of a cytokine mediated disease, in a mammal in need thereof, which comprises administering to said mammal an effective amount of a compound of Formula (I) and (Ia).

This invention more specifically relates to a method of inhibiting the production of IL-1 in a mammal in need thereof which comprises administering to said mammal an effective amount of a compound of Formula (I) and (Ia).

This invention more specifically relates to a method of inhibiting the production of IL-6 in a mammal in need thereof which comprises administering to said mammal an effective amount of a compound of Formula (I) and (Ia).

This invention more specifically relates to a method of inhibiting the production of IL-8 in a mammal in need thereof which comprises administering to said mammal an effective amount of a compound of Formula (I) and (Ia).

This invention more specifically relates to a method of inhibiting the production of TNF in a mammal in need thereof which comprises administering to said mammal an effective amount of a compound of Formula (I) and (Ia).

Accordingly, the present invention provides a compound of Formula (I) and (Ia):

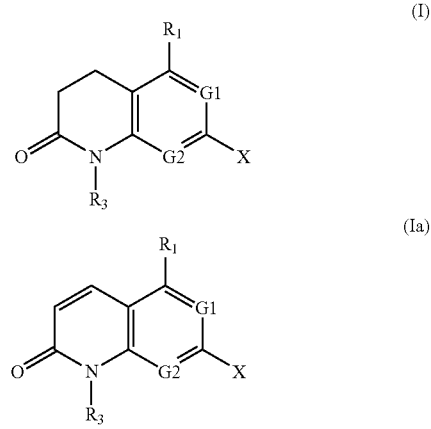

wherein $R_1$ is an optionally substituted aryl or an optionally substituted heteroaryl ring;

X is halogen, $R_2$, $OR_2$, $S(O)_m R_2$, $(CH_2)_n N(R_{10})S(O)_m R_2$, $(CH_2)_n N(R_{10})C(O)R_2$, $(CH_2)_n NR_4 R_{14}$, $NR_2(CH_2)_n NR_4 R_{14}$, $O(CH_2)_n NR_4 R_{14}$, $S(CH_2)_n NR_4 R_{14}$, $(CH_2)_n J$, $NR_2(CH_2)_n J$, $O(CH_2)_n J$, $S(CH_2)_n J$, or $(CH_2)_n N(R_2)_2$;

J is an optionally substituted heteroaryl ring;

n is 0 or an integer having a value of 1 to 10;

m is 0 or an integer having a value of 1 or 2;

q is 0 or an integer having a value of 1 to 10;

$R_2$ is hydrogen, $C_{1-10}$ alkyl, aryl, aryl$C_{1-10}$ alkyl, heteroaryl, heteroaryl$C_{1-10}$ alkyl, which moieties are all optionally substituted, or $R_2$ is the moiety $X_1(CR_{10}R_{20})_q C(A_1)(A_2)(A_3)$, or $C(A_1)(A_2)(A_3)$;

$X_1$ is $N(R_{10})$, O, $S(O)_m$, or $CR_{10}R_{20}$;

$X_2$ is independently hydrogen, halogen or $C_{1-4}$ alkyl;

$A_1$ is an optionally substituted $C_{1-10}$ alkyl;

$A_2$ is an optionally substituted $C_{1-10}$ alkyl;

$A_3$ is hydrogen or is an optionally substituted $C_{1-10}$ alkyl;

$G_1$ and $G_2$ are independently selected from is N, or C—$X_2$, provided that $G_1$ and $G_2$ are not both nitrogen;

$R_3$ is a hydrogen, $C_{1-10}$ alkyl, $C_{3-7}$ cycloalkyl, $C_{3-7}$ cycloalkyl$C_{1-4}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are optionally substituted; provided that $R_3$ is not hydrogen or methyl when $G_1$ is nitrogen, $G_2$ is C—$X_2$, $X_2$ is hydrogen, $R_1$ is an optionally substituted phenyl, X is $R_2$ and $R_2$ is hydrogen;

$R_4$ and $R_{14}$ are each independently selected from hydrogen, optionally substituted $C_{1-4}$ alkyl, optionally substituted aryl, or optionally substituted aryl-$C_{1-4}$ alkyl, aryl$C_{1-10}$ alkyl, heteroaryl or heteroaryl$C_{1-10}$ alkyl, wherein each of these moieties may be optionally substituted;

$R_{10}$ and $R_{20}$ are independently selected from hydrogen or $C_{1-4}$alkyl; or a pharmaceutically acceptable salt thereof.

DETAILED DESCRIPTION OF THE INVENTION

The present invention is directed to novel compounds of Formula (I) and (Ia), or a pharmaceutically acceptable salt thereof.

Suitably, for compounds of Formula (I), and (Ia), $R_1$ is an aryl, or heteroaryl ring, which ring is optionally substituted. The $R_1$ aryl or heteroaryl rings may be substituted one or more times, preferably 1 to 4 times, independently, by substituents selected from halogen, $C_{1-4}$ alkyl, halo-substituted-$C_{1-4}$ alkyl, cyano, nitro, $(CR_{10}R_{20})_v NR_4R_{14}$, $(CR_{10}R_{20})_v C(Z)NR_4R_{14}$, $(CR_{10}R_{20})_v C(Z)OR_8$, $(CR_{10}R_{20})_v COR_{a'}$, $(CR_{10}R_{20})_v C(O)H$, $SR_5$, $S(O)R_5$, $S(O)_2R_5$, $(CR_{10}R_{20})_v OR_8$, $ZC(Z)R_{11}$, $NR_{10}C(Z)R_{11}$, or $NR_{10}S(O)_2R_7$.

Suitably, when $R_1$ is an aryl moiety, such as a phenyl ring, the ring is optionally substituted one or more times by halogen, $C_{1-4}$ alkyl, or halo-substituted-$C_{1-4}$ alkyl. In one embodiment the phenyl ring is substituted in the 2, 4, or 6-position, or di-substituted in the 2,4-position, such as 2-fluoro, 2-chloro, 4-fluoro, 4-chloro, 2,4-difluoro, 2-methyl-4-chloro, or 2-methyl-4-fluoro; or tri-substituted in the 2,4,6-position such as 2,4,6-trifluoro. Another embodiment of the invention is the substitution of the phenyl ring in the 3-position, such as with a halogen derivative, producing a 3-position, 2,3-disubstitution, or a 3,4-disubstitution.

Suitably, when $R_1$ is a heteroaryl moiety, the ring is not attached to the pharmacophore via one of the heteroatoms, such as nitrogen to form a charged ring. For instance, a pyridinyl ring would be attached through a carbon atom to yield a 2-, 3- or 4-pyridyl moiety, which is optionally substituted.

Suitably, v is 0 or an integer having a value of 1 or 2.

Suitably, Z is oxygen or sulfur.

Suitably, $R_{a'}$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_v OR_7$, $(CR_{10}R_{20})_v S(O)_m R_7$, $(CR_{10}R_{20})_v NR_{10}S(O)_2R_7$, or $(CR_{10}R_{20})_v NR_4R_{14}$; and wherein the aryl, arylalkyl, heteroaryl, heteroaryl alkyl may be optionally substituted.

Suitably, $R_4$ and $R_{14}$ are each independently selected from hydrogen, optionally substituted $C_{1-4}$ alkyl, optionally substituted aryl, optionally substituted aryl-$C_{1-4}$ alkyl, optionally substituted heteroaryl, optionally substituted heteroaryl-$C_{1-4}$ alkyl.

The $R_4$ and $R_{14}$ moieties may be optionally substituted, one or more times, preferably 1 to 4 times independently by halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; S(O)m alkyl, such as methyl thio, methylsulfinyl or methyl sulfonyl; aldehydes (—C(O)), or a ketone, such as —C(O)$R_6$, such as C(O)$C_{1-10}$alkyl or C(O)aryl; amides, such as C(O)NR$_{4'}$R$_{14'}$, or NR$_{4'}$C(O)$C_{1-10}$alkyl, or NR$_{4'}$C(O)aryl; NR$_{4'}$R$_{14'}$, wherein R$_{4'}$ and R$_{14'}$ are each independently hydrogen or $C_{1-4}$ alkyl, or wherein the R$_{4'}$R$_{14'}$ can cyclize together with the nitrogen to which they are attached to form a 5 to 7 membered ring which optionally contains an additional heteroatom selected from O/N/S; cyano, nitro, $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such $CF_2CF_2H$, $CH_2CF_3$, or $CF_3$; an optionally substituted aryl, such as phenyl, or an optionally substituted arylalkyl, such as benzyl or phenethyl, wherein these aryl containing moieties may themselves also be substituted one to two times by halogen; hydroxy; hydroxy substituted alkyl; $C_{1-10}$ alkoxy; $S(O)_m$alkyl; amino, mono & di-substituted $C_{1-4}$ alkyl amino; $C_{1-4}$ alkyl, or $CF_3$.

Suitably, $R_5$ is hydrogen, $C_{1-4}$ alkyl, $C_{2-4}$ alkenyl, $C_{2-4}$ alkynyl or $NR_4R_{14}$, excluding the moieties $SR_5$ being $SNR_4R_{14}$, $S(O)_2R_5$ being $SO_2H$ and $S(O)R_5$ being SOH.

Suitably, $R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein these moieties may be optionally substituted.

Suitably, $R_7$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl; and wherein each of these moieties may be optionally substituted.

Suitably, $R_8$ is hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_t OR_7$, $(CR_{10}R_{20})_t S(O)_m R_7$, $(CR_{10}R_{20})_t NR_{10}S(O)_2R_7$, or $(CR_{10}R_{20})_t NR_4R_{14}$; and wherein the cycloalkyl, cycloalkenyl, aryl, arylalkyl, heteroaryl, heteroaryl alkyl, heterocyclic and heterocyclic alkyl moieties may be optionally substituted.

Suitably, t is an integer having a value of 1 to 3.

Suitably, $R_9$ is hydrogen, $C(Z)R_6$, optionally substituted $C_{1-10}$ alkyl, optionally substituted aryl or optionally substituted aryl-$C_{1-4}$ alkyl.

Suitably, $R_{10}$ and $R_{20}$ are independently selected from hydrogen or a $C_{1-4}$ alkyl.

Suitably, $R_{11}$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_t OR_7$, $(CR_{10}R_{20})_t S(O)_m R_7$, $(CR_{10}R_{20})_t NR_{10}S(O)_2R_7$, or $(CR_{10}R_{20})_v NR_4R_{14}$; and wherein the aryl, arylalkyl, heteroaryl, heteroaryl alkyl, heterocyclyl, and heterocyclylalkyl moieties may be optionally substituted.

Suitably m is 0 or an integer having a value of 1 or 2.

Suitably, $R_3$ is an optionally substituted $C_{1-10}$ alkyl, $C_{3-7}$ cycloalkyl, $C_{3-7}$ cycloalkyl$C_{1-10}$alkyl, aryl, aryl$C_{1-10}$ alkyl, heteroarylC$_{1-10}$alkyl, or heterocyclylC$_{1-10}$ alkyl moiety, which moieties are optionally substituted. The moieties may be optionally substituted one or more times, suitably 1 to 4 times, independently by C$_{1-10}$ alkyl, halo-substituted C$_{1-10}$ alkyl, C$_{2-10}$ alkenyl, C$_{2-10}$alkynyl, C$_{3-7}$cycloalkyl, C$_{3-7}$cycloalkylC$_{1-10}$ alkyl, C$_{5-7}$cycloalkenyl, C$_{5-7}$cycloalkenylC$_{1-10}$ alkyl, halogen, cyano, nitro, (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$NR$_{10}$S(O)$_2$R$_7$, (CR$_{10}$R$_{20}$)$_n$NR$_4$R$_{14}$, (CR$_{10}$R$_{20}$)$_n$CN, (CR$_{10}$R$_{20}$)$_n$S(O)$_2$NR$_4$R$_{14}$, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$C(Z)NR$_4$R$_{14}$, (CR$_{10}$R$_{20}$)$_n$NR$_{10}$C(Z)R$_6$, (CR$_{10}$R$_{20}$)$_n$NR$_{10}$C(=NR$_{10}$)NR$_4$R$_{14}$, (CR$_{10}$R$_{20}$)$_n$OC(Z)NR$_4$R$_{14}$, (CR$_{10}$R$_{20}$)$_n$NR$_{10}$C(Z)NR$_4$R$_{14}$, or (CR$_{10}$R$_{20}$)$_n$NR$_{10}$C(Z)OR$_7$.

In one embodiment, the optional substituents on the R$_3$ moieties are independently selected from halogen, alkyl, hydroxy, alkoxy, cyano, nitro, amino, or halosubstituted alkyl, suitably halogen, or alkyl.

Yet in another embodiment, R$_3$ is an optionally substituted C$_{1-10}$ alkyl, C$_{3-7}$cycloalkyl, C$_{3-7}$cycloalkylalkyl, aryl, or aryl C$_{1-10}$ alkyl; in another embodiment R$_3$ is an optionally substituted C$_{1-10}$ alkyl, aryl, or aryl C$_{1-10}$ alkyl.

Suitably, when the R$_3$ moiety is an aryl ring, it is an optionally substituted phenyl ring. The ring may be optionally substituted one or more times by halogen, C$_{1-4}$ alkyl, or halosubstituted-C$_{1-4}$ alkyl. More preferably, the phenyl ring is substituted in the 2, 4, or 6-position, or di-substituted in the 2,4-position, such as 2-fluoro, 2-chloro, 4-fluoro, 4-chloro, 2,4-difluoro, 2-methyl-4-chloro, or 2-methyl-4-fluoro; or trisubstituted in the 2,4,6-position, such as 2,4,6-trifluoro.

Suitably, n is 0, or an integer having a value of 1 to 10.

Suitably, X is R$_2$, OR$_2$, S(O)$_m$R$_2$, (CH$_2$)$_n$N(R$_{10}$)S(O)$_m$R$_2$, (CH$_2$)$_n$N(R$_{10}$)C(O)R$_2$, (CH$_2$)$_n$NR$_4$R$_{14}$, NR$_2$(CH$_2$)$_n$NR$_4$R$_{14}$, O(CH$_2$)$_n$NR$_4$R$_{14}$, S(CH$_2$)nNR$_4$R$_{14}$, (CH$_2$)$_n$J, NR$_2$(CH$_2$)$_n$J, O(CH$_2$)$_n$J, S(CH$_2$)$_n$J, or (CH$_2$)$_n$N(R$_2$)$_2$. In another embodiment when X is R$_2$, then R$_2$ is the moiety X$_1$(CR$_{10}$R$_{20}$)$_q$C(A$_1$)(A$_2$)(A$_3$), or C(A$_1$)(A$_2$)(A$_3$).

Suitably, J is a heteroaryl ring, optionally substituted one or more times, suitably 1 to 3 times, as defined herein.

Suitably, R$_2$ is independently selected from hydrogen, halogen, optionally substituted C$_{1-10}$ alkyl, optionally substituted aryl, optionally substituted arylC$_{1-10}$alkyl, optionally substituted heteroaryl, optionally substituted heteroarylC$_{1-10}$ alkyl, or R$_2$ is the moiety X$_1$(CR$_{10}$R$_{20}$)$_q$C(A$_1$)(A$_2$)(A$_3$), or C(A$_1$)(A$_2$)(A$_3$).

The R$_2$ moieties, excluding hydrogen, may be optionally substituted one or more times, preferably 1 to 4 times, independently by C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$ alkyl C$_{5-7}$cycloalkenyl, C$_{5-7}$ cycloalkenyl C$_{1-10}$ alkyl, halogen, —C(O), cyano, nitro, (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$NR$_{10}$S(O)$_2$R$_7$, (CR$_{10}$R$_{20}$)$_n$NR$_4$R$_{14}$, (CR$_{10}$R$_{20}$)$_n$CN, (CR$_{10}$R$_{20}$)$_n$S(O)$_2$NR$_4$R$_{14}$, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$C(Z)NR$_4$R$_{14}$, (CR$_{10}$R$_{20}$)$_n$NR$_{10}$C(Z)R$_6$, (CR$_{10}$R$_{20}$)$_n$NR$_{10}$C(=NR$_{10}$)NR$_4$R$_{14}$, (CR$_{10}$R$_{20}$)$_n$C(=NOR$_6$)NR$_4$R$_{14}$, (CR$_{10}$R$_{20}$)$_n$OC(Z)NR$_4$R$_{14}$, (CR$_{10}$R$_{20}$)$_n$NR$_{10}$C(Z)NR$_4$R$_{14}$, or (CR$_{10}$R$_{20}$)$_n$NR$_{10}$C(Z)OR$_7$.

In another embodiment X is R$_2$, and R$_2$ is OR$_2$, (CH$_2$)$_n$N(R$_2$)$_2$ or (CH$_2$)$_n$NR$_4$R$_{14}$ or R$_2$ is the moiety X$_1$(CR$_{10}$R$_{20}$)$_q$C(A$_1$)(A$_2$)(A$_3$). Suitably when X is (CH$_2$)$_n$N(R$_2$)$_2$, R$_2$ is (CR$_{10}$R$_{20}$)$_n$NR$_4$R$_{14}$ or (CR$_{10}$R$_{20}$)$_n$NR$_{10}$C(Z)R$_6$.

Suitably X$_1$ is N(R$_{10}$), O, S(O)$_m$, or CR$_{10}$R$_{20}$. Preferably, X$_1$ is N(R$_{10}$), or oxygen.

Suitably, q is 0 or an integer having a value of 1 to 10.

Suitably, A$_1$ is an optionally substituted C$_{1-10}$ alkyl.

Suitably, A$_2$ is an optionally substituted C$_{1-10}$ alkyl.

Suitably, A$_3$ is hydrogen or is an optionally substituted C$_{1-10}$ alkyl.

The A$_1$, A$_2$, and A$_3$ C$_{1-10}$ alkyl moieties may optionally substituted, independently, one or more times, suitably from 1 to 4 times, by halogen, such as chlorine, fluorine, bromine, or iodine; halo-substituted C$_{1-10}$alkyl, such as CF$_3$, or CHF$_2$CF$_3$; C$_{2-10}$ alkenyl, C$_{2-10}$ alkynyl, C$_{3-7}$ cycloalkyl, C$_{3-7}$cycloalkylC$_{1-10}$alkyl, C$_{5-7}$cycloalkenyl, C$_{5-7}$ cycloalkenylC$_{1-10}$alkyl, (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$NR$_{10}$S(O)$_2$R$_7$, (CR$_{10}$R$_{20}$)$_n$NR$_4$R$_{14}$, (CR$_{10}$R$_{20}$)$_n$CN, (CR$_{10}$R$_{20}$)$_n$S(O)$_2$NR$_4$R$_{14}$, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$C(Z)NR$_4$R$_{14}$, (CR$_{10}$R$_{20}$)$_n$NR$_{10}$C(Z)R$_6$, (CR$_{10}$R$_{20}$)$_n$NR$_{10}$C(=NR$_{10}$)NR$_4$R$_{14}$, (CR$_{10}$R$_{20}$)$_n$OC(Z)NR$_4$R$_{14}$, (CR$_{10}$R$_{20}$)$_n$NR$_{10}$C(Z)NR$_4$R$_{14}$, or (CR$_{10}$R$_{20}$)$_n$NR$_{10}$C(Z)OR$_7$.

Suitably, one or more of A$_1$ to A$_3$ substituents is substituted with (CR$_{10}$R$_{20}$)$_n$OR$_6$; and R$_6$ is suitably hydrogen.

In another embodiment the C(A$_1$)(A$_2$)(A$_3$) group is CH(CH$_2$OH)$_2$, or C(CH$_3$)(CH$_2$OH)$_2$, X$_1$(CR$_{10}$R$_{20}$)$_q$CH(CH$_2$OH)$_2$, or X$_1$(CR$_{10}$R$_{20}$)$_q$C(CH$_3$)(CH$_2$OH)$_2$; and X$_1$ is suitably oxygen or nitrogen.

Suitably, G$_1$ and G$_2$ are independently selected from is N, or C—X$_2$, provided that G$_1$ and G$_2$ are not both nitrogen.

X$_2$ is independently selected from hydrogen, halogen, or C$_{1-4}$alkyl.

Compounds of Formula (I) and (Ia) wherein G$_1$ is CH or C(C$_{1-4}$alkyl), and G$_2$ is nitrogen, are respectively designated as 1,5,7-trisubstituted-1,8-napthyridin-2(1H)-one compounds, and are also referred to herein as compounds of Formula (II) and (IIa).

Accordingly compounds of Formula (II) and (IIa) are represented by the structure:

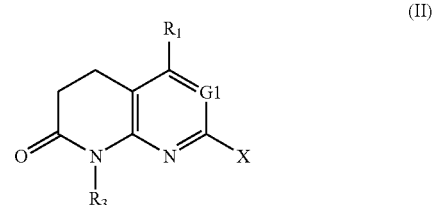

(II)

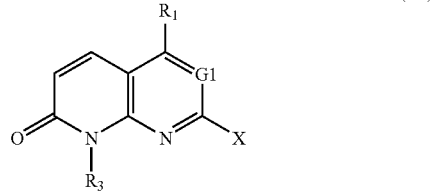

(IIa)

wherein
R$_1$ is an optionally substituted aryl or an optionally substituted heteroaryl ring;
X is R$_2$, OR$_2$, S(O)$_m$R$_2$, (CH$_2$)$_n$N(R$_{10}$)S(O)$_m$R$_2$, (CH$_2$)$_n$N(R$_{10}$)C(O)R$_2$, (CH$_2$)$_n$NR$_4$R$_{14}$, NR$_2$(CH$_2$)$_n$NR$_4$R$_{14}$, O(CH$_2$)$_n$NR$_4$R$_{14}$, S(CH$_2$)$_n$NR$_4$R$_{14}$, (CH$_2$)$_n$J, NR$_2$(CH$_2$)$_n$J, O(CH$_2$)$_n$J, S(CH$_2$)$_n$J, or (CH$_2$)$_n$N(R$_2$)$_2$;
J is an optionally substituted heteroaryl ring;
n is 0 or an integer having a value of 1 to 10;
m is 0 or an integer having a value of 1 or 2;
q is 0 or an integer having a value of 1 to 10;
R$_2$ is hydrogen, C$_{1-10}$ alkyl, aryl, arylC$_{1-10}$ alkyl, heteroaryl, heteroarylC$_{1-10}$ alkyl which moieties are all optionally substituted, or R$_2$ is the moiety X$_1$(CR$_{10}$R$_{20}$)$_q$C(A$_1$)(A$_2$)(A$_3$), or C(A$_1$)(A$_2$)(A$_3$);

$X_1$ is $N(R_{10})$, O, $S(O)_m$, or $CR_{10}R_{20}$;
$X_2$ is independently hydrogen, halogen or $C_{1-4}$ alkyl;
$A_1$ is an optionally substituted $C_{1-10}$ alkyl;
$A_2$ is an optionally substituted $C_{1-10}$ alkyl;
$A_3$ is hydrogen or is an optionally substituted $C_{1-10}$ alkyl;
$G_1$ is C—$X_2$;
$R_3$ is a hydrogen, $C_{1-10}$ alkyl, $C_{3-7}$ cycloalkyl, $C_{3-7}$ cycloalkyl$C_{1-4}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are optionally substituted; provided that $R_3$ is not hydrogen or methyl when $G_1$ is nitrogen, $G_2$ is C—$X_2$, $X_2$ is hydrogen, $R_1$ is an optionally substituted phenyl, X is $R_2$ and $R_2$ is hydrogen;
$R_4$ and $R_{14}$ are each independently selected from hydrogen, optionally substituted $C_{1-4}$ alkyl, optionally substituted aryl, or optionally substituted aryl-$C_{1-4}$ alkyl, aryl$C_{1-10}$ alkyl, heteroaryl or heteroaryl$C_{1-10}$ alkyl, wherein each of these moieties may be optionally substituted;
$R_{10}$ and $R_{20}$ are independently selected from hydrogen or $C_{1-4}$alkyl; or a pharmaceutically acceptable salt thereof.

Suitably, in another embodiment of the invention, when X is $R_2$, then $R_2$ is $C_{3-7}$ cycloalkyl, $C_{3-7}$ cycloalkyl$C_{1-4}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, or $R_2$ is the moiety $X_1(CR_{10}R_{20})_q$—$C(A_1)(A_2)(A_3)$, or $C(A_1)(A_2)(A_3)$.

Representative species of Formula (II) and (IIa) are:
1,5-bis(4-fluorophenyl)[1,8]naphthyridin-2(1H)-oneX; and
5-(2,4-difluorophenyl)-1-(4-fluorophenyl)[1,8]naphthyridin-2(1H)-one,
1,5-bis(2-chlorophenyl)-7-{[2-(isopropylamino)ethyl]amino}[1,8]naphthyridin-2(1H-one;
1,5-bis(2-chlorophenyl)-7-{[2-hydroxy-1-(hydroxymethyl)ethyl]amino}[1,8]naphthyridin-2(1H-one;

or a pharmaceutically acceptable salt thereof.

Compounds of Formula (I) and (Ia) wherein $G_2$ is CH or $C(C_{1-4}alkyl)$, and $G_1$ is nitrogen are respectively designated as 1,5,7 trisubstituted-1,6-napthyridine-2-(1H)-one compounds and are also referred to herein as compounds of Formula (III) and (IIIa).

Accordingly compounds of Formula (III) and (IIIa) are represented by the structure:

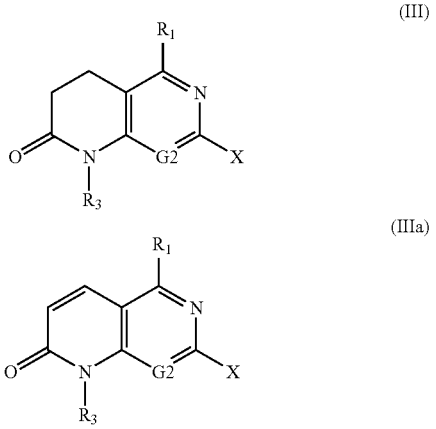

wherein
$R_1$ is an optionally substituted aryl or an optionally substituted heteroaryl ring;

X is $R_2$, $OR_2$, $S(O)_mR_2$, $(CH_2)_nN(R_{10})S(O)_mR_2$, $(CH_2)_nN(R_{10})C(O)R_2$, $(CH_2)_nNR_4R_{14}$, $NR_2(CH_2)_nNR_4R_{14}$, $O(CH_2)_nNR_4R_{14}$, $S(CH_2)_nNR_4R_{14}$, $(CH_2)_nJ$, $NR_2(CH_2)_nJ$, $O(CH_2)_nJ$, $S(CH_2)_nJ$, or $(CH_2)_nN(R_2)_2$;
J is an optionally substituted heteroaryl ring;
n is 0 or an integer having a value of 1 to 10;
m is 0 or an integer having a value of 1 or 2;
q is 0 or an integer having a value of 1 to 10;
$R_2$ is hydrogen, $C_{1-10}$ alkyl, aryl, aryl$C_{1-10}$ alkyl, heteroaryl, heteroaryl$C_{1-10}$ alkyl, which moieties are all optionally substituted, or $R_2$ is the moiety $X_1(CR_{10}R_{20})_qC(A_1)(A_2)(A_3)$, or $C(A_1)(A_2)(A_3)$;
$X_1$ is $N(R_{10})$, O, $S(O)_m$, or $CR_{10}R_{20}$;
$X_2$ is independently hydrogen, halogen or $C_{1-4}$ alkyl;
$A_1$ is an optionally substituted $C_{1-10}$ alkyl;
$A_2$ is an optionally substituted $C_{1-10}$ alkyl;
$A_3$ is hydrogen or is an optionally substituted $C_{1-10}$ alkyl;
$G_2$ is C—$X_2$;
$R_3$ is a hydrogen, $C_{1-10}$ alkyl, $C_{3-7}$ cycloalkyl, $C_{3-7}$ cycloalkyl$C_{1-4}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are optionally substituted; provided that $R_3$ is not hydrogen or methyl when $G_1$ is nitrogen, $G_2$ is C—$X_2$, $X_2$ is hydrogen, $R_1$ is an optionally substituted phenyl, X is $R_2$ and $R_2$ is hydrogen;
$R_4$ and $R_{14}$ are each independently selected from hydrogen, optionally substituted $C_{1-4}$ alkyl, optionally substituted aryl, or optionally substituted aryl-$C_{1-4}$ alkyl, aryl$C_{1-10}$ alkyl, heteroaryl or heteroaryl$C_{1-10}$ alkyl, wherein each of these moieties may be optionally substituted;
$R_{10}$ and $R_{20}$ are independently selected from hydrogen or $C_{1-4}$alkyl; or a pharmaceutically acceptable salt thereof.

Representative species of Formula (III) and (IIa) are:
7-Bromo-1,5-bis(2-chlorophenyl)-3,4-dihydro[1,6]naphthyridin-2(1H)-one;
7-Bromo-1,5-bis(2-chlorophenyl)[1,6]naphthyridin-2(1H)-one;
1,5-Bis(2-Chlorophenyl)-7-[(2-hydroxy-1-(hydroxymethyl)ethyl]-amino]-[1,6]naphthyridin-2(1H)-one;
N-[2-[[1,5-bis(2-Chlorophenyl)-2-oxo-1,2-dihydro[1,6]naphthyridin-7-yl]amino]ethyl]acetamide;
1,5-Bis(2-Chlorophenyl)-7-[(1H-imidazol-2-ylmethyl)amino][1,6]naphthyridin-2(1H)-one;
1,5-Bis(2-Chlorophenyl)-7-[[2-(Isopropylamino)ethyl]amino][1,6]naphthyridin-2(1H)-one;
1,5-Bis(2-Chlorophenyl)-7-amino-[1,6]naphthyridin-2(1H)-one;
1,5-Bis(2-Chlorophenyl)-7-chloro-[1,6]naphthyridin-2(1H)-one;

or a pharmaceutically acceptable salt thereof.

Representative species of Formula (III) and (IIIa) wherein X is hydrogen are:
1-Benzyl-5-phenyl-1H-[1,6]naphthyridin-2-one;
1,5-Diphenyl-1H-[1,6]naphthyridin-2-one; or a pharmaceutically acceptable salt thereof.

Compounds of Formula (I) and (Ia) wherein both $G_1$ and $G_2$ are either CH or $C(C_{1-4}alkyl)$, are respectively designated as 1,5,7-trisubstituted quinoline-2(1H)-one compounds and are also referred to herein as compounds of Formula (IV) and (IVa).

Accordingly compounds of Formula (IV) and (IVa) are represented by the structure:

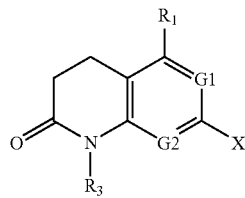
(IV)

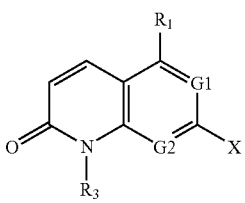
(IVa)

wherein
R$_1$ is an optionally substituted aryl or an optionally substituted heteroaryl ring;
X is R$_2$, OR$_2$, S(O)$_m$R$_2$, (CH$_2$)$_n$N(R$_{10}$)S(O)$_m$R$_2$, (CH$_2$)$_n$N(R$_{10}$)C(O)R$_2$, (CH$_2$)$_n$NR$_4$R$_{14}$, NR$_2$(CH$_2$)$_n$NR$_4$R$_{14}$, O(CH$_2$)$_n$NR$_4$R$_{14}$, S(CH$_2$)$_n$NR$_4$R$_{14}$, (CH$_2$)$_n$J, NR$_2$(CH$_2$)$_n$J, O(CH$_2$)$_n$J, S(CH$_2$)$_n$J, or (CH$_2$)$_n$N(R$_2$)$_2$;
J is an optionally substituted heteroaryl ring;
n is 0 or an integer having a value of 1 to 10;
m is 0 or an integer having a value of 1 or 2;
q is 0 or an integer having a value of 1 to 10;
R$_2$ is hydrogen, C$_{1-10}$ alkyl, aryl, arylC$_{1-10}$ alkyl, heteroaryl, heteroarylC$_{1-10}$ alkyl, which moieties are all optionally substituted, or R$_2$ is the moiety X$_1$(CR$_{10}$R$_{20}$)$_q$C(A$_1$)(A$_2$)(A$_3$), or C(A$_1$)(A$_2$)(A$_3$);
X$_1$ is N(R$_{10}$), O, S(O)$_m$, or CR$_{10}$R$_{20}$;
X$_2$ is independently hydrogen, halogen or C$_{1-4}$ alkyl;
A$_1$ is an optionally substituted C$_{1-10}$ alkyl;
A$_2$ is an optionally substituted C$_{1-10}$ alkyl;
A$_3$ is hydrogen or is an optionally substituted C$_{1-10}$ alkyl;
G$_1$ and G$_2$ are independently C—X$_2$;
R$_3$ is a hydrogen, C$_{1-10}$ alkyl, C$_{3-7}$ cycloalkyl, C$_{3-7}$ cycloalkylC$_{1-4}$alkyl, aryl, arylC$_{1-10}$ alkyl, heteroaryl, heteroarylC$_{1-10}$ alkyl, heterocyclic, or a heterocyclylC$_{1-10}$ alkyl moiety, which moieties are optionally substituted;
R$_4$ and R$_{14}$ are each independently selected from hydrogen, optionally substituted C$_{1-4}$ alkyl, optionally substituted aryl, or optionally substituted aryl-C$_{1-4}$ alkyl, arylC$_{1-10}$ alkyl, heteroaryl or heteroarylC$_{1-10}$ alkyl, wherein each of these moieties may be optionally substituted;
R$_{10}$ and R$_{20}$ are independently selected from hydrogen or C$_{1-4}$alkyl; provided that when
R$_1$ is phenyl, R$_2$ is methoxy substituted phenyl, X is (CH$_2$)$_n$NR$_4$R$_{14}$, n is 0, R$_4$ and
R$_{14}$ are other than both methyl;

a pharmaceutically acceptable salt thereof.
Suitably, when R$_1$ is a 2-chlorophenyl, or 2-Cl,4-F-phenyl and R$_3$ is a 2,6-dichlorophenyl, and X is OR$_2$, then R$_2$ is other than methyl. Suitably, when R$_1$ and R$_3$ are both halo substituted phenyl rings, and X is OR$_2$, then R$_2$ is other than C$_{1-10}$ alkyl.

Representative species of Formula (IV) and (IVa) are:
5-(2-fluorophenyl)-1-(4-flourophenyl)-2(1H)-quinolinone;
5-(4-fluorophenyl)-1-(4-fluorophenyl)-2(1H)-quinolinone;
5-(2,4-difluorophenyl)-1-(4-fluorophenyl)-2(1H)-quinolinone;
5-(4-methylphenyl)-1-(4-fluorophenyl)-2(1H)-quinolinone;
1,5-bis(2-chlorophenyl)-7-{[2-hydroxy-1-(hydroxymethyl)ethyl]amino}-2(1H)-quinolinone;
1,5-Bis(2-chlorophenyl)-7-{[2-(isopropylamino)ethyl]amino}-2(1H)-quinolinone;
6-bromo-1,5-bis(2-chlorophenyl)-7-(methyloxy)-2(1H)-quinolinone;
or a pharmaceutically acceptable salt thereof.

In another embodiment of the present invention, compounds or pharmaceutical compositions of Formula (V) and (Va) compounds have been found to be useful treating a CSBP/RK/p38 kinase mediated disease in a mammal in need thereof, comprising administering to said mammal an effective amount of a compound of Formula (V) or (Va).

Compounds of Formula (V) and (Va) are represented by the structure:

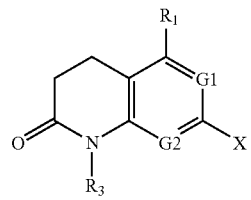
(V)

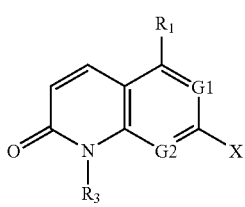
(Va)

wherein
R$_1$ is an optionally substituted aryl or an optionally substituted heteroaryl ring;
X is halogen, R$_2$, OR$_2$, S(O)$_m$R$_2$, (CH$_2$)$_n$N(R$_{10}$)S(O)$_m$R$_2$, (CH$_2$)$_n$N(R$_{10}$)C(O)R$_2$, (CH$_2$)$_n$NR$_4$R$_{14}$, NR2(CH2)nNR4R14, O(CH2)nNR4R14, S(CH2)nNR4R14, (CH$_2$)$_n$J, NR2(CH2)nJ, O(CH2)nJ, S(CH2)nJ, or (CH$_2$)$_n$N(R$_2$)$_2$;
J is an optionally substituted heteroaryl ring;
n is 0 or an integer having a value of 1 to 10;
m is 0 or an integer having a value of 1 or 2;
q is 0 or an integer having a value of 1 to 10;
R$_2$ is hydrogen, C$_{1-10}$ alkyl, aryl, arylC$_{1-10}$ alkyl, heteroaryl, heteroarylC$_{1-10}$ alkyl, which moieties are all optionally substituted, or R$_2$ is the moiety X$_1$(CR$_{10}$R$_{20}$)$_q$C(A$_1$)(A$_2$)(A$_3$), or C(A$_1$)(A$_2$)(A$_3$);
X$_1$ is N(R$_{10}$), O, S(O)$_m$, or CR$_{10}$R$_{20}$;
X$_2$ is independently hydrogen, halogen or C$_{1-4}$ alkyl;
A$_1$ is an optionally substituted C$_{1-10}$ alkyl;
A$_2$ is an optionally substituted C$_{1-10}$ alkyl;
A$_3$ is hydrogen or is an optionally substituted C$_{1-10}$ alkyl;
G$_1$ and G$_2$ are independently selected from is N, or C—X$_2$, provided that G$_1$ and G$_2$ are not both nitrogen;
R$_3$ is an hydrogen, C$_{1-10}$ alkyl, C$_{3-7}$ cycloalkyl, C$_{3-7}$ cycloalkylC$_{1-4}$alkyl, aryl, arylC$_{1-10}$ alkyl, heteroaryl, heteroarylC$_{1-10}$ alkyl, heterocyclic, or a heterocyclylC$_{1-10}$ alkyl moiety, which moieties are optionally substituted;
R$_4$ and R$_{14}$ are each independently selected from hydrogen, optionally substituted C$_{1-4}$ alkyl, optionally substituted aryl, or optionally substituted aryl-$C_{1-4}$ alkyl, aryl$C_{1-10}$ alkyl, heteroaryl or heteroaryl$C_{1-10}$ alkyl, wherein each of these moieties may be optionally substituted;

$R_9$ is hydrogen, C(Z)$R_6$ or optionally substituted $C_{10}$ alkyl, optionally substituted aryl or optionally substituted aryl-$C_{1-4}$ alkyl;

$R_{10}$ and $R_{20}$ are independently selected from hydrogen or $C_{1-4}$alkyl; or a pharmaceutically acceptable salt thereof.

Compounds of Formula (V) and (Va) include those of Formula (I) and (Ia) as well as compounds such as 1-methyl-5-phenyl-1H-[1,6]naphthyridin-2-one and 5-phenyl-1H-[1,6]naphthyridin-2-one which have also been found to be active as inhibitors of the CSBP kinase.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; S(O)m alkyl, such as methyl thio, methylsulfinyl or methyl sulfonyl; —C(O); NR$_{4'}$R$_{14'}$, wherein R$_{4'}$ and R$_{14'}$ are each independently hydrogen or $C_{1-4}$ alkyl, such as amino or mono or -disubstituted $C_{1-4}$ alkyl or wherein the R$_4$R$_{14'}$ can cyclize together with the nitrogen to which they are attached to form a 5 to 7 membered ring which optionally contains an additional heteroatom selected from O/N/S; $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such CF$_2$CF$_2$H, or CF$_3$; an optionally substituted aryl, such as phenyl, or an optionally substituted arylalkyl, such as benzyl or phenethyl, wherein these aryl containing moieties may also be substituted one to two times by halogen; hydroxy; hydroxy substituted alkyl; $C_{1-10}$ alkoxy; S(O)$_m$alkyl; amino, mono & di-substituted $C_{1-4}$ alkyl amino, such as in the NR$_4$R$_{14}$ group; $C_{1-4}$ alkyl, or CF$_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid.

In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The term "halo" or "halogens" is used herein to mean the halogens, chloro, fluoro, bromo and iodo.

The term "$C_{1-10}$alkyl" or "alkyl" or "alkyl$_{1-10}$" is used herein to mean both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2-10 carbon atoms, unless the chain length is limited thereto, including, but not limited to ethenyl, 1-propenyl, 2-propenyl, 2-methyl-1-propenyl, 1-butenyl, 2-butenyl and the like.

The term "aryl" is used herein to mean phenyl and naphthyl.

The term "heteroaryl" (on its own or in any combination, such as "heteroaryloxy", or "heteroaryl alkyl") is used herein to mean a 5-10 membered aromatic ring system in which one or more rings contain one or more heteroatoms selected from the group consisting of N, O or S, such as, but not limited to, pyrrole, pyrazole, furan, pyran, thiophene, quinoline, isoquinoline, quinazolinyl, pyridine, pyrimidine, pyridazine, pyrazine, uracil, oxadiazole, oxazole, isoxazole, oxathiadiazole, thiazole, isothiazole, thiadiazole, tetrazole, triazole, indazole, imidazole, or benzimidazole.

The term "heterocyclic" (on its own or in any combination, such as "heterocyclylalkyl") is used herein to mean a saturated or partially unsaturated 4-10 membered ring system in which one or more rings contain one or more heteroatoms selected from the group consisting of N, O, S, or S(O)m, and m is 0 or an integer having a value of 1 or 2; such as, but not limited to, the saturated or partially saturated versions of the heteroaryl moieties as defined above, such as tetrahydropyrrole, tetrahydropyran, tetrahydrofuran, tetrahydrothiophene (including oxidized versions of the sulfur moiety), pyrrolidine, piperidine, piperazine, morpholine, thiomorpholine (including oxidized versions of the sulfur moiety), or imidazolidine.

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate.

The term "sulfinyl" is used herein to mean the oxide S(O) of the corresponding sulfide, the term "thio" refers to the sulfide, and the term "sulfonyl" refers to the fully oxidized S(O)$_2$ moiety.

The term "aroyl" is used herein to mean C(O)Ar, wherein Ar is as phenyl, naphthyl, or aryl alkyl derivative such as defined above, such group include but are not limited to benzyl and phenethyl.

The term "alkanoyl" is used herein to mean C(O)$C_{1-10}$ alkyl wherein the alkyl is as defined above.

It is recognized that the compounds of the present invention may exist as stereoisomers, regioisomers, or diastereiomers. These compounds may contain one or more asymmetric carbon atoms and may exist in racemic and optically active forms. All of these individual compounds, isomers, and mixtures thereof are included within the scope of the present invention.

Exemplified compounds of the compounds of this invention include the racemates, or optically active forms of the compounds of the working examples herein, and pharmaceutically acceptable salts thereof.

Methods of Manufacture

The compounds of Formula (I), (Ia), may be obtained by applying synthetic procedures, described herein. The synthesis provided for is applicable to producing compounds of Formula (I), (Ia), having a variety of different $R_1$, $R_2$, Y, X, and $R_3$ groups which are reacted, employing optional substituents which are suitably protected, to achieve compatibility with the reactions outlined herein. Subsequent deprotection, in those cases, then affords compounds of the nature generally disclosed. While a particular formula with particular substituent groups is shown herein, the synthesis is applicable to all formulas and all substituent groups herein.

Once the nucleus has been established, further compounds of Formula (I), (Ia), (II) and (IIa) may be prepared by applying standard techniques for functional group interconversion, well known in the art. For instance: $C(O)NR_4R_{14}$ from $CO_2CH_3$ by heating with $HNR_4R_{14}$ in $CH_3OH$ with or without catalytic or stoichiometric metal cyanide or Aluminum trimethyl, e.g. NaCN; $OC(O)R_3$ from OH with e.g., $ClC(O)R_6$ in bases such as triethylamine and pyridine; $NR_{10}$—$C(S)NR_4R_{14}$ from $NHR_{10}$ with an alkylisothiocyanate, or thiocyanic acid and $ClC(S)NR_4R_{14}$; $NR_{10}C(O)OR_6$ from $NHR_{10}$ with an alkyl or aryl chloroformate; $NR_{10}C(O)NR_4H$ from $NHR_{10}$ by treatment with an isocyanate, e.g. $R_4N$=C=O; $NR_{10}$—$C(O)R_6$ from $NHR_{10}$ by treatment with $Cl$—$C(O)R_6$ in pyridine; $C(=NR_{10})NR_4R_{14}$ from $C(NR_4R_{14})S$ with $H_3NR_{10}$ $^+OAc^-$ by heating in alcohol; $C(NR_4R_{14})SR_6$ from $C(S)NR_4R_{14}$ with $R_6$—I in an inert solvent, e.g. acetone; $NR_{10}SO_2R_7$ from $NHR_{10}$ by treatment with $ClSO_2R_7$ by heating in bases such as pyridine; $NR_{10}C(S)R_6$ from $NR_{10}C(O)R_6$ by treatment with Lawesson's reagent [2,4-bis(4-methoxyphenyl)-1,3,2,4-dithiadiphosphetane-2,4-disulfide]; $NR_{10}SO_2CF_3$ from $NHR_{10}$ with triflic anhydride and base wherein $R_3$, $R_6$, $R_{10}$, $R_4$ and $R_{14}$ are as defined in Formula (I) herein.

Precursors of the groups $R_1$, $R_2$ and $R_3$, can be other $R_1$, $R_2$ and $R_3$, etc groups that may be interconverted by applying standard techniques for functional group interconversion. For example wherein a moiety is a halo substituted $C_{1-10}$ alkyl can be converted to the corresponding $C_{1-10}$ alkyl$N_3$ derivative by reacting with a suitable azide salt, and thereafter if desired can be reduced to the corresponding $C_{1-10}$alkyl$NH_2$ compound, which in turn can be reacted with $R_7S(0)_2X$ wherein X is halo (e.g., chloro) to yield the corresponding $C_{1-10}$alkyl$NHS(0)_2R_7$ compound.

Alternatively wherein the moiety is a halo-substituted $C_{1-10}$-alkyl it can be reacted with an amine $R_4R_{14}NH$ to yield the corresponding $C_{1-10}$-alkyl$NR_4R_{14}$ compound, or can be reacted with an alkali metal salt of $R_7SH$ to yield the corresponding $C_{1-10}$alkyl$SR_7$ compound.

As noted above, it may be desirable during the synthesis of the compounds of this invention, to derivatize reactive functional groups in the molecule undergoing reaction so as to avoid unwanted side reactions. Functional groups such as hydroxy, amino, an acid groups typically are protected with suitable groups that can be readily removed when desired. Suitable common protecting groups for use with hydroxyl groups and nitrogen groups are well known in the art and described in many references, for instance, Protecting Groups in Organic Synthesis, Greene et al., John Wiley & Sons, New York, N.Y., (2nd edition, 1991 or the earlier 1981 version). Suitable examples of hydroxyl protecting groups include ether forming groups such as benzyl, and aryl groups such as tert-butoxycarbonyl (Boc), silyl ethers, such as t-butyldimethyl or t-butyldiphenyl, and alkyl ethers, such as methyl connected by an alkyl chain of variable link, $(CR_{10}R_{20})_n$. Amino protecting groups may include benzyl, aryl such as acetyl and trialkylsilyl groups. Carboxylic acid groups are typically protected by conversion to an ester that can easily be hydrolyzed, for example, trichloroethyl, tert-butyl, benzyl and the like.

Pharmaceutically acceptable acid addition salts of compounds of Formula (I), (Ia), (II) and (IIa) may be obtained in known manner, for example by treatment thereof with an appropriate amount of acid in the presence of a suitable solvent.

An illustration of the preparation of compounds of the present invention are shown in the schemes below.

Scheme 1

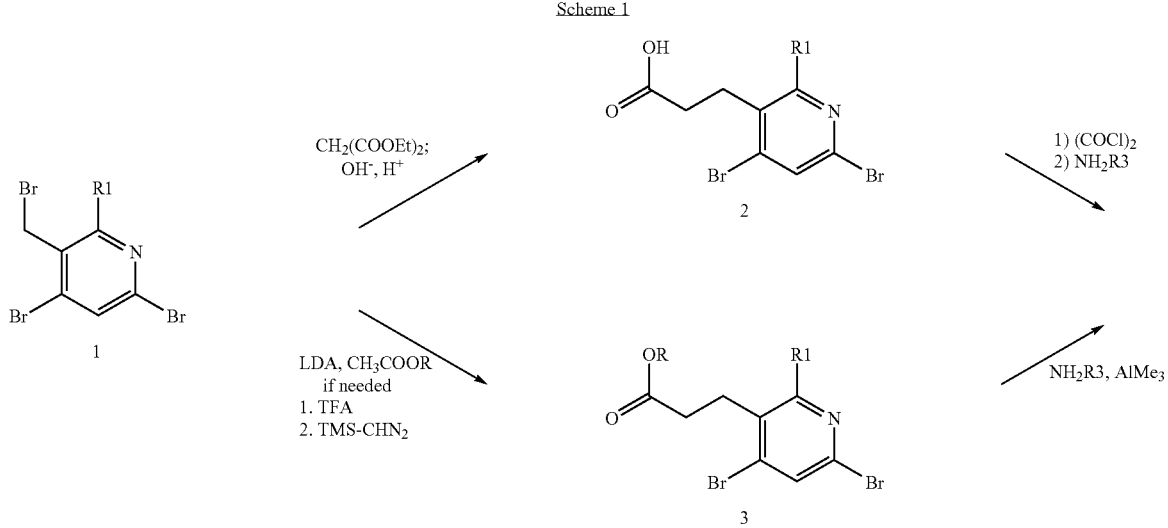

-continued

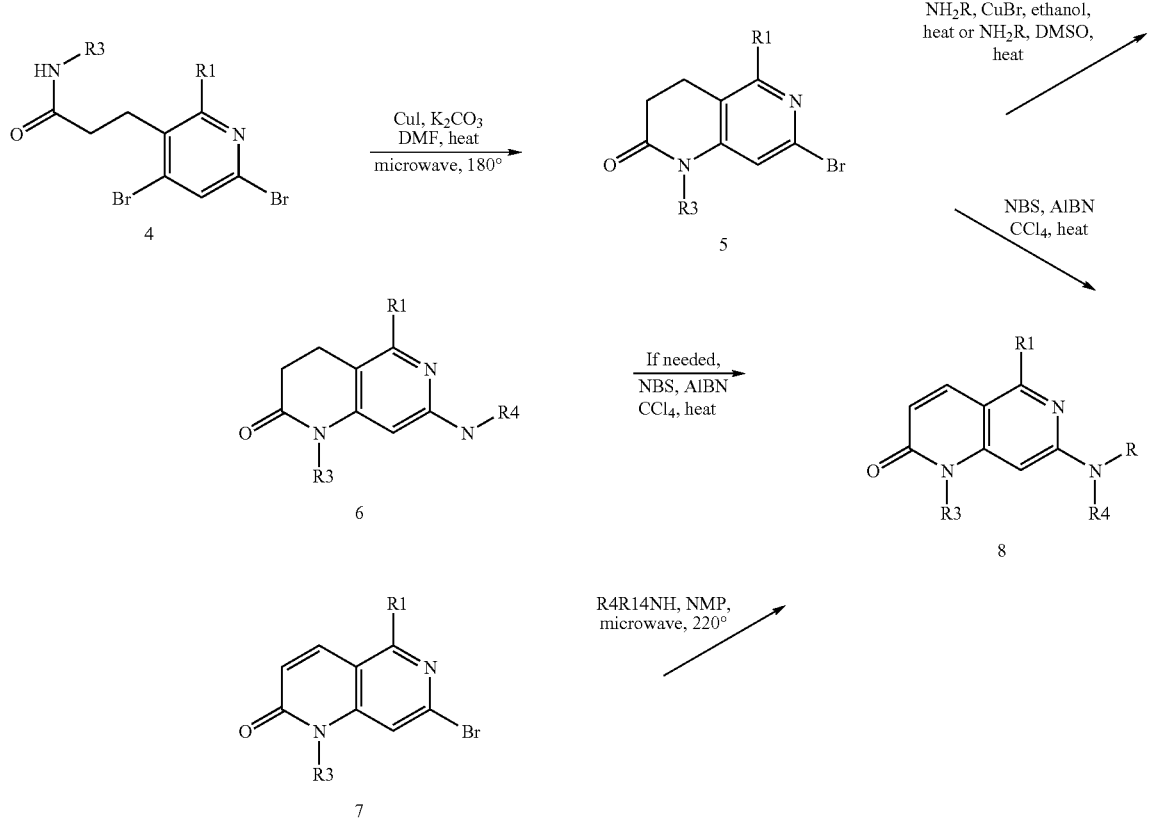

1H-[1,6]Naphthyridin-2-ones may be prepared by the route depicted in Scheme 1. The starting material 1-Scheme 1 may be obtained from the commercially available 2-amino-3-methylpyridine by known literature procedures, such as those noted in International Publication No. WO 02/058695 A1. $R_1$ could be aryl, cyclic or noncyclic alkyl group. The intermediate 4-Scheme 1 may be produced by two different procedures. In the first procedure, coupling of the aryl bromide 1-Scheme 1 with malonate or mono malonate in the presence of sodium hydride in THF afford the desired compound 2-Scheme 1 after the required saponification and decarboxylation. Other suitable bases, including but not limited to lithium hydride, potassium hydride, sodium ethoxide, butyl lithium, may also be used in an appropriate organic solvent, including but not limited to DMF, diethyl ether, dioxane. The carboxylic acid 2-Scheme 1 may be then converted to the corresponding activated carboxylate. For example the acid chloride may be prepared, using oxalyl chloride or thionyl chloride, or related reagent and coupled with the requisite amine to provide the amide 4-Scheme 1.

In the second procedure, the aryl bromide 1-Scheme 1 may be treated with alkyl acetate such as tert-butyl acetate or ethyl acetate in the presence of suitable bases, including but are not limited to LDA, BuLi, KHMDS, NaHMDS, to provide the desired ester 3-Scheme 1. If the ester was tert-butyl, it may be cleaved with TFA to the carboxylic acid, which may be converted to the methyl ester with any one of a number of known methods such as with trimethylsilyldiazomethane. The ester may be then converted to the amide 4-Scheme 1 by treatment with AlMe$_3$ and the corresponding amine.

The cyclization of the amide 4-Scheme 1 to afford 5-Scheme 1 may be completed by heating the reaction in DMF with copper(I) iodide and potassium carbonate. The reaction had fewer impurities and was shortened in duration if heating was accompanied by microwave irradiation. Other suitable bases, including, but not limited to lithium-hydride, sodium hydride, pyridine, may be used in an appropriate organic solvent such as methyl sulfoxide, ethoxyethanol (see for example Boschelli, D. H. et al. *J. Med. Chem.* 2001, 44, 822). Alternatively, the cyclization reaction may also be performed using a palladium catalyst such as Pd$_2$(dba)$_3$ with the suitable phosphorous ligands, including but not limited to tri(tert-butyl)phosphine, (o-biphenyl)P(t-Bu)$_2$, (o-biphenyl)PCy$_2$ (See for example Yang, B. H.; Buchwald, S. L. *Org. Lett.* 1999, 1, 35-37.).

Displacements of the bromide 5-Scheme 1 to the product 6-Scheme 1 were completed with an excess of amine in polar solvent, including but not limited to N-methylpyrrolidin-2-one (NMP), ethanol, methanol, DMSO, with or without copper (I) salt, and at varying temperatures depending upon the nucleophilicity of the amine (see for example Terauchi, H. et al. *Chem. Pharm. Bull.* 2001, 45,1027). The reaction had fewer impurities and was shortened in duration if heating was accompanied by microwave irradiation. The bromide may also be displaced with a substituted arylamine, or heteroarylamine at elevated temperatures, sometimes requiring formation of the aryl or heteroarylamine anion with sodium hydride, or other suitable base, in DMSO. Alternatively, the displacements may also be performed using a palladium catalyst such as but not limited to tetrakis(triphenylphosphine)-palladium(0) with the suitable base, including but not limited to potassium t-butoxide, sodium carbonate, cesium carbonate (see for example Grasa, G. A. et al. *J. Org. Chem.* 2001, 66, 7729).

Oxidation of 6-Scheme 1 to 8-Scheme 1 could be achieved via a bromination and elimination process with N-bromosuccinimide and AIBN. This process could also be completed via an α-oxidation of the amide 6-Scheme 1 by using a suitable oxidation reagent such as Davis reagent (Davis, F. A.; Sheppard, A. C. *Tetrahedron* 1989, 45, 5703), followed by an elimination to provide 8-Scheme 1. $MnO_2$ was also an effective reagent for dehydrogenation to 8-Scheme 1. DDQ also would carry out this transformation. Alternatively, bromide 5-Scheme 1 could first be dehydrogenated to afford 7-Scheme 1 by the same procedures as described above for the conversion of 6 to 8 in Scheme 1. The bromide 7-Scheme 1 was then be displaced with amines in the same manner as the conversion of 5 to 7 in Scheme 1. For example, treatment of 7-Scheme 1 with primary alkylamines in NMP at 220° for 30 min. with microwave irradiation afforded the aminated analogs 8-Scheme 1, $R_4$=H, $R_{14}$=alkyl.

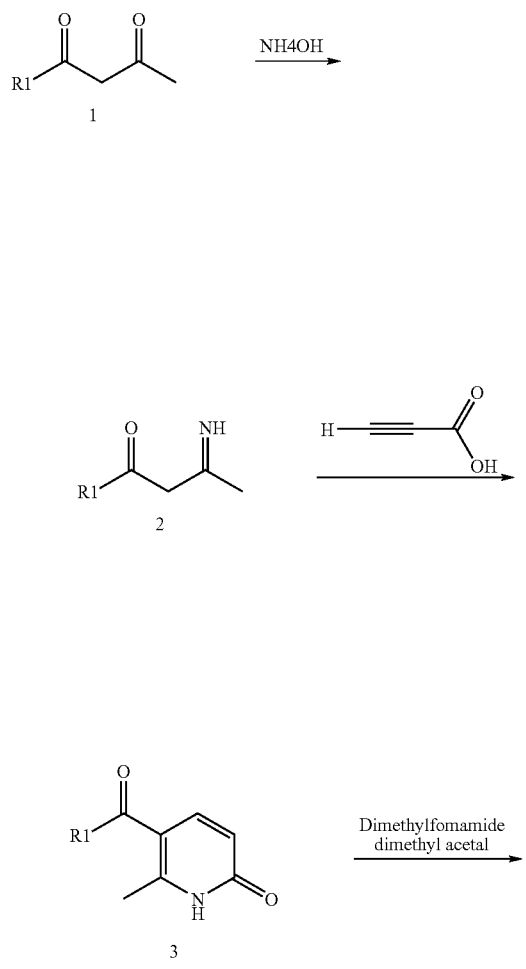

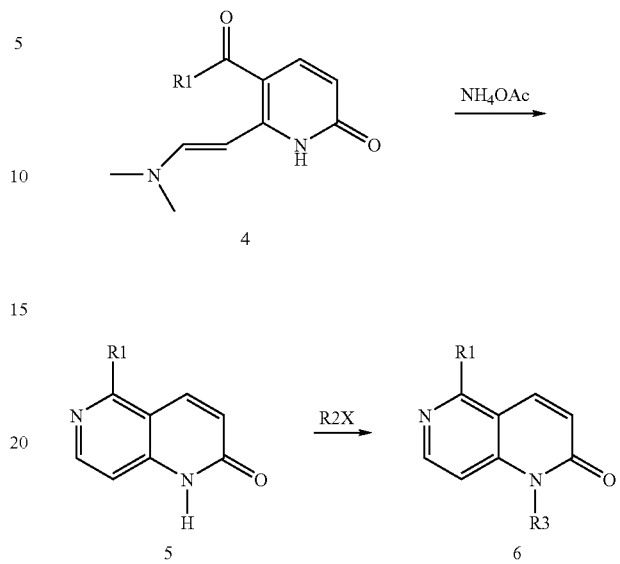

1H-[1,6]Naphthyridin-2-ones may also be prepared from a suitable 1-substitututed-1,3-butanedione 1-Scheme 2. For purposes herein $R_2$ is $R_3$ in Formula (I) and (Ia). Some of the substututed-1,3-butanediones are commercially available; while others can be readily prepared following literature procedures, such as the preparation of 1-aryl-1,3-butanediones from aryl esters as exemplified by Chaney et. al., *J. Org. Chem.* 1951, 57-58. Heteroaryl-1,3-butanediones have also been prepared from heteroaryl esters as exemplified by Ferenczy, *Monatsh. Chem.* 1897, 674. Cycloalkyl-1,3-butanediones have been prepared from cycloalkyl methyl ketones as exemplified by Sprague et. al., *J. Am. Chem. Soc.* 1934, 2655-2666. Alkyl-1,3 butanediones have been prepared from alkyl methylketones as exemplified by Adams et. al., *J. Am. Chem. Soc.* 1945, 285. Reaction of compound 1-Scheme 2 with ammonium hydroxide in a suitable solvent such as methanol gives the imine 2-Scheme 2. Reaction of imine 2-Scheme 2 with an acetylenic ester such as methyl propiolate in a suitable solvent such as DMF at elevated temperature gives the 5-substituted-6-methyl-2(1H)-pyridinone 3-Scheme 2. Compound 3-Scheme 2 is reacted with N,N-dimethylformamide dimethyl acetal in a suitable solvent such as DMF at elevated temperature to give the corresponding 5-substituted-6-[2-dimethylamino)ethenyl]-2(1H)-pyridinone 4-Scheme 2. Conversion of compound 4-Scheme 2 to the 5-substituted-1H-[1,6]naphthyridin-2-one 5-Scheme 2 is accomplished by heating compound 4-Scheme 2 with ammonium acetate in a suitable solvent such as DMF. Alkylation of compound 5-Scheme 2 with a suitable alkylating agent $R_2X$ such as an alkyl halide in a suitable solvent such as DMF or acetone, with a suitable base such as potassium carbonate or sodium hydride gives the 1H-[1,6]Naphthyridin-2-ones 6-Scheme 2. The general procedure for conversion of compounds 1-Scheme 2 into Compounds 6-Scheme 2 was exemplified by Lesher et al., in U.S. Pat. No. 4,560,691. Alternatively the compound 6-Scheme 2 where $R_2$ is aryl or heteroaryl can be prepared from compound 5-Scheme 2 by reacting with an arylboronic acid in the presence of a suitable catalyst such as cupric acetate and a suitable base such as triethylamine or pyridine. This procedure was exemplified by Chan et. al., *Tett. Lett.* 1998, 2933-2936.

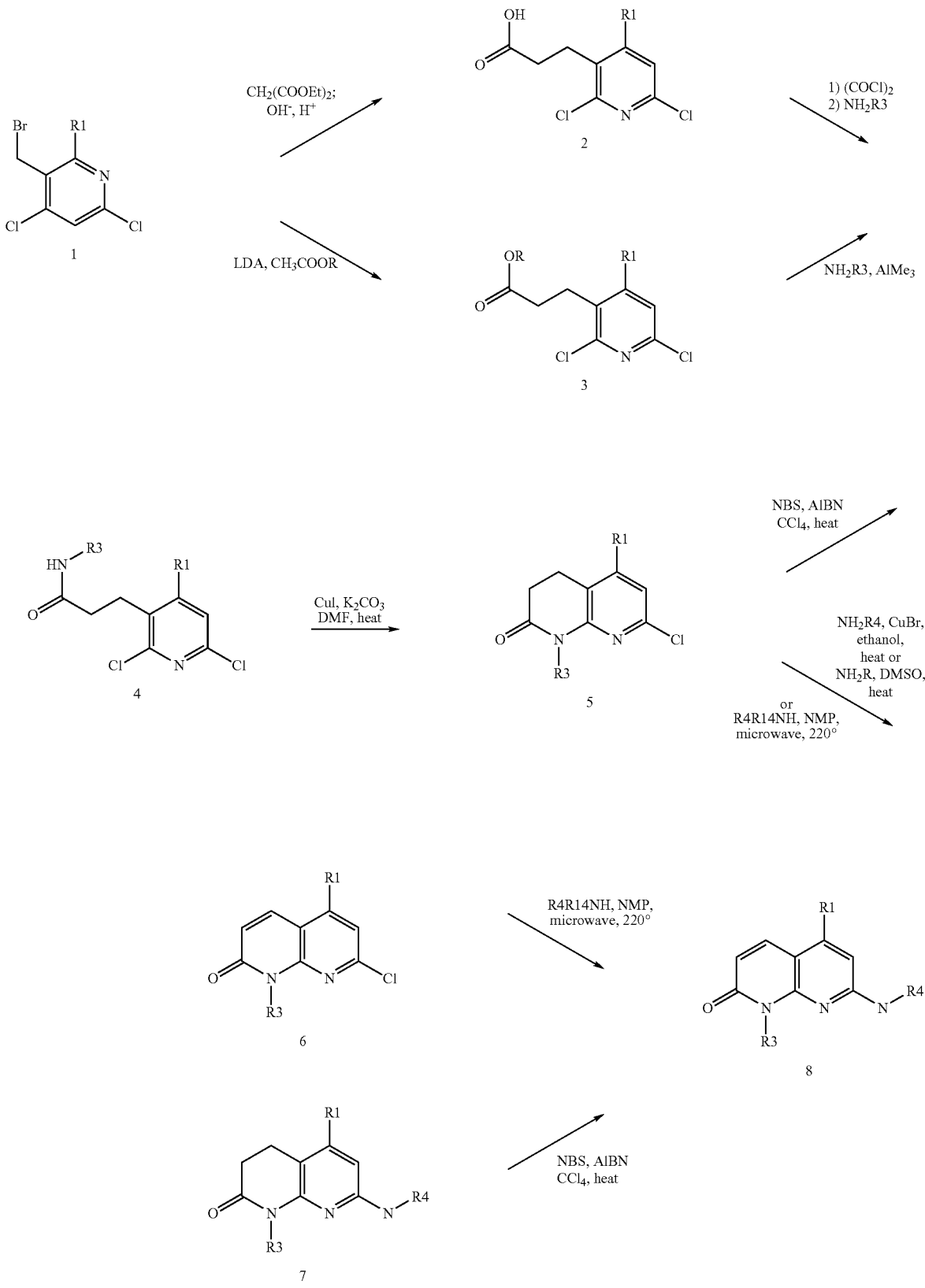

1H-[1,8]Naphthyridin-2-ones may be prepared by the route depicted in Scheme 3. The starting material 1-Scheme 3 may be obtained by known literature procedures, such as those noted in International Publication No. WO 02/058695 A1. $R_1$ could be aryl, cyclic or noncyclic alkyl group.

The intermediate 4-Scheme 3 may be produced by two different procedures. In the first procedure, coupling of 1-Scheme 3 with malonate or mono malonate in the presence of sodium hydride in THF affords the desired compound 2-Scheme 3 after the required saponification and decarboxylation. Other suitable base, includes but are not limited to lithium hydride, potassium hydride, sodium ethoxide, butyl lithium, used in an appropriate organic solvent, including but not limited to DMF, diethyl ether, dioxane. The carboxylic acid 2-Scheme 3 may be then converted to the corresponding activated carboxylate. For example the acid chloride may be prepared, using oxalyl chloride or thionyl chloride, or related reagent to afford the activated carboxylate which may be coupled with the requisite amine to provide the amide 4-Scheme 3.

In the second procedure, 1-Scheme 3 is treated with alkyl acetate such as tert-butyl acetate or ethyl acetate in the presence of suitable bases, including but are not limited to LDA, BuLi, KHMDS, NaHMDS, to provide the desired ester 3-Scheme 3. If the ester is tert-butyl, it may be cleaved with TFA to the carboxylic acid, which may be converted to the methyl ester by any one of a number of known methods such as with trimethylsilyldiazomethane. The ester is then converted to the amide 4-Scheme 3 by treatment with AlMe$_3$ and the corresponding amine.

The cyclization of the amide 4-Scheme 3 is completed by heating the reaction in DMF with copper(I) iodide and potassium carbonate to afford 5-Scheme 3. Other suitable base, includes but are not limited to lithium hydride, sodium hydride, pyridine, used in an appropriate organic solvent such as methyl sulfoxide, ethoxyethanol (see for example Boschelli, D. H. et al. *J. Med. Chem.* 2001, 44, 822). Alternatively, the cyclization reaction may also be performed using a palladium catalyst such as Pd$_2$(dba)$_3$ with the suitable phosphorous ligands, including but not limited to tri(tert-butyl) phosphine, (o-biphenyl)P(t-Bu)$_2$, (o-biphenyl)PCy$_2$ (See for example Yang, B. H.; Buchwald, S. L. *Org. Lett.* 1999, 1, 35-37.).

Oxidation of 5-Scheme 3 to 6-Scheme 3 could be achieved via a bromination and elimination process with N-bromosuccinimide and AIBN. This process could also be completed via an α-oxidation of 5-Scheme 3 by using a suitable oxidation reagent such as Davis reagent (Davis, F. A.; Sheppard, A. C. *Tetrahedron* 1989, 45, 5703), followed by an elimination to provide 6-Scheme 3. MnO$_2$ is also an effective reagent for this transformation, as is also DDQ.

Displacements of the chloride in 6-Scheme 3 to 8-Scheme 3 were completed with an excess of amine in polar solvent, including but not limited to N-methyl pyrrolidin-2-one (NMP), ethanol, methanol, DMSO, with or without copper (I) salt, and at varying temperatures depending upon the nucleophilicity of the amine (see for example Terauchi, H. et al. *Chem. Pharm. Bull.* 2001, 45, 1027). The reaction had fewer impurities and was shortened in duration if heating was accompanied by microwave irradiation. The chloride may also be displaced with a substituted arylamine, or heteroarylamine at elevated temperatures, sometimes requiring formation of the aryl or heteroarylamine anion with sodium hydride, or other suitable base, in DMSO. Alternatively, the displacements may also be performed using a palladium catalyst such as but not limited to tetrakis(triphenyl-phosphine) palladium(0) with the suitable base, including but not limited to t-butoxide, sodium carbonate, cesium carbonate (see for example Grasa, G. A. et al. *J. Org. Chem.* 2001, 66, 7729). Aeb;normal lternatively, the conversion of 5-Scheme 3 to 8-Scheme 3 could be effected by reversal of the sequence of the above two reactions, first displacing the chloride as described above to afford 7-Scheme 3, followed by the dehydrogenation step under the previously described conditions to afford 8-Scheme 3.

Scheme 4

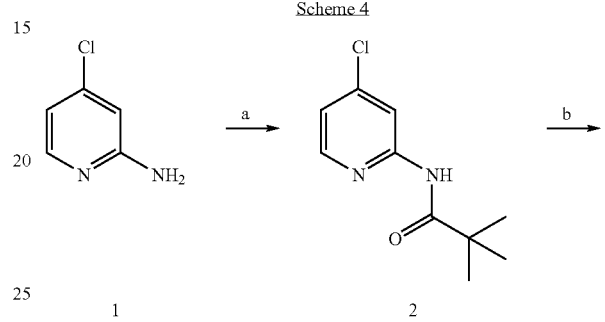

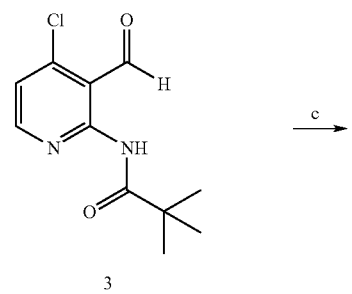

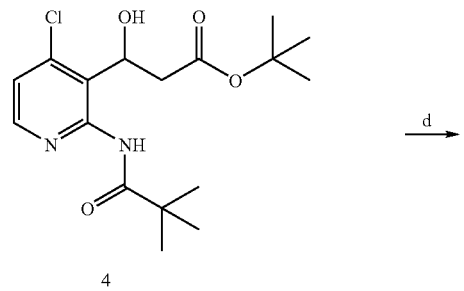

-continued

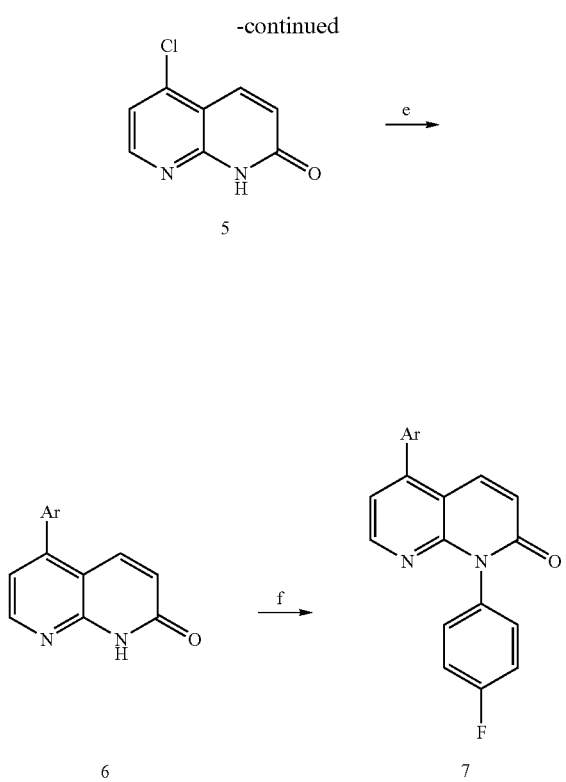

a, pivaloyl chloride/Et₃N/CH₂Cl₂; b, i) n-BuLi/THF ii) DMF; c, LDA/THF/tert-butyl acetate; d, 3M HCl; e, ArB(OH)₂/(Ph₃P)₄Pd/aq. K₂CO₃/ethylene glycol dimethyl ether; f, 4-fluorophenylboronic acid/Cu(OAc)₂/pyridine/Et₃N/CH₂Cl₂/powdered 4 Å sieves.

Another synthesis of the 1H-[1,8]Naphthyridin-2-ones is depicted in Scheme 4. 4-Chloro-2-aminopyridine, 1-Scheme 4, (prepared by the literature procedure: Townsend, L. B. et al *Synthetic Commun.* 1997 27, 861-870) was acylated with pivaloyl chloride and triethylamine in methylene chloride to afford 2-Scheme 4. This transformation is readily achieved with pivaloyl chloride or other pivalic acid activated esters under a variety of other well known conditions for amide formation such as those described in standard textbooks of organic synthesis (for example March J. *Advanced Organic Chemistry. Reactions, Mechanims and Structure* 1985, 3rd ed. 370-371).

The pivalamide was then regioselectively lithiated at the 3 position with n-butyl lithium and formylated with dimethylformamide (DMF) affording 3-Scheme 4. This stereoselectivity is likely aided by coordination of the lithium with the amide (for example see Tamura, Y. et al., *Chem Pharm Bull.* 1982, 30. 1257-1262). Similar regioselectivity is also possible without the benefit of coordinating functionality by treatment of 4-chloropyridine with n-butyllithium-tetramethylenediamine (TMEDA) chelate or lithium diisopropylamide (LDA) or similar dialkylamide bases. (Queguiner, G. et al *J. Heterocyclic Chem* 1988, 25, 81-87).

Addition of the anion of tert-butyl acetate to the formylated pyridine gave 4-Scheme 4, and acid promoted cyclization/dehydration of 4-Scheme 4 afforded 5-chloro[1,8]naphthyridin-2(1H)-one 5-Scheme 4. Condensation of kinetically generated ester enolates of other esters is also possible. Alternatively alkyl acetoacetate anion may react with the aldehyde 3-Scheme 4 to form an aldol addition product which may be cyclized, hydrolyzed and, decarboxylated to afford the desired ring system.

The Suzuki reaction of 5-Scheme 4 with aryl boronic acids using a palladium catalyst, such as, tetrakis(triphenylphosphine)palladium(0) catalyst proceeds to afford 6-Scheme 4. This is a well known reaction, which proceeds efficiently on electron deficient chloro-heterocycles such as 5-Scheme 4 (Ali, N M et al *Tetrahedron* 1992, 48, 8117-8126). Alternatively, the bi-aryl coupling reaction of 5-Scheme 4 can be performed using aryl or heteroaryl organozinc, organcopper, organotin, or other organometallic reagents known to afford bi-aryl cross-coupling products [See for example Solberg, J.; Undheim, K. *Acta Chemica Scandinavia* 1989, 62-68]. Displacement of the chlorine in 5-Scheme 4 may also be achieved with nitrogen nucleophiles.

The final products 7-Scheme 4 were synthesised via a copper acetate mediated arylation of the pyridone nitrogen of 6-Scheme 4 with arylboronic acids as originally described by Lam and Chan (Tetrahedron Lett 1998, 2941) and extended to pyridones by Mederski and co-workers (Tetrahedron 1999, 12757). More recently Lam and co-workers extended these procedures to allow the use of catalytic Cu(OAc)2 with in situ reoxidation of the Cu(OAc)₂ in the presence of oxidizing agents (Tetrahedron Lett. 2001, 3415). In addition to coupling with arylboronic acids, such Cu(OAc)2 mediated amide arylations may also be effected using other organometalloids such as hypervalent diaryliodonium salts, aryl siloxanes, arylbismuths or arylstannanes.

Alternatively the arylation step may be effected using Buchwald's procedures for amide arylation with arylbromides, triflates or iodides in the presence of a suitable palladium catalyst and base (*Organic Lett.* 2000 1101).

Scheme 5

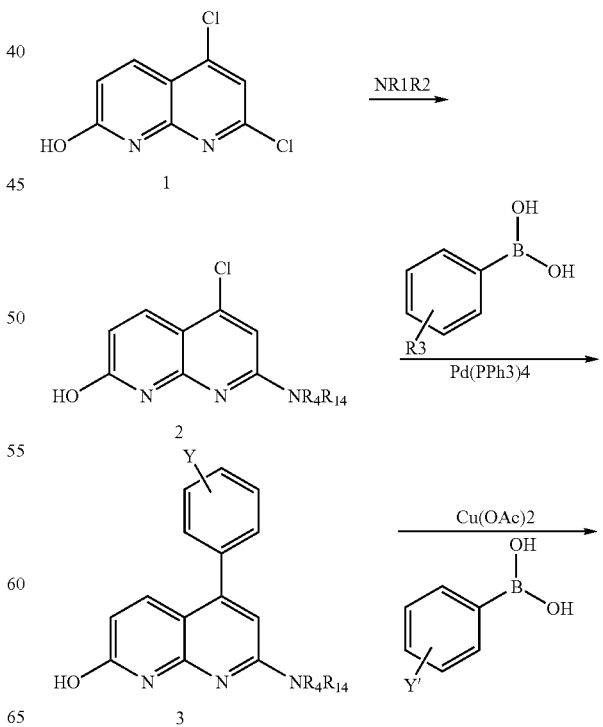

-continued

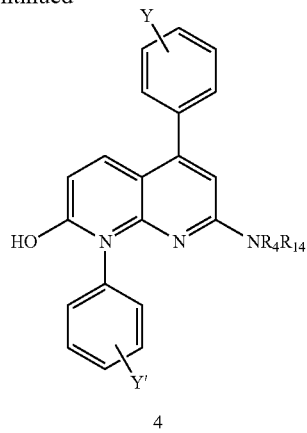

4

This series of 1H-[1,8]Naphthyridin-2-ones may also be prepared as depicted in Scheme 5 by an alternative method, which permits substitution at the napthyridine C-7. Utilizing previously reported chemistry, the known 5,7-dichloro[1,8] napthyridin-2-ol 1-Scheme 5 (Ferrarini, P L et al Eur. J. Med. Chem. 1998, 33, 383-397) is regioselectively displaced with amines to afford 7-amino napthyridines (Ferrarini, P L et al Eur. J. Med. Chem. 1998, 33, 383-397).

The Suzuki reaction of 2-Scheme 5 with aryl boronic acids using a palladium catalyst, such as, tetrakis(triphenylphosphine)palladium(0) catalyst proceeds to afford 3-Scheme 5. This is a well known reaction, which proceeds efficiently on electron deficient chloro-heterocycles such as 2-Scheme 5 (Ali, N M et al Tetrahedron 1992, 48, 8117-8126). Alternatively, the bi-aryl coupling reaction of 2-Scheme 5 can be performed using aryl or heteroaryl organozinc, organcopper, organotin, or other organometallic reagents known to afford bi-aryl cross-coupling products [See for example Solberg, J.; Undheim, K. Acta Chemica Scandinavia 1989, 62-68]. Displacement of the chlorine in 2-Scheme 5 may also be achieved with nitrogen nucleophiles.

Compound 3-Scheme 5 then reacts via its amide tautomer via a copper acetate mediated arylation of the pyridone nitrogen of 3-Scheme 5 with arylboronic acids as originally described by Lam and Chan (Tetrahedron Lett 1998, 2941) and extended to pyridones by Mederski and co-workers (Tetrahedron 1999, 12757) This sequence of reactions affords the desired 1,8 napthyridinones. More recently Lam and co-workers extended these procedures to allow the use of catalytic Cu(OAc)2 with in situ reoxidation of the Cu(OAc)$_2$ in the presence of oxidizing agents (Tetrahedron Lett 2001, 3415). In addition to coupling with arylboronic acids, such Cu(OAc)$_2$ mediated amide arylations may also be effected using other organometalloids such as hypervalent diaryliodonium salts, aryl siloxanes, arylbismuths or aryistannanes. Y is an optional substituent on the $R_1$ moiety, and Y' is an optional substituent on the $R_3$ moiety as described herein in the specification.

Scheme 6

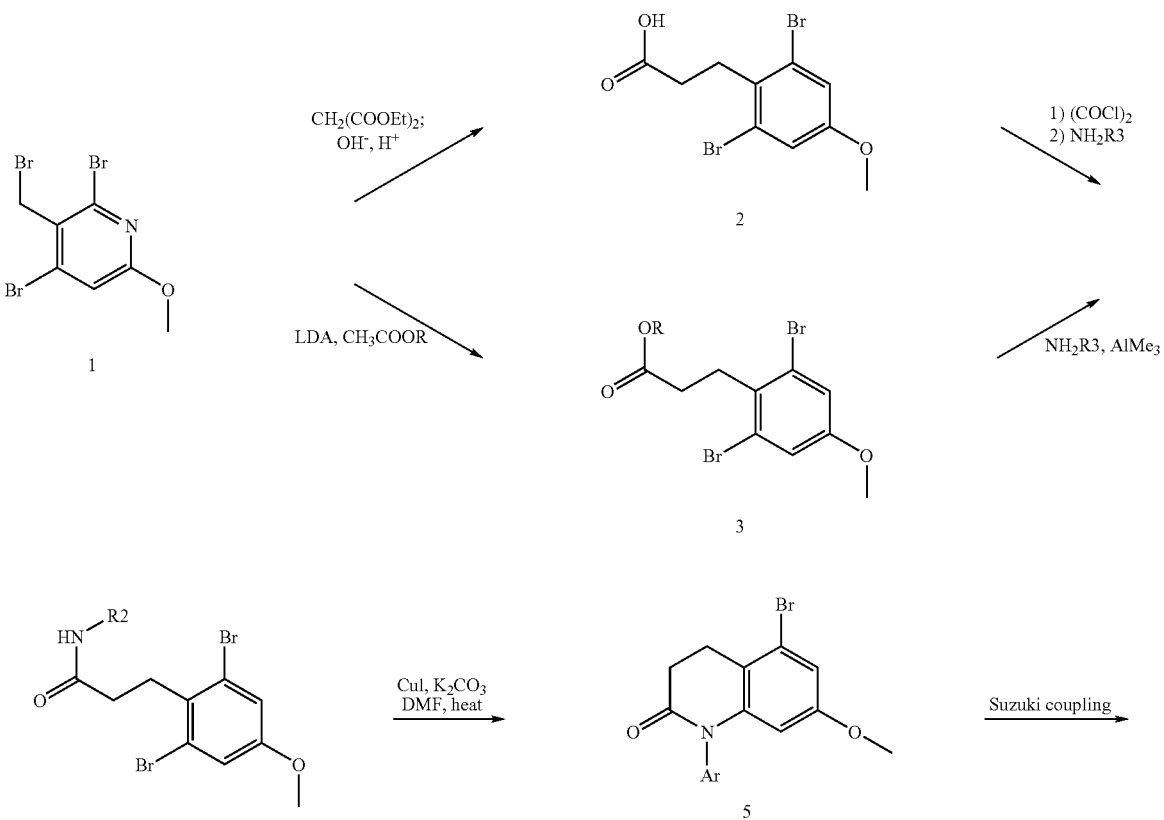

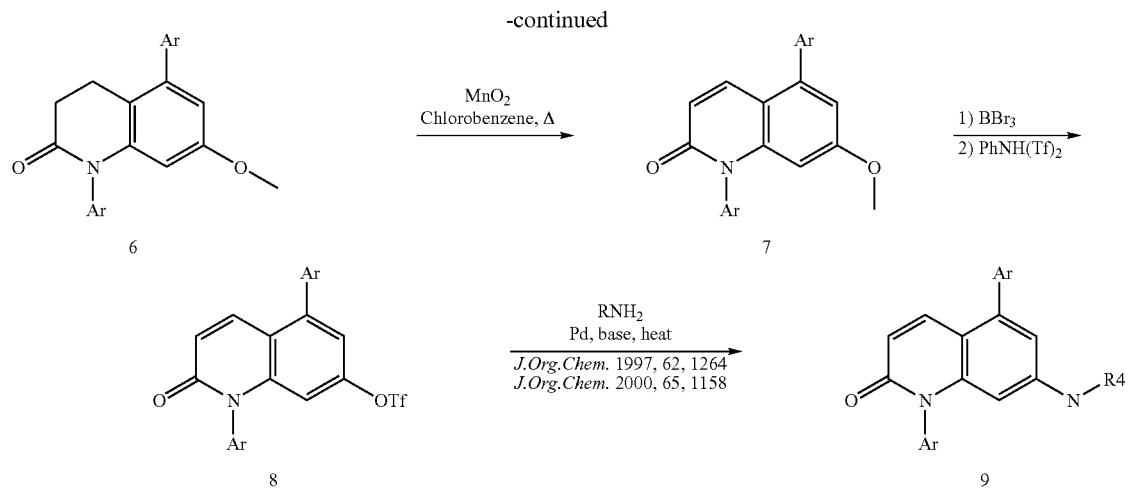

A series of 2(1H)-quinolones are prepared as depicted in Scheme 6. The starting material 1-Scheme 6 may be obtained from the commercially available 1,3-dibromo-5-methoxy-2-methylbenzene by known literature procedures, such as those noted in International Publication No. WO 02/058695 A1.

The intermediate 4-Scheme 6 was produced by two different procedures. In the first procedure, coupling of the bromide 1-Scheme 6 with malonate or mono malonate in the presence of sodium hydride in THF afforded the desired compound 2-Scheme 6 after the required saponification and decarboxylation. Other suitable bases, including but are not limited to lithium hydride, potassium hydride, sodium ethoxide, butyl lithium, may also be used in an appropriate organic solvent, including but not limited to DMF, diethyl ether, dioxane and ethanol. The carboxylic acid 2-Scheme 6 may be then converted to the corresponding activated carboxylate. For example the acid chloride may be prepared, using oxalyl chloride or thionyl chloride, or related reagent. The resulting activated Carboxylate is then coupled with the requisite amine to provide the amide 4-Scheme 6.

In the second procedure, the bromide 1-Scheme 6 was treated with alkyl acetate such as tert-butyl acetate or ethyl acetate in the presence of suitable bases, including but not limited to LDA, BuLi, KHMDS, NaHMDS, to provide the desired ester 3-Scheme 6. If the ester is tert-butyl, it may be cleaved with TFA to the carboxylic acid, which may be converted to the methyl ester with any one of a number of known methods such as with trimethylsilyldiazomethane. The ester was then converted to the amide 4-Scheme 6 by treatment with AlMe$_3$ and the corresponding amine.

The cyclization of the amide 4-Scheme 6 to afford 5-Scheme 6 was completed by heating the reaction in DMF with copper(I) iodide and potassium carbonate. The reaction had fewer impurities and was shortened in duration if heating was accompanied by microwave irradiation. Other suitable bases, include but are not limited to lithium hydride, sodium hydride, potassium hydride, pyridine, maybe used in an appropriate organic solvent such as DMSO, ethoxyethanol (see for example Boschelli, D. H. et al. *J. Med. Chem.* 2001, 44, 822). Alternatively, the cyclization reaction may also be performed using a palladium catalyst such as Pd$_2$(dba)$_3$ with the suitable phosphorous ligands, including but not limited to tri(tert-butyl)phosphine, to (o-biphenyl)P(t-Bu)$_2$, (o-biphenyl)PCy$_2$ (See for example Yang, B. H.; Buchwald, S. L. *Org. Lett* 1999, 1, 35-37).

The aryl bromide 5-Scheme 6 was coupled to arylboronic acids under Suzuki coupling conditions, using a palladium catalyst, such as tetrakis(triphenylphosphine)-palladium(0), to afford good to excellent yields of 6-Scheme 6. Alternatively, the biaryl coupling reaction of 5-Scheme 6 may be performed using aryl or heteroaryl organozinc, organocopper, organotin, or other organometallic reagents known to afford biaryl cross-coupling products such as 6-Scheme 6 (see for example Solberg, J.; Undheim, K. *Acta. Chemica. Scandinavia.* 1989, 62).

Oxidation of 6-Scheme 6 to 7-Scheme 6 could be achieved via a bromination and elimination process with N-bromosuccinimide and AlBN as reported above for the napthyridinone scaffolds, however, this was problematic as a result of concomitant bromination of the quinilone ring. Alternatively, oxidative dehydrogenolysis was achieved by treating 6-Scheme 6 with MnO$_2$ without side reactions. This process could also be completed via an α-oxidation of 6-Scheme 6 using other suitable oxidation reagents such as Davis reagent (Davis, F. A.; Sheppard, A. C. *Tetrahedron* 1989, 45, 5703), followed by an elimination to provide 7-Scheme 6. DDQ is also an effective reagent for this transformation.

The methyl ether 7-Scheme 6 was cleaved using boron tribromide, and treated with N-phenyltrifluoromethanesulfonimide to give the triflate 8-Scheme 6. Other suitable triflating reagents such as trifluoromethanesulfonic anhydride could also be used.

Finally, the triflate 8-Scheme 6 was coupled to aryl amine or alkyl amine under amination conditions to give the aryl amine 9-Scheme 6, using palladium complexes supported by phosphine ligands, including but not limited to (o-biphenyl)P(t-Bu)$_2$, (o-biphenyl)PCy$_2$, tri(tert-butyl)phosphine (see Buchwald, S. L. *J. Org. Chem.* 2000, 65, 1158). Alternatively, oxygen nucleophiles could also be used in the coupling reaction to provide the corresponding aryl ether derivatives (see Hartwig, J. F. *Angew. Chem. Int. Ed.* 1998, 37, 2046). Ar is an optionally substituted aryl for the R$_3$ moiety, and R$_4$ is as described herein in the specification.

Scheme 7

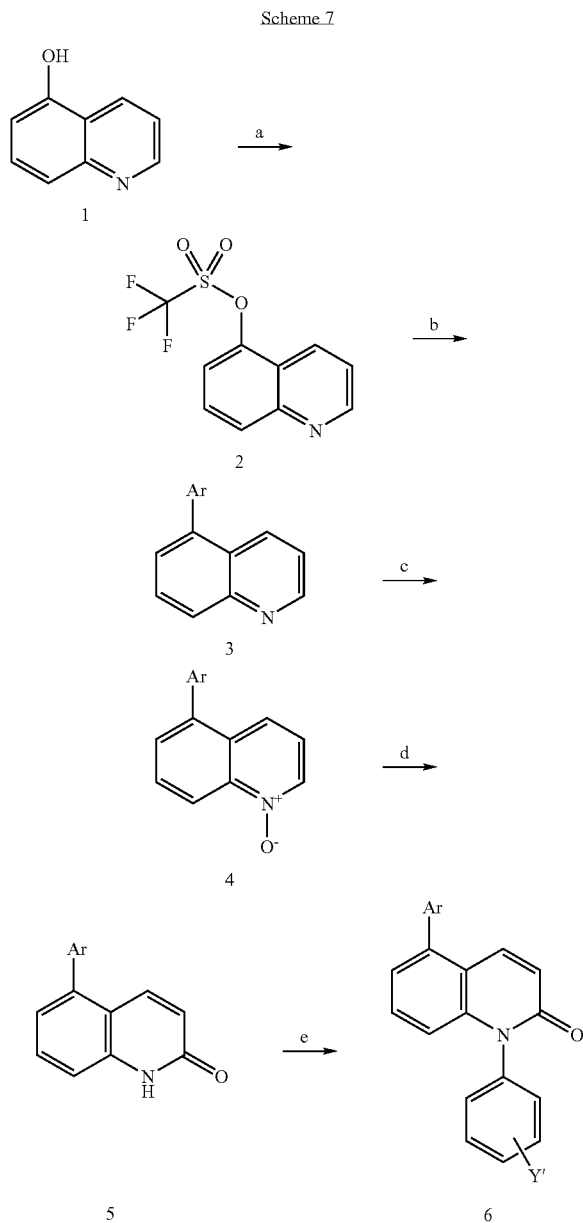

a, (CF$_3$SO$_2$)$_2$O/CH$_2$Cl$_2$/pyridine; b, ArB(OH)$_2$/(Ph$_3$P)$_4$Pd/aq. K$_2$CO$_3$/1,4-dioxane; c, mCPBA/CHCl$_3$; d, tosylchloride/CHCl$_3$/aq. K$_2$CO$_3$; e, 4-fluorophenylboronic acid/powdered 4 Å sieves/Cu(OAc)$_2$/pyridine/Et$_3$N.

The 5-hydroxyquinoline 1-Scheme 7 was triflated with triflic anhydride in pyridine to afford triflate 2-Scheme 7. Compound 1 or related hydroxyquinolines may also be triflated using N-phenyltrifluoromethanesulfonamide or 2-[N, N-bis(trifluoromethylsulfonyl)-amino]-pyridine and related triflating agents. Substitution of the triflate via a palladium catalysed Suzuki reaction with an aryl boronic acid afforded the 5-aryl quinoline 3. Related transformations may also be effected using other substituted quinolin-5-yl halogens or electron deficient sulfonates and coupling of these with diverse organometallics aided by transition metal catalysis as recorded in the literature and utilizing catalysts such as PdCl2 (PPh3)2 (Perkin I, 2000, 2591) or NiCl$_2$(PPh$_3$)$_2$ (Chem Lett, 2001, 976).

N-oxidation with 3-chloroperoxybenzoic acid formed the quinoline N-oxides 4. This transformation may also be achieved using 30% aqueous hydrogen peroxide in acidic acid. Rearrangement using tosyl chloride under basic conditions afforded the 5-substituted quinolinone system 5. This well known quinoline N-oxide rearrangement can also be effected with acylating agents such as benzoyl chloride or acetic anhydride in the presence of aqueous base.

The final products, 6-Scheme 7, were synthesised via a copper acetate mediated arylation of the pyridone nitrogen with arylboronic acids as originally described by Lam and Chan (Tetrahedron Lett 1998, 2941) and extended to pyridones by Mederski and co-workers (Tetrahedron 1999, 12757.) More recently Lam and co-workers extended these procedures to allow the use of catalytic Cu(OAc)$_2$ with in situ reoxidation of the Cu(OAc)$_2$ in the presence of oxidizing agents (Tetrahedron Lett. 2001, 3415.). In addition to coupling with arylboronic acids, such Cu(OAc)2 mediated amide arylations may also be effected using other organometalloids such as hypervalent diaryliodonium salts, aryl siloxanes, arylbismuths or arylstannanes.

Alternatively the arylation step may be effected using Buchwald's procedures for amide arylation with arylbromides, triflates or iodides in the presence of a suitable palladium catalyst and base (Organic Lett. 2000 1101). Ar=optionally substituted aryl for the R$_1$ moiety, and Y' is an optional substituent on the R$_3$ moiety as described herein in the specification.

Methods of Treatment

The compounds of Formula (I) and (Ia) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

For purposes herein, compounds of Formula (I) and (Ia) will all be referred to as compounds of Formula (I) unless otherwise indicated.

Compounds of Formula (I) are capable of inhibiting proinflammatory cytokines, such as IL-1, IL-6, IL-8, and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandin's affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-6, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, meningitis, ischemic and hemorrhagic stroke, neurotrauma/closed head injury, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, gout, traumatic arthritis, rubella arthritis and acute synovitis. Recent evidence also links IL-1 activity to diabetes, pancreatic β cell diseases and Alzheimer's disease.

Use of a CSAID inhibitor compound for the treatment of CSBP mediated disease states, can include, but not be limited to neurodegenerative diseases, such as Alzheimer's disease (as noted above), Parkinson's disease and multiple sclerosis, etc.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, chronic pulmonary inflammatory disease and chronic obstructive pulmonary disease, silicosis, pulmonary sarcoisosis, bone resorption diseases, such as osteoporosis, cardiac, brain and renal reperfusion injury, graft vs. host reaction, allograft rejections, fever and myalgias due to infection, such as influenza, brain infections including encephalitis (including HIV-induced forms), cerebral malaria, meningitis, ischemic and hemorrhagic stroke, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

It is also recognized that both IL-6 and IL-8 are produced during rhinovirus (HRV) infections and contribute to the pathogenesis of common cold and exacerbation of asthma associated with HRV infection (Turner et al. (1998), Clin. Infec. Dis., Vol 26, p 840; Teren et al. (1997), Am J Respir Crit Care Med vol 155, p 1362; Grunberg et al. (1997), Am J Respir Crit Care Med 156:609 and Zhu et al, J Clin Invest (1996), 97:421). It has also been demonstrated in vitro that infection of pulmonary epithelial cells with HRV results in production of IL-6 and IL-8 (Subauste et al., J. Clin. Invest. 1995, 96:549.) Epithelial cells represent the primary site of infection of HRV. Therefore another aspect of the present invention is a method of treatment to reduce inflammation associated with a rhinovirus infection, not necessarily a direct effect on virus itself.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation. Periodontal disease has also been implemented in cytokine production, both topically and systemically. Hence use of compounds of Formula (I) to control the inflammation associated with cytokine production in such peroral diseases such as gingivitis and periodontitis is another aspect of the present invention.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac, brain and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-a) and Tumor Necrosis Factor beta (TNF-$\beta$).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-$\beta$ (also known as lymphotoxin) has close structural homology with TNF-$\square$ (also known as cachectin) and since each induces similar biologic responses and binds to the same cellular receptor, both TNF-$\alpha$ and TNF-$\beta$ are inhibited by the compounds of the present invention and thus are herein referred to collectively as "TNF" unless specifically delineated otherwise.

A member of the MAP kinase family, alternatively termed CSBP, p38, or RK, has been identified independently by several laboratories. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I) have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, congestive heart failure, coronary arterial bypass grafting (CABG) surgery, chronic renal failure, angiogenesis & related processes, such as cancer, thrombosis, glomerulonephritis, diabetes and pancreatic $\square$ cells, multiple sclerosis, muscle degeneration, eczema, psoriasis, sunburn, and conjunctivitis are also included.

The CSBP inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406-1412; Badger, et al., (1989) *Circ. Shock* 27, 51-61; Votta et al., (1994) *in vitro. Bone* 15, 533-538; Lee et al., (1993). B *Ann. N.Y. Acad. Sci.* 696, 149-170.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Therefore CSBP kinase inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

Accordingly, the present invention provides a method of treating a CSBP kinase mediated disease in a mammal in need thereof, preferably a human, which comprises administering to said mammal, an effective amount of a compound of Formula (I) or a pharmaceutically acceptable salt thereof.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures.

The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampoule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as siliceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of inhibition of CSBP/p38 or cytokine inhibition or production. In particular, CSBP/p38 mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

Another aspect of the present invention is a method of treating the common cold or respiratory viral infection caused by human rhinovirus (HRV), other enteroviruses, coronavirus, influenza virus, parainfluenza virus, respiratory syncytial virus, or adenovirus in a human in need thereof which method comprises administering to said human an effective amount of a CBSP/p38 inhibitor.

Another aspect of the present invention is a method of treating, including prophylaxis of influenza induced pneumonia in a human in need thereof which method comprises administering to said human an effective amount of a CBSP/p38 inhibitor The present invention also relates to the use of the CSBP/p38 kinase inhibitor for the treatment, including prophylaxis, of inflammation associated with a viral infection of a human rhinovirus (HRV), other enteroviruses, coronavirus, influenza virus, parainfluenza virus, respiratory syncytial virus, or adenovirus.

In particular, the present invention is directed to the treatment of a viral infection in a human, which is caused by the human rhinovirus (HRV), other enterovirus, coronavirus, influenza virus, parainfluenza virus, respiratory syncytial virus, or an adenovirus. In particular the invention is directed to respiratory viral infections that exacerbate asthma (induced by such infections), chronic bronchitis, chronic obstructive pulmonary disease, otitis media, and sinusitis. While inhibiting IL-8 or other cytokines may be beneficial in treating a rhinovirus may be known, the use of an inhibitor of the p38 kinase for treating HRV or other respiratory viral infections causing the common cold is believed novel. It should be noted that the respiratory viral infection treated herein might also be associated with a secondary bacterial infection, such as otitis media, sinusitis, or pneumonia.

For use herein treatment may include prophylaxis for use in a treatment group susceptible to such infections. It may also include reducing the symptoms of, ameliorating the symptoms of, reducing the severity of, reducing the incidence of, or any other change in the condition of the patient, which improves the therapeutic outcome.

It should be noted that the treatment herein is not directed to the elimination or treatment of the viral organism itself but is directed to treatment of the respiratory viral infection that exacerbates other diseases or symptoms of disease, such as asthma (induced by such infections), chronic bronchitis, chronic obstructive pulmonary disease, otitis media, and sinusitis.

A preferred virus for treatment herein is the human rhinovirus infection (HRV) or respiratory syncytial virus (RSV).

The invention will now be described by reference to the following biological examples that are merely illustrative and are not to be construed as a limitation of the scope of the present invention.

BIOLOGICAL EXAMPLES

The cytokine-inhibiting effects of compounds of the present invention may be determined by the following in vitro assays: Assays for Interleukin-1 (IL-1), Interleukin-8 (IL-8), and Tumour Necrosis Factor (TNF) are well known in the art, and may be found in a number of publications, and patents. Representative suitable assays for use herein are described in Adams et al., U.S. Pat. No. 5,593,992, whose disclosure is incorporated by reference in its entirety.

Interleukin-1 (IL-1)

Human peripheral blood monocytes are isolated and purified from either fresh blood preparations from volunteer donors, or from blood bank buffy coats, according to the procedure of Colotta et al, J Immunol, 132, 936 (1984). These monocytes ($1 \times 10^6$) are plated in 24-well plates at a concentration of 1-2 million/ml per well. The cells are allowed to adhere for 2 hours, after which time non-adherent cells are removed by gentle washing. Test compounds are then added to the cells for 1 h before the addition of lipopolysaccharide (50 ng/ml), and the cultures are incubated at 37° C. for an additional 24 h. At the end of this period, culture supernatants are removed and clarified of cells and all debris. Culture supernatants are then immediately assayed for IL-1 biological activity, either by the method of Simon et al., J. Immunol. Methods, 84, 85, (1985) (based on ability of IL-1 to stimulate a Interleukin 2 producing cell line (EL-4) to secrete IL-2, in concert with A23187 ionophore) or the method of Lee et al., J. Immuno Therapy, 6 (1), 1-12 (1990) (ELISA assay).

In Vivo TNF Assay:
(1) Griswold et al., *Drugs Under Exp. and Clinical Res., XIX* (6), 243-248 (1993); or
(2) Boehm, et al., *Journal Of Medicinal Chemistry* 39, 3929-3937 (1996) whose disclosures are incorporated by reference herein in their entirety.

LPS-Induced TNFα Production in Mice and Rats

In order to evaluate in vivo inhibition of LPS-induced TNFα production in rodents, both mice and rats are injected with LPS.

Mouse Method

Male Balb/c mice from Charles River Laboratories are pretreated (30 minutes) with compound or vehicle. After the 30 min. pretreat time, the mice are given LPS (lipopolysaccharide from *Esherichia coil* Serotype 055-85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at −20° C. until assayed for TNFα by ELISA.

Rat Method

Male Lewis rats from Charles River Laboratories are pretreated at various times with compound or vehicle. After a determined pretreat time, the rats are given LPS (lipopolysaccharide from Esherichia coli Serotype 055-85, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels were measured using a sandwich ELISA, as described in Olivera et al., Circ. Shock, 37, 301-306, (1992), whose disclosure is incorporated by reference in its entirety herein, using a hamster monoclonal antimurine TNFα (Genzyme, Boston, Mass.) as the capture antibody and a polyclonal rabbit antimurine TNFa (Genzyme) as the second antibody. For detection, a peroxidase-conjugated goat antirabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production in Human Whole Blood

Assay: Test compound concentrations were prepared at 10× concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes containing compounds and LPS in 0.4 mL volumes and the tubes incubated at 37 C. Following a 4 hour incubation, the tubes were centrifuged at 5000 rpm for 5 minutes in a TOMY microfuge, plasma was withdrawn and frozen at −80 C.

Cytokine measurement: IL-I and/or TNF were quantified using a standardized ELISA technology. An in-house ELISA kit was used to detect human IL-1 and TNF. Concentrations of IL-1 or TNF were determined from standard curves of the appropriate cytokine and IC50 values for test compound (concentration that inhibited 50% of LPS-stimulated cytokine production) were calculated by linear regression analysis.

CSBP/p38 Kinase Assay:

This assay measures the CSBP/p38-catalyzed transfer of $^{32}P$ from [a-$^{32}P$]ATP to threonine residue in an epidermal growth factor receptor (EGFR)-derived peptide (T669) with the following sequence: KRELVEPLTPSGEAPNQALLR (SEQ ID 1) (residues 661-681). (See Gallagher et al., "Regulation of Stress Induced Cytokine Production by Pyridinyl Imidazoles: Inhibition of CSBP Kinase", BioOrganic & Medicinal Chemistry, 1997, 5, 49-64).

Reactions are carried in round bottom 96 well plate (from Corning) in a 30 ml volume. Reactions contain (in final concentration): 25 mM Hepes, pH 7.5; 8 mM $MgCl_2$; 0.17 mM ATP (the $Km_{[ATP]}$ of p38 (see Lee et al., Nature 300, n72 pg. 639-746 (December 1994)); 2.5 uCi of [g-32P]ATP; 0.2 mM sodium orthovanadate; 1 mM DTT; 0.1% BSA; 10% glycerol; 0.67 mM T669 peptide; and 2-4 nM of yeast-expressed, activated and purified p38. Reactions are initiated by the addition of [gamma-32P]Mg/ATP, and incubated for 25 min. at 37° C. Inhibitors (dissolved in DMSO) are incubated with the reaction mixture on ice for 30 minutes prior to adding the 32P-ATP. Final DMSO concentration was 0.16%. Reactions are terminated by adding 10 ul of 0.3 M phosphoric acid, and phosphorylated peptide was isolated from the reactions by capturing it on p81 phosphocellulose filters. Filters are washed with 75 mM phosphoric acids, and incorporated 32P was quantified using beta scintillation counter. Under these conditions, the specific activity of p38 will be determined and is generally 400-450 pmol/pmol enzyme, and the activity being linear for up to 2 hours of incubation. The kinase activity values are obtained after subtracting values generated in the absence of substrate which were 10-15% of total values.

Examples 11 and 12 demonstrated significantly less activity in this assay in comparison to Examples 9 and 10, however they are deemed to be active inhibitors within the context of this invention. For example, the compound of Example 9 demonstrated an IC50 in uM of 0.06; Example 10 demonstrated an IC50 of 0.2 uM; Example 11 an IC50 of 5 uM and Example 12 an IC50 of 13.35.

TNF-α in Traumatic Brain Injury Assay

This assay provides for examination of the expression of tumor necrosis factor mRNA in specific brain regions, which follow experimentally, induced lateral fluid-percussion traumatic brain injury (TBI) in rats. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma. A suitable assay may be found in WO 97/35856 whose disclosure is incorporated herein by reference.

CNS Injury Model for IL-1β mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay:

Described in WO 97/32583, whose disclosure is incorporated herein by reference, is an assay for determination of inflammatory angiogenesis that may be used to show that cytokine inhibition will stop the tissue destruction of excessive or inappropriate proliferation of blood vessels.

Rhinovirus/Influenza Assay:

Cell lines, rhinovirus serotype 39, and influenza virus A/PR/8/34 were purchased from American Type Culture Collection (ATCC). BEAS-2B cells were cultured according to instructions provided by ATCC using BEGM (bronchial epithelial growth media) purchased from Clonetics Corp. HELA cell cultures, used for detection and titration of virus, were maintained in Eagle's minimum essential media containing 10% fetal calf serum, 2 mM l-glutamine, and 10 mM HEPES buffer (MEM).

A modification of the method reported by Subauste et al., Supra, for in vitro infection of human bronchial epithelial cells with rhinovirus was used in these studies. BEAS-2B cells ($2\times10^5$/well) were cultured in collagen-coated wells for 24 hours prior to infection with rhinovirus. Rhinovirus serotype 39 was added to cell cultures for one hour incubation at 34° C. after which inoculum was replaced with fresh media and cultures were incubated for an additional 72 hours at 34° C. Supernatants collected at 72 hours post-infection were assayed for cytokine protein concentration by ELISA using commercially available kits (R&D Systems). Virus yield was also determined from culture supernatants using a microtitration assay in HELA cell cultures (Subauste et al., supra 1995). In cultures treated with p38 kinase inhibitors, drug was added 30 minutes prior to infection. Stocks of compounds were prepared in DMSO (10 mM drug) and stored at −20° C.

For detection of p38 kinase, cultures were incubated in basal media without growth factors and additives to reduce endogenous levels of activated p38 kinase. Cells were harvested at various timepoints after addition of rhinovirus. Detection of tyrosine phosphorylated p38 kinase by immunoblot was analyzed by a commercially available kit and was performed according to the manufacturer's instructions (PhosphoPlus p38 MAPK Antibody Kit: New England BioLabs Inc.).

In some experiments, BEAS-2B cells were infected with influenza virus (strain A/PR/8/34) in place of rhinovirus. Culture supernatant was harvested 48 and 72 hour post-infection and tested by ELISA for cytokine as described above.

Cells and Virus: Influenza A/PR/8/34 sub type H1N1 (VR-95 American Type Culture Collection, Rockville, Md.) was grown in the allantoic cavity of 10 day old chicken eggs. Following incubation at 37° C., and refrigeration for 2½ hours at 4° C., allantoic fluid was harvested, pooled, and centrifuged (1,000 rcf; 15 min; 4° C.) to remove cells. Supernatant was aliquoted and stored at −70° C. The titer of the stock culture of virus was $1.0\times10^{10}$ Tissue Culture Infective Dose/ml ($TCID_{50}$)

Inoculation procedure: Four-six week old female Balb/cAnNcrlBr mice were obtained from Charles River, Raleigh, N.C. Animals were infected intranasally. Mice were anesthetized by intraperitoneal injection of Ketamine (40 mg/kg; Fort Dodge Labs, Fort Dodge, Iowa) and Xylazine (5 mg/kg; Miles, Shawnee Mission, Kans.) and then inoculated with 100 TCID50 of PR8 diluted in PBS in 20 ul. Animals were observed daily for signs of infection. All animal studies were approved by SmithKline Beecham Pharmaceuticals Institutional Animal Care and Use Committee.

Virus titration: At various times post infection, animals were sacrificed and lungs were aseptically harvested. Tissues were homogenized, in vials containing 1 micron glass beads (Biospec Products, Bartlesville, Okla.) and 1 ml. of Eagles minimal essential medium. Cell debris was cleared by centrifugation at 1,000 rcf for 15 minutes at 4° C., nd supernatants were serially diluted on Madin-Darby canine kidney (MDCK) cells. After 5 days of incubation at 37° C. (5% $CO_2$), 50 µl of 0.5% chick red blood cells were added per well, and agglutination was read after 1 hour at room temperature. The virus titer is expressed as 50% tissue culture infective dose ($TCID_{50}$) calculated by logistic regression.

ELISA: Cytokine levels were measured by quantitative ELISA using commercially available kits. Ear samples were homogenized using a tissue minser in PBS. Cell debris was cleared by centrifugation at 14,000 rpm for 5 minutes. The cytokine concentrations and thresholds were determined as described by the manufacturer; IL-6, IFN-γ, and KC (R&D Systems, Minneapolis, Minn.).

Myeloperoxidase Assay: Myeloperoxidase (MPO) activity was determined kinetically as described by Bradley et al. (1982). Briefly, rabbit cornea were homogenized in Hexadecyl Trimethyl-Ammonium Bromide (HTAB) (Sigma Chemical Co. St. Louis, Mo.) which was dissolved in 0.5 m Potassium phosphate buffer (J.T. Baker Scientific, Phillipsburg, N.J.). Following homogenization, the samples were subjected to freeze-thaw-sonication (Cole-Parmer 8853, Cole-Parmer, Vernon Hills, Il) 3 times. Suspensions were then cleared by centrifugation at 12,500×g for 15 minutes at 4° C. MPO enzymatic activity was determined by colormetric change in absorbance during a reaction of O-Dianisidine dihydrochloride (ODI) 0.175 mg/ml (Sigma Chemical Co. St. Louis, Mo.) with 0.0002% Hydrogen peroxide (Sigma Chemical Co. St. Louis, Mo.). Measurements were performed by using a Beckman Du 640 Spectrophotometer (Fullerton, Calif.) fitted with a temperature control device. 50 ul of material to be assayed was added to 950 ul of ODI and change in absorbance was measured at a wave length of 460 nm for 2 minutes at 25° C.

Whole Body Plethysomography: Influenza virus infected mice were placed into a whole body plethysomograph box with an internal volume of approximately 350-ml. A bias airflow of one l/min was applied to the box and flow changes were measured and recorded with a Buxco XA data acquisition and respiratory analysis system (Buxco Electronics, Sharon, Conn.). Animals were allowed to acclimate to the plethysomograph box for 2 min. before airflow data was recorded. Airway measurements were calculated as Penh (enhanced pause). Penh has previously been shown as an index of airway obstruction and correlates with increased intrapleural pressure. The algorithm for Penh calculation is as follows: Penh=[(expiratory time/relaxation time)-1]×(peak expiratory flow/peak inspiratory flow) where relaxation time is the amount of time required for 70% of the tidal volume to be expired.

Determination of arterial oxygen saturation. A Nonin veterinary hand held pulse oximeter 8500V with lingual sensor (Nonin Medical, Inc., Plymouth Minn.) was used to determine daily arterial oxygen saturation % SpO2 as described (Sidwell et al. 1992 Antimicrobial Agents and Chemotherapy 36:473-476).

Additional data and assay modifications may be found in PCT/US00/25386, (WO 01/19322) filed 15 Sep. 2000, whose disclosure is incorporated herein by reference in its entirety.

Fluorescence Anisotropy Kinase Binding Assay

The CSBP kinase enzyme, a fluorescent ligand and a variable concentration of the test compound are incubated together to reach thermodynamic equilibrium under conditions such that in the absence of test compound the fluorescent ligand is significantly (>50%) enzyme bound and in the presence of a sufficient concentration (>10×$K_i$) of a potent inhibitor the anisotropy of the unbound fluorescent ligand is measurably different from the bound value.

The concentration of kinase enzyme should preferably be $\geq 1 \times K_f$. The concentration of fluorescent ligand required will depend on the instrumentation used, and the fluorescent and physicochemical properties. The concentration used must be lower than the concentration of kinase enzyme, and preferably less than half the kinase enzyme concentration.

A typical protocol is:

All components dissolved in Buffer of final composition 62.5 mM HEPES, pH 7.5, 1.25 mM CHAPS, 1.25 mM DUT, 12.5 mM $MgCl_2$ 3.3% DMSO.

p38 Enzyme concentration: 12 nM

Fluorescent ligand concentration: 5 nM

Test compound concentration: 0.1 nM-100 uM

Components incubated in 30 ul final volume in NUNC 384 well black microtitre plate until equilibrium reached (5-30 mins)

Fluorescence anisotropy read in LJL Acquest.

Definitions: $K_i$=dissociation constant for inhibitor binding $K_f$=dissociation constant for fluorescent ligand binding The fluorescent ligand is the following compound:

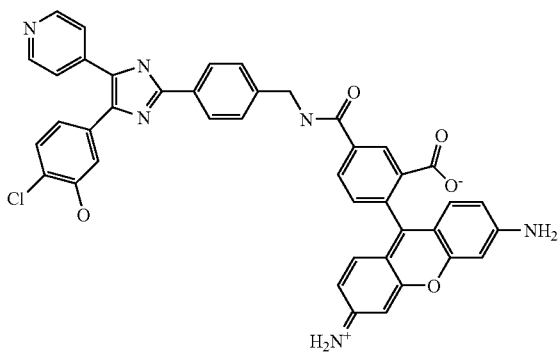

which is derived from 5-[2-(4-aminomethylphenyl)-5-pyridin-4-yl-1H-imidazol-4-yl]-2-chlorophenol and rhodamine green.

Representative compounds of Formula (I) and (Ia) were tested in this assay. Examples 3 to 7 demonstrated a pKi between 7.8 and 8.8. pKi in this assay is the negative log of the Ki term as determined herein.

Examples 12 to 14, and 18 to 20 all demonstrated positive IC50's in this assay, and all are less than 1 micromolar in activity. Examples 2, 8, 9, 15(g), Example 17 as two conformational isomers exhibited a pKi in this assay of 7.7 and 7.9 respectively; and Examples 21, 23 and 24 were not tested in this assay.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and reactions were run under anhydrous conditions in an Argon (Ar) atmosphere where necessary.

$^1$H-NMR (hereinafter "NMR") spectra were recorded at 400 MHz using a Bruker AM 400 spectrometer or a Bruker AVANCE 400. Multiplicities indicated are: s=singlet, d=doublet, t=triplet, q=quartet, m=multiplet and br indicates a broad signal. Flash chromatography was run over Merck Silica gel 60 (230-400 mesh) or equivalent in solvent mixtures as described in each experiment.

satd=saturated; aq=aqueous; NMP=1-methyl-2-pyrrolidinone; DDQ=2,3-dichloro-5,6-dicyano-1,4-benzoquinone; SPE=solid phase extraction; other abbreviations are as described in the ACS Style Guide (American Chemical Society, Washington, D.C., 1986).

General Procedures:

A) LC/MS (Liquid Chromatography/Mass Spectroscopy)

Waters ZQ mass spectrometer operating in positive ion electrospray mode, mass range 100-1000 amu.

UV wavelength: 215-330 nM

Column: 3.3 cm×4.6 mm ID, 3 μm ABZ+PLUS

Flow Rate: 3 ml/min

Injection Volume: 5 μl

Solvent A: 95% acetonitrile+0.05% formic acid

Solvent B: 0.1% formic acid+10 mM ammonium acetate

Gradient: 0% A/0.7 min, 0-100% A/3.5 min, 100% A/1.1 min, 100-0% A/0.2 min

B) Mass Directed Automated Preparative HPLC Column, Conditions and Eluent

The preparative column used was a Supelcosil ABZplus (10 cm×2.12 cm internal diameter; particle size 5 μm)

UV detection wavelength: 200-320 nM

Flow rate: 20 ml/min

Injection Volume: 0.5 ml

Solvent A: 0.1% formic acid

Solvent B: 95% acetonitrile+0.05% formic acid

Using the synthesis as shown in Scheme 1 the following intermediate and final compounds of Formula (I) as herein described have been made:

Compounds of Formula (I) and (Ia):

Example 1

7-Bromo-1,5-bis(2-chlorophenyl)-3,4-dihydro[1,6]naphthyridin-2(1H)-one

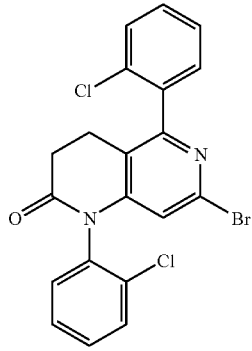

1a) 4,6-Dibromo-3-(bromomethyl)-2-(2-chlorophenyl)pyridine

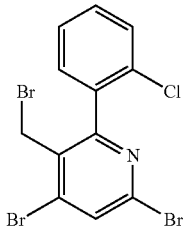

Preparation of the title compound was synthesized as described in WO 02/058695 whose disclosure is incorporated herein by reference in its entirety.

1b) Tert-butyl 3-[4,6-Dibromo-2-(2-chlorophenyl)-3-pyridyl]propionate

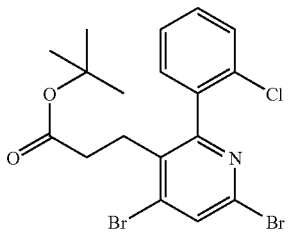

n-Butyllithium in hexanes (1.6 Molar (hereinafter "M"), 3.75 millilitre (hereinafter "ml"), 6.0 millimole (hereinafter "mmol")) was added to di-isopropylamine (0.84 ml, 6.0 mmol) in dry THF (15 ml) at −10° under nitrogen. After 5 minutes (hereinafter "min"). the solution was cooled to −70° and tert-butyl acetate (0.5 ml, 3.71 mmol) added dropwise. After stirring at −70° C. for 10 min. under nitrogen, 4,6-Dibromo-3-(bromomethyl)-2-(2-chlorophenyl)pyridine (0.405 grams (hereinafter "g"), 0.92 mmol) in dry THF (15 ml) was added, and the mixture stirred at −70° for 2 h. Glacial acetic acid (2 ml) was added, the temperature allowed to rise to 22° and the solution evaporated in vacuo. The residue was purified by column chromatography over silica (50 g) eluting with cyclohexane-ethyl acetate (9:1)-(5:1) to give the product as an oil (0.21 g).

NMR: (400 MHz, CDCl$_3$) δ 7.75 (1H,s), 7.48-7.25(4H,3×m), 2.94, 2.75 (2H,2×m), 2.38, 2.22(2H, 2×m), 1.36 (9H,s).

LC/MS R$_t$ 3.91 min m/z 474/6/8 [MH$^+$]

1c) 3-[4,6-Dibromo-2-(2-chlorophenyl)-3-pyridyl]propionic acid

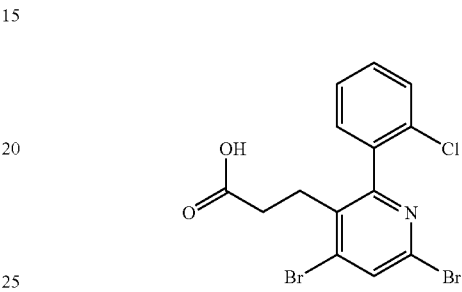

Tert-butyl 3-[4,6-Dibromo-2-(2-chlorophenyl)-3-pyridyl]propionate (3.86 g, 8.116 mmol) was dissolved in trifluoroacetic acid-water (9:1, 25 ml) and the solution allowed to stand for 3 about hours (hereinafter "h), then evaporated in vacuo. The residue was purified by column chromatography over silica (70 g) eluting with cyclohexane-ethyl acetate (5:1)-(3:1) to give the product as an gum (1.39 g).

NMR (400 MHz, CDCl$_3$) δ 9.85 (1H,br s), 7.78 (1H,s), 7.46 (1H,dd), 7.38 (1H,dt), 7.32 (1H,dt), 7.27 (1H,dd), 2.97, 2.80 (2H,2×m), 2.52, 2.39 (2H,2×m).

1d) N-(2-Chlorophenyl)-3-[4,6-dibromo-2-(2-chlorophenyl)-3-pyridinyl]propanamide

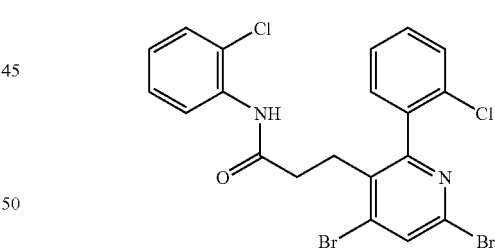

3-[4,6-Dibromo-2-(2-chlorophenyl)-3-pyridyl]propionic acid (1.09 g, 2.603 mmol) was dissolved in toluene (25 ml)-methanol (5 ml), and a 2M solution of trimethylsilyl-diazomethane in hexanes added (5 ml), and the solution allowed to stand for about 0.5 hours. The solution was evaporated in vacuo, and the resulting oil re-dissolved in dichloromethane (25 ml). This solution was added slowly at 22° to a trimethylaluminium-2-chloroaniline complex [prepared by adding 2M trimethylaluminium in toluene (2.6 ml) to a solution of 2-chloroaniline (0.55 ml, 5.188 mmol) in dichloromethane (30 ml)] and the solution stirred at 22° for 20 h under nitrogen. Water (15 ml) was added (very slowly at first), followed by sufficient 2M hydrochloric acid to dissolve all the precipitated aluminium salts. The organic phase was separated and the aqueous phase further extracted with dichloromethane (60 ml). The combined organic extracts were dried (Na₂SO₄), evaporated in vacuo, and the oily residue purified by column chromatography over silica (50 g) eluting with cyclohexane ethyl acetate (100:0-70:30) to afford the title compound as a gum (0.95 g, 69%).

NMR (400 MHz, CDCl₃) δ 8.30 (1H,br d) 7.79 (1H,s), 7.52-7.20 (7H,m), 7.02 (1H,br t), 3.13-2.93 (2H,2×m), and 2.65-2.43 (2H,2×m).

LC/MS $R_t$ 3.81 min m/z 527/529/531/533 [MH⁺]

1e) 7-Bromo-1,5-bis(2-chlorophenyl)-3,4-dihydro[1,6]naphthyridin-2(1H)-one

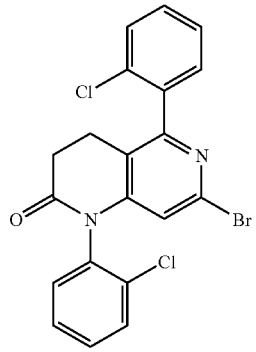

N-(2-Chlorophenyl)-3-[4,6-dibromo-2-(2-chlorophenyl)-3-pyridinyl]propanamide (942 mg, 1.78 mmol) was divided into six portions and each dissolved in DMF (3 ml), and treated with potassium carbonate (50 mg, 0.362 mmol) and copper(I) iodide (15 mg, 0.079 mmol), and heated in a Smith Creator microwave at 180° for 15 min. All reactions were then combined and evaporated in vacuo. The residue was treated with water (15 ml) and extracted with dichloromethane (2×20 ml). The extracts were passed through a hydrophobic frit and evaporated in vacuo. The residue was purified by column chromatography over silica (20 g) eluting with a cyclohexane-ethyl acetate gradient (100:0-0:100). (70:30) gave the product as a white foam (406 mg, 51%).

NMR (400 MHz, CDCl3) δ 7.67-7.63 (1H,m), 7.53-7.30 (7H,m), 6.32 (1H,s), 3.05-2.68 (4H,2×m).

LC/MS $R_t$ 3.55 min m/z 447/449/451 [MH⁺]

Example 2

7-Bromo-1,5-bis(2-chlorophenyl)[1,6]naphthyridin-2(1H)-one

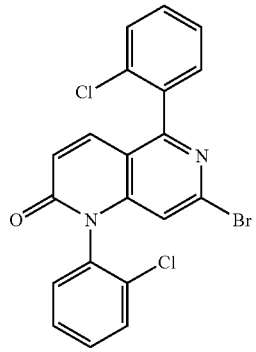

7-Bromo-1,5-bis(2-chlorophenyl)-3,4-dihydro[1,6]naphthyridin-2(1H)-one (30 mg, 0.067 mmol) in carbon tetrachloride (5 ml) was treated with NBS (15 mg) and AlBN (1.1 mg) and heated under reflux for 1.5 h. DBU (10 μl) was added, the mixture cooled, and dichloromethane (5 ml) added, followed by 8% sodium bicarbonate (10 ml). The mixture was passed through a hydrophobic frit and evaporated in vacuo to give the product as an off-white solid.

NMR (400 MHz, CDCl3) δ 7.75-7.69 (1H,m), 7.60-7.33 (8H,m), 6.75 (1H,d), 6.65 (1H,s)

LC/MS $R_t$ 3.50 min m/z 445/447/449 [MH⁺]

Example 3

1,5-Bis(2-Chlorophenyl)-7-[(2-hydroxy-1-(hydroxymethyl)ethyl]-amino][1,6]naphthyridin-2(1H)-one

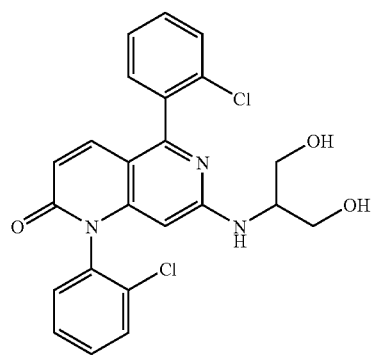

7-Bromo-1,5-bis(2-chlorophenyl)[1,6]naphthyridin-2(1H)-one (38 mg, 0.085 mmol) was dissolved in NMP (2 ml) and serinol (2-amino-1,3-propanediol) (35 mg, 0.384 mmol) added, and the solution heated in a Smith creator microwave at 220° for 0.5 h. After cooling, the solution was added to water (12 ml) and extracted with dichloromethane (10 ml). The mixture was passed through a hydrophobic frit and evaporated in vacuo. The residue was purified by SPE (SiO₂, 10 g) eluting with dichloromethane-methanol (98:2) to afford the title compound as a gum (9 mg, 23%).

NMR (400 MHz, CDCl3) δ 7.69-7.65 (1H,m), 7.55-7.30 (8H,m), 6.37 (1H,d), 5.43 (1H,s), 5.30 (1H,br d), 3.90 (1H, m), 3.80-3.68 (4H,m), 1.63 (2H,br s).

LC/MS $R_t$ 2.84 min m/z 456/458 [MH⁺]

Example 4

N-[2-[[1,5-bis(2-Chlorophenyl)-2-oxo-1,2-dihydro[1,6]naphthyridin-7-yl]amino]ethyl]acetamide

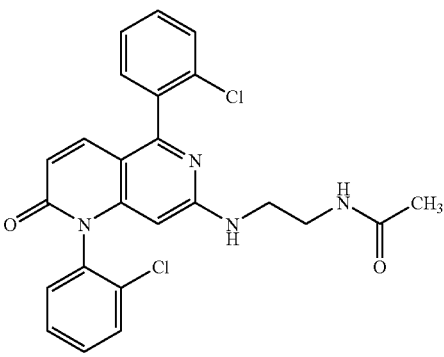

7-Bromo-1,5-bis(2-chlorophenyl)[1,6]naphthyridin-2 (1H)-one (38 mg, 0.085 mmol) was dissolved in NMP (2 ml) and N-acetylethylenediamine (300 mg, 2.938 mmol) added, and the solution heated in a Smith creator microwave at 220° for about 0.5 h. The NMP was removed using a vacuum centrifuge and the residue partitioned between 8% sodium bicarbonate (6 ml) and dichloromethane (10 ml). The mixture was passed through a hydrophobic frit and evaporated in vacuo. The residue was purified by column chromatography over silica (10 g) eluting with ethyl acetate and ethyl acetate-methanol (9:1) to afford crude product. This was further purified by chromatography over SCX-2 silica (0.5 g). Methanol eluted impurities, and 2M ammonia in methanol gave the product as a white solid (12.7 mg, 32%).

NMR (400 MHz, CDCl3) δ 7.68 (1H,m), 7.58-7.37 (7H, m), 7.33 (1H,m), 6.65 (1H,br s), 6.38 (1H,d), 5.35 (1H,s), 5.14 (1H,br t), 3.47-3.28 (4H,m), 1.73 (3H,s).

LC/MS $R_t$ 2.96 min m/z 467/469 [MH$^+$]

Example 5

1,5-Bis(2-Chlorophenyl)-7-[(1H-imidazol-2-ylm-ethyl)amino[1,6]naphthyridin-2(1H)-one, formate salt

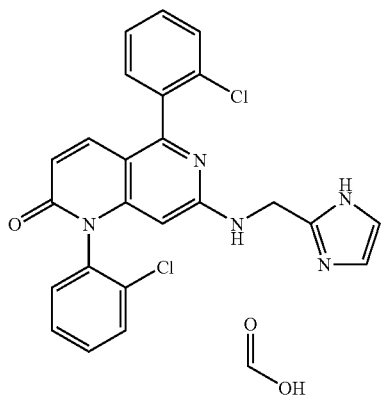

7-Bromo-1,5-bis(2-chlorophenyl)[1,6]naphthyridin-2 (1H)-one (150 mg, 0.336 mmol) was dissolved in NMP (5 ml), and 2-aminomethylimidazole dihydrochloride (286 mg, 1.682 mmol) and potassium carbonate (280 mg, 2.026 mmol) added and the mixture heated in a Smith creator microwave at 220° for about 0.5 h. The mixture was added to water and extracted with dichloromethane (1×10 ml, 1×5 ml), and the dichloromethane extracts passed down a hydrophobic frit, and evaporated in vacuo. The crude residue was passed down an SCX-2 cartridge (5 g), eluting with methanol, followed by 2M ammonia in methanol to elute the crude product. This was purified by mass directed autoprep to afford the product as a gum (5.5 mg, 3.5%).

NMR (400 MHz, MeOH-d$^4$) δ 8.32 (>1H, s), 7.75-7.68 (1H,m), 7.64-7.35 (7H,m), 7.31 (1H,ddd), 7.12 (2H,s), 6.33 (1H,d), 5.63 (1H,s), 4.60 (2H,s).

LC/MS $R_t$ 2.41 min m/z 462/464 [MH$^+$]

Example 6

1,5-Bis(2-Chlorophenyl)-7-[[2-(Isopropylamino) ethyl]amino[1,6]naphthyridin-2(1H)-one, formate salt

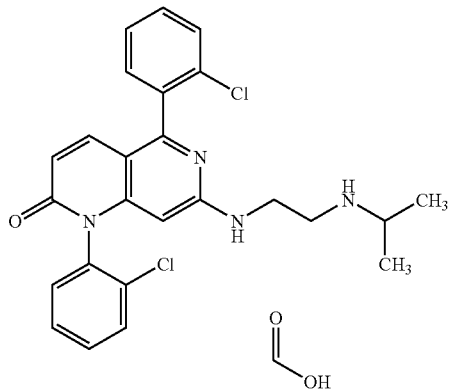

7-Bromo-1,5-bis(2-chlorophenyl)[1,6]naphthyridin-2 (1H)-one (59 mg, 0.132 mmol) was dissolved in NMP (2 ml), and N-isopropylethylenediamine (0.2 ml, 1.603 mmol) added and the mixture heated in a Smith creator microwave at 220° for 0.5 h. The crude reaction mixture was passed down an SCX-2 cartridge (20 g) eluting initially with methanol, followed by 2M ammonia in methanol to elute the crude product. This was purified by mass directed autoprep (per general procedure B) to afford the product as a gum (12.6 mg, 19%).

NMR (400 MHz, MeOH-d$^4$) δ 8.33 (1H,s), 7.78-7.72 (1H, m), 7.67-7.40 (8H,m), 6.36 (1H,dd), 5.68 (1H,br s), 3.72-3.50 (2H,m), 3.26 (1H,m), 3.20-3.10 (2H,m), 1.10 (6H,2×d).

LC/MS $R_t$ 2.53 min m/z 467/469 [MH$^+$]

Example 7

1,5-Bis(2-Chlorophenyl)-7-yl-amino-1,6]naphthyridin-2(1H)-one

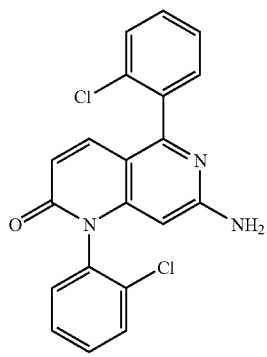

7-Bromo-1,5-bis(2-chlorophenyl)[1,6]naphthyridin-2 (1H)-one reacted with 2M amonia in MeOH to afford the title compound.

LC/MS $R_t$ 3.00 min m/z 382/384 [MH$^+$]

Example 8

1,5-Bis(2-Chlorophenyl)-7-chloro-[1,6]naphthyridin-2(1H)-one

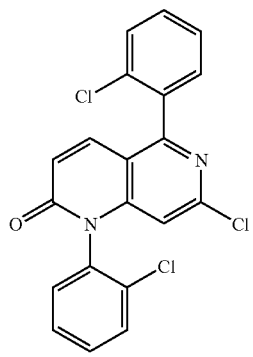

7-Bromo-1,5-bis(2-chlorophenyl)[1,6]naphthyridin-2 (1H)-one dissolved in NMP reacted with chloride ion in a Smith creator microwave at 220° for about 30 minutes. Isolation by the method of example 5 afforded the title compound.

LC/MS R$_t$ 3.49 min m/z 401/403/405 [MH$^+$]

Using the synthesis as shown in Scheme 2, the following intermediate and final compounds of Formula (I, X═H) as herein described have been made:

Example 9

1-Benzyl-5-phenyl-1H-[1,6]naphthyridin-2-one

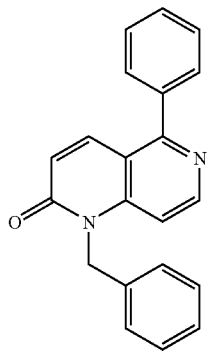

5-Phenyl-1H-[1,6]naphthyridin-2-one was prepared in accordance with the disclosure of Lesher et. al., in U.S. Pat. No. 4,560,691 whose disclosure is incorporated by reference herein (0.111 g, 0.5 mmol), and was dissolved in DMF (2 mL) and stirred under argon. Potassium carbonate (0.066 g, 0.5 mmol) was added, and the mixture heated in an oil bath to 100° C. for 1 hour. Benzyl bromide (0.086 g, 0.5 mmol) was added, and the heating was continued for 6 hours. The solvent was removed in vacuo, and the residue was purified by preparative hplc. After evaporation of the fractions containing the desired product, the residue was partitioned between ethyl acetate and 5% K$_2$CO$_3$, the organic phase was washed with water, brine, dried over anhydrous Na$_2$SO$_4$, filtered, and evaporated to give the product which was then recrystallized from methylene chloride/hexane to give the title compound as a white crystalline solid. mp 101-102° C.

Example 10

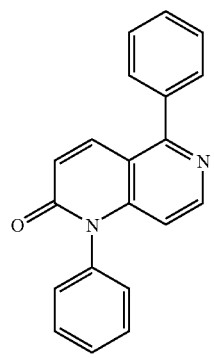

1,5-Diphenyl-1H-[1,6]naphthyridin-2-one

5-Phenyl-1H-[1,6]naphthyridin-2-one was prepared in accordance with the disclosure of Lesher et. al., in U.S. Pat. No. 4,560,691 whose disclosure is incorporated by reference herein (0.111 g, 0.5 mmol) and was dissolved in CH$_2$Cl$_2$ (5 mL) and stirred under argon. Phenyl boronic acid (0.376 g, 3.0 mmol), triethylamine (0.42 mL, 3 mmol), and cupric acetate (0.362 g, 2 mmol0 was added, and the mixture stirred under argon at room temperature for 3 weeks. The solvent was removed in vacuo, and the residue was partitioned between ethyl acetate and water, the organic phase was washed with water, brine, dried over anhydrous Na$_2$SO$_4$, filtered, and evaporated to give the product which was then flash chromatographed with ethyl acetate/hexane to give the title compound as a tan amorphous solid. mp 196-197° C.

Example 11

1-Methyl-5-phenyl-1H-[1,6]naphthyridin-2-one

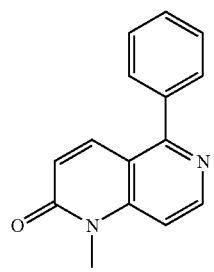

The title compound was prepared in accordance with the disclosure of Lesher et. al., in U.S. Pat. No. 4,560,691 whose disclosure is incorporated by reference herein.

Example 12

5-Phenyl-1H-[1,6]naphthyridin-2-one

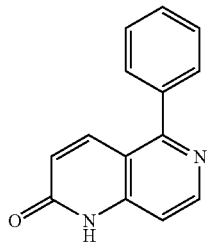

The title compound was prepared in accordance with the disclosure of Lesher et. al., in U.S. Pat. No. 4,560,691 whose disclosure is incorporated by reference herein. Using the synthesis as shown in Scheme 4, the following intermediate and final compounds of Formula (I, X=H) as herein described have been made:

Example 13

1,5-bis(4-fluorophenyl)[1,8]naphthyridin-2(1H)-one

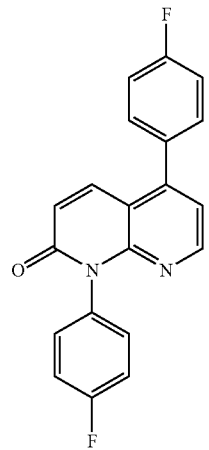

13a)
N-(4-chloro-2-pyridinyl)-2,2-dimethylpropanamide

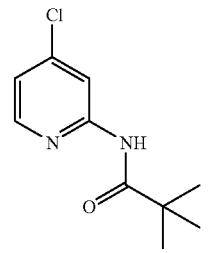

Triethylamine (6.8 mL, 48.6 mmol) was added to a stirred solution of 4-chloro-2-aminopyridine, 11, (Townsend, L. B. et al *Synthetic Commun.* 1997 27, 861-870) (5 g, 38.9 mmol) in dichloromethane (75 mL). After cooling to 0° C. a solution of trimethylacetyl chloride (5.3 mL, 42.8 mmol) in dichloromethane (10 mL) was added dropwise over 15 min. The mixture was allowed to warm to 23° and stirred for 18 h then washed with saturated sodium bicarbonate. The organic layer was dried ($Na_2SO_4$) and evaporated in vacuo to give an off-white solid. This was recrystallised from isopropyl ether to afford the title compound as white crystals (5.5 g, 67%). MS(EI) m/e 213, 215 [M+H]$^+$.

13b) N-(4-chloro-3-formyl-2-pyridinyl)-2,2-dimethylpropanamide

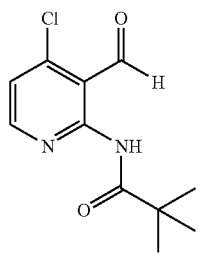

A stirred solution of the compound of Example 13(a) (4 g, 18.8 mmol) in anhydrous tetrahydrofuran (40 mL) under a nitrogen atmosphere was cooled to −78° C. A 1.6M solution of n-butyllithium in hexanes (29.4 mL, 47.0 mmol) was added dropwise over 20 min. After stirring for a further 30 min a solution of anhydrous dimethylformamide (4.4 mL, 56.4 mmol) in anhydrous tetrahydrofuran (10 mL) was added dropwise over 10 min. After stirring at −78° C. for 1 h the mixture was allowed to warm to 23°. 6M hydrochloric acid (100 mL) was added and stirring continued for 15 min. The organic layer was discarded and the aqueous layer adjusted to pH9-10 by the addition of saturated potassium carbonate. This was extracted with ethyl acetate and the organic extracts were dried ($Na_2SO_4$) and evaporated in vacuo to give a yellow semi-solid. Flash chromatography (silica gel, 1:1 ethyl acetate/petroleum ether) afforded the title compound as a white crystalline solid (4.1 g, 90%). MS(EI) m/e 241, 243 [M+H]$^+$.

13c) tert-butyl 3-{4-chloro-2-[(2,2-dimethylpropanoyl)amino]-3-pyridinyl}-3-hydroxypropanoate

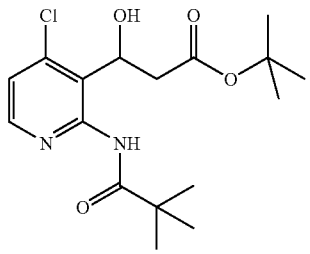

A 1.6M solution of n-butyllithium in hexanes (19.7 mL, 31.5 mmol) was added dropwise to a stirred solution of diisopropylamine (4.4 mL, 31.5 mmol) in anhydrous tetrahydrofuran (30 mL) at −78° C. under a nitrogen atmosphere. After warming to 23° the solution was recooled to −78° C. and a solution of tert-butyl acetate (4.25 mL, 31.5 mmol) in anhydrous tetrahydrofuran (10 mL) was added dropwise. After 15 min a solution of the compound of Example 13(b) (3.61 g, 16 mmol) in anhydrous tetrahydrofuran (15 mL) was added dropwise. The mixture was stirred at −78° C. for 30 min then allowed to warm to 23° and poured into water. This was extracted with ether and the organic extracts were washed with water, dried (Na$_2$SO$_4$) and evaporated in vacuo. The residue was triturated with ether and filtered to afford the title compound as a white solid (3.78 g, 71%).

Flash chromatography of the mother liquor (silica gel, 3:2 ethyl acetate/petroleum ether) afforded a second crop (0.6 g, 11%). MS(EI) m/e 357, 359 [M+H]$^+$.

13d) 5-chloro[1,8]naphthyridin-2(1H)-one

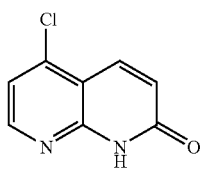

A stirred solution of the compound of Example 13(c) (3.5 g, 9.8 mmol) in 3M hydrochloric acid (40 mL) was refluxed for 2.5 h. After cooling to 23° the mixture was adjusted to pH 8 by the addition of saturated potassium carbonate. This was filtered and the solid washed with water followed by ether then dried in vacuo at 60° C. to afford the title compound as a cream-coloured solid (1.04 g, 59%). MS(EI) m/e 181, 183 [M+H]$^+$.

13e) 5-(4-fluorophenyl)[1,8]naphthyridin-2(1H)-one

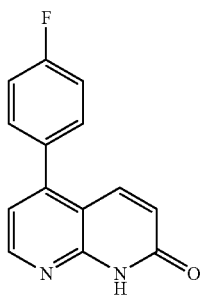

A stirred mixture of the compound of Example 13(d) (0.25 g, 1.38 mmol), 4-fluorophenylboronic acid (0.23 g, 1.66 mmol), tetrakis(triphenylphosphine)palladium(0) (0.08 g, 0.07 mmol) and 2M potassium carbonate (1.87 mL, 3.74 mmol) in ethylene glycol dimethyl ether (5 mL) was refluxed for 24 h. The mixture was diluted with chloroform (200 mL), methanol (75 mL) and 5% sodium carbonate (75 mL) then heated until all solid material had dissolved. The layers were separated and the organic layer was dried (Na$_2$SO$_4$) and evaporated in vacuo. The residue was triturated with methanol and filtered to afford the title compound as a grey solid (0.27 g, 80%). MS(EI) m/e 241 [M+H]$^+$.

13f)
1,5-bis(4-fluorophenyl)[1,8]naphthyridin-2(1H)-one

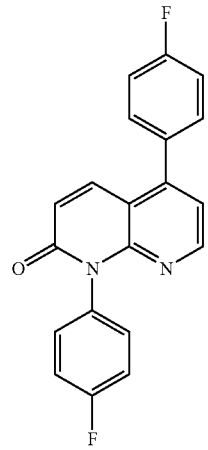

A mixture of the compound of Example 13(e) (0.1 g, 0.42 mmol), 4-fluorophenylboronic acid (0.12 g, 0.83 mmol), triethylamine (0.12 mL, 0.83 mmol), pyridine (0.07 mL, 0.83 mL), copper (II) acetate (0.15 g, 0.83 mmol) and powdered 4 Å sieves in dichloromethane (5 mL) was stirred at RT for 7 h. Further quantities of fluorophenylboronic acid (0.06 g), copper (II) acetate (0.075 g) and powdered 4 Å sieves were added and stirring continued for 18 h. The mixture was retreated as above and stirred for a further 5 h then diluted with dichloromethane (20 mL) and filtered through a pad of celite. The filtrate was washed with saturated sodium carbonate and water, dried (Na$_2$SO$_4$) and evaporated in vacuo to give a brown solid. Flash chromatography (silica gel, 2:1 petroleum ether/ethyl acetate) afforded the title compound as a cream-coloured solid (0.05 g, 36%). MS(EI) m/e 335 [M+H]$^+$. $^1$H NMR(400 MHz, d$_6$-DMSO) δ 8.46 (d, J=5 Hz, 1H), 7.85 (d, J=10 Hz, 1H), 7.56-7.64 (m, 2H), 7.31-7.49 (m, 6H), 7.27 (d, J=5 Hz, 1H), 6.77 (d, J=10 Hz, 1H).

Example 14

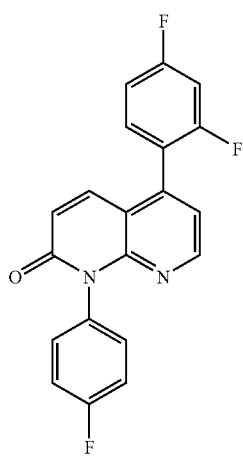

Preparation of 5-(2,4-difluorophenyl)-1-(4-fluorophenyl)[1,8]naphthyridin-2(1H)-one

14a) 5-(2,4-difluorophenyl)[1,8]naphthyridin-2(1H)-one

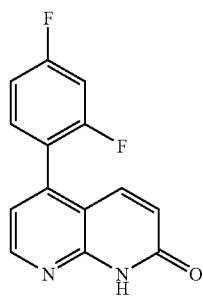

Following the procedure of Example 13(e), except substituting 2,4-difluorophenylboronic acid for 4-fluorophenylboronic acid, the title compound was prepared (0.1 g, 26%). MS(EI) m/e 259 [M+H]+.

14b) 5-(2,4-difluorophenyl)-1-(4-fluorophenyl)[1,8]naphthyridin-2(1H)-one

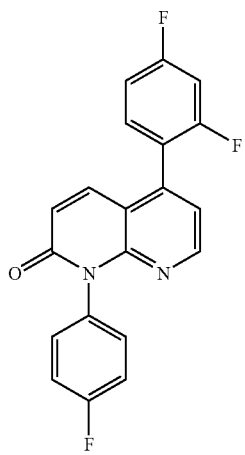

Following the procedure of Example 13(f), except substituting the compound of Example 14(a) for the compound of Example 13(e), the title compound was prepared (0.04 g, 32%). MS(EI) m/e 353 [M+H]+. $^1$H NMR (400 MHz, d$_6$-DMSO) δ 8.50 (d, 1H), 7.50-7.69 (m, 3H), 7.28-7.44 (m, 6H), 6.78 (d, 1H).

Using the synthesis as shown in Scheme 6, the following intermediate and final compounds of Formula (I) as herein described have been made:

Example 15

1,5-Diphenyl-1H-7-[(2-hydroxy-1-(hydroxymethyl)ethyl]-amino]-[1,6]naphthyridin-2-one

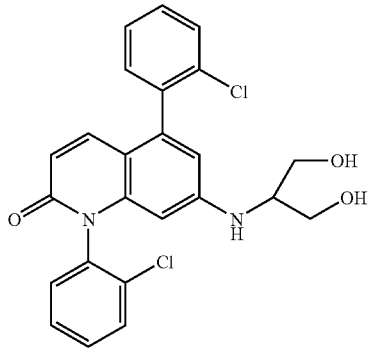

15a) N-(2-chlorophenyl)-3-(2,6-dibromo-4-methoxyphenyl)propanamide

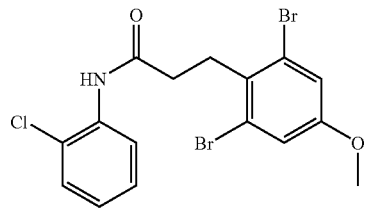

3-(2,6-dibromo-4-methoxyphenyl)propanoic acid (as described in WO 02/058695, whose disclosure is incorporated by reference herein) (6.65 g, 19.67 mmol) was dissolved in chloroform (150 ml) and thionyl chloride (15 ml) added, and the solution heated under reflux for 2 h. The solvent was removed in vacuo and the residue co-evaporated with chloroform (30 ml). The acid chloride so formed was dissolved in chloroform (40 ml) and added dropwise to a solution of 2-chloroaniline (5 ml, 47.53 mmol) and di-isopropyl-ethylamine (10 ml, 57.43 mmol) in chloroform (150 ml) and the solution was allowed to stand at 22° for 17 h. The homogeneous solution washed with 2M hydrochloric acid (100 ml), passed through a hydrophobic frit and the organic phase evaporated in vacuo to give the title compound as a dark solid (7.53 g, 86%)

LC/MS R$_t$ 3.81 min m/z 446/448/450 [MH+]

15b) 5-Bromo-1-(2-chlorophenyl)-7-methoxy-3,4-dihydro-2(1H)-quinolinone

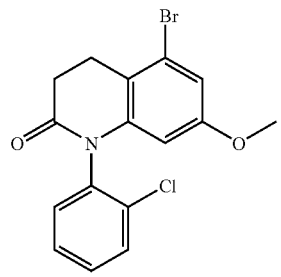

N-(2-chlorophenyl)-3-(2,6-dibromo-4-methoxyphenyl) propanamide (1.40 g, 3.128 mmol), copper(I) iodide (0.895 g, 4.694 mmol), and potassium carbonate (0.865 g, 6.259 mmol) in DMF (15 ml), were heated under reflux for 30 min., cooled and evaporated in vacuo. The residue was treated with 2M hydrochloric acid (80 ml) and extracted with dichloromethane (2×50 ml). The extracts were passed through a hydrophobic frit, evaporated in vacuo and the residue purified by flash chromatography over silica (50 g) eluting with cyclohexane-ethyl acetate gradient (100:0-50:50) to give the product as a white solid (0.714 g, 62%)

LC/MS $R_t$ 3.46 min m/z 366/368/370 [MH$^+$]

15c) 1,5-bis(2-chlorophenyl)-7-methoxy-3,4-dihydro-2(1H)-quinolinone

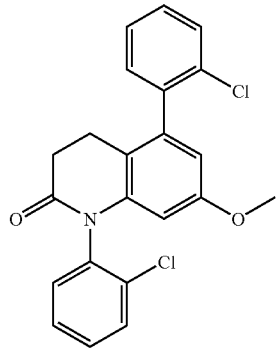

5-Bromo-1-(2-chlorophenyl)-7-methoxy-3,4-dihydro-2 (1H)-quinolinone (2.10 g, 5.728 mmol), and 2-chlorophenylboronic acid (1.77 g, 11.32 mmol) were dissolved in toluene (40 ml)-ethanol (15 ml), and 1M aqueous sodium carbonate (15 ml) added. Nitrogen gas was passed through the mixture for 2 min., then tetrakis(triphenylphosphine)-palladium(0) (0.3 g) added, and the mixture stirred under reflux under nitrogen for 3.5 h. The organic phase was separated, dried (Na$_2$SO$_4$), and evaporated in vacuo and the residue purified by flash chromatography over silica (70 g) eluting with cyclohexane-ethyl acetate gradient to afford the title compound as a white solid (1.98 g, 87%)

LC/MS $R_t$ 3.67 min m/z 398/400 [MH$^+$]

15d) 1,5-bis(2-chlorophenyl)-7-methoxy-2(1H)-quinolinone

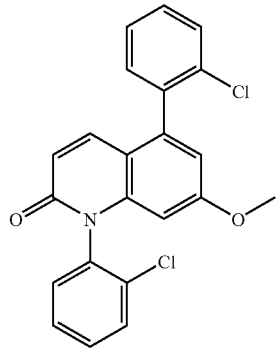

1,5-bis(2-chlorophenyl)-7-methoxy-3,4-dihydro-2(1H)-quinolinone (0.85 g, 2.134 mmol) and manganese dioxide (5 g) were heated in chlorobenzene (50 ml) under reflux for 17 h. After cooling, the chlorobenzene was removed in vacuo, ethyl acetate (80 ml) added to the residue, then filtered through celite. The filtrate was evaporated in vacuo to afford the title compound as a yellow solid (0.82 g, 97%)

LC/MS $R_t$ 3.54 min m/z 396/398/400 [MH$^+$]

15e) 1,5-bis(2-chlorophenyl)-7-hydroxy-2(1H)-quinolinone

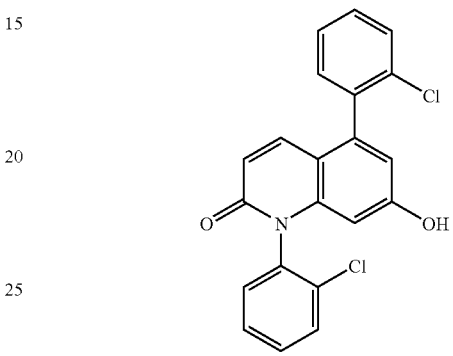

1,5-bis(2-chlorophenyl)-7-methoxy-2(1H)-quinolinone (0.863 g, 2.178 mmol) was dissolved in dichloromethane (40 ml) and 1M boron tribromide in dichloromethane (12 ml) added slowly under nitrogen. The solution was stirred at 21° for 4 h, then quenched carefully with methanol (3 ml) and ice (25 g). The mixture was passed through a hydrophobic frit, and the aqueous phase further extracted with dichloromethane (20 ml), and passed through a hydrophobic frit. The dichloromethane extracts were combined and evaporated in vacuo to afford the title compound as a dark solid (0.784 g, 94%).

LC/MS $R_t$ 3.40 min m/z 382/4 [MH$^+$]

15f) 1,5-bis(2-chlorophenyl)-2-oxo-1,2-dihydro-7-quinolinyl trifluoromethanesulfonate

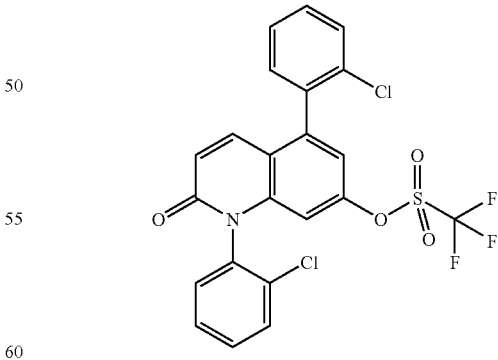

1,5-bis(2-chlorophenyl)-7-hydroxy-2(1H)-quinolinone (0.216 g, 0.565 mmol) and triethylamine (4 ml) were dissolved in dichloromethane (30 ml) and N-phenyltrifluoromethylsulfonimide (0.403 g, 1.128 mmol) added and the resulting solution stirred at 22° for 1 h, and evaporated in vacuo. The residue was purified by flash chromatography over silica (50 g) eluting with cyclohexane-ethyl acetate gradient (100:0-50:50) to afford the title compound as a white solid (0.14 g, 48%).

LC/MS $R_t$ 2.84 min m/z 456/458 [MH$^+$]

15g) 1,5-bis(2-chlorophenyl)-7-{[2-hydroxy-1-(hydroxymethyl)ethyl]amino}-2(1H)-quinolinone

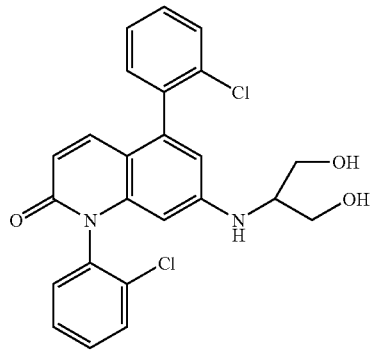

1,5-bis(2-chlorophenyl)-2-oxo-1,2-dihydro-7-quinolinyl trifluoromethanesulfonate (50 mg, 0.097 mmol), serinol (44 mg, 0.483 mmol), racemic BINAP (74 mg, 0.19 mmol), palladium(II) acetate (17 mg, 0.076 mmol), and cesium carbonate (0.14 g, 0.43 mmol) in 1,4-dioxan (2 ml) were heated in a Smith creator microwave at 130° for 15 min. Water (3 ml) and chloroform (4 ml) were added to the reaction mixture, which was then passed through a hydrophobic frit, and blown down under a stream of nitrogen. The residue was purified by mass directed autoprep to afford the title compound as a gum (7 mg, 16%).

LC/MS $R_t$ 2.88 min m/z 455/457 [MH$^+$]

Example 16

1,5-Bis(2-chlorophenyl)-7-{[2-(isopropylamino) ethyl]amino}-2(1H)-quinolinone

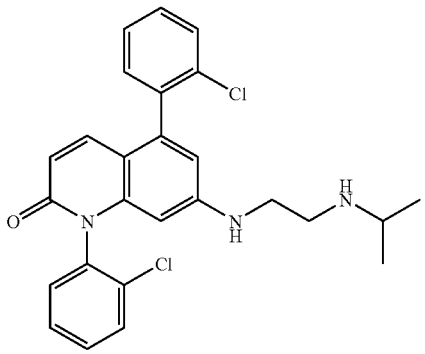

1,5-bis(2-chlorophenyl)-2-oxo-1,2-dihydro-7-quinolinyl trifluoromethanesulfonate (50 mg, 0.097 mmol), N-isopropylethylenediamine (0.36 ml, 2.885 mmol), racemic BINAP (74 mg, 0.119 mmol), palladium(II) acetate (17 mg, 0.076 mmol), and cesium carbonate (0.14 g, 0.43 mmol) in 1,4-dioxan (4 ml) were heated under reflux under nitrogen for 2 h. The solvent was removed in vacuo, and the residue partitioned between water (8 ml) and dichloromethane (10 ml). The mixture was passed through a hydrophobic frit, and the filtrate passed though two 5 g SCX-2 cartridges, and eluted with methanol followed by 2M ammonia in methanol. The latter fractions were evaporated in vacuo and the residue purified by mass directed autoprep (per general procedure B) to afford the title compound as a gum (5.3 mg, 10%).

LC/MS $R_t$ 2.54 min m/z 466/468 [MH$^+$]

Example 17

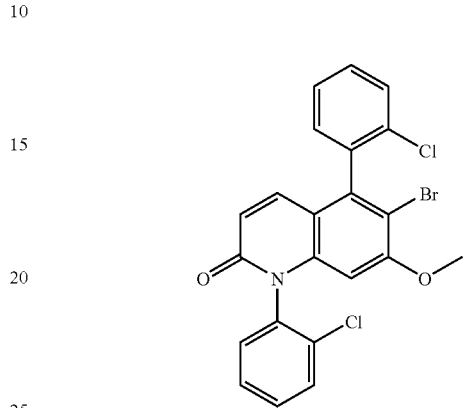

6-bromo-1,5-bis(2-chlorophenyl)-7-(methyloxy)-2 (1H)-quinolinone

The product of example 15(c) was reacted by the procedure of example 2. The cooled reaction mixture was diluted with ethyl acetate (20 ml), and washed with 2M hydrochloric acid (10 ml), dried (Na$_2$SO$_4$) and evaporated in vacuo. The residue was purified by flash chromatography over silica (20 g) eluting with cyclohexane-ethyl acetate (100:0-0:100 gradient) to afford the two isomers of the title compound as white solids.

Isomer 1:
 TLC $R_f$=0.29 (SiO$_2$ cyclohexane-ethyl acetate 1:1)
 LC/MS $R_t$ 3.64 min m/z 474/476/478 [MH$^+$]
Isomer 2:
 TLC $R_f$=0.21 (SiO$_2$ cyclohexane-ethyl acetate 1:1)
 LC/MS $R_t$ 3.65 min m/z 474/476/478 [MH$^+$]

Using the synthesis as shown in Scheme 7, the following intermediate and final compounds of Formula (I, X=H) as herein described have been made:

Example 18

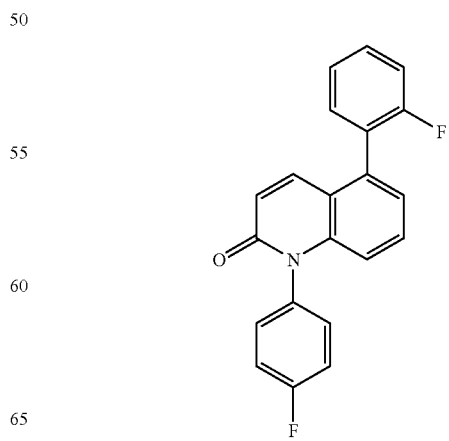

5-(2-fluorophenyl)-1-(4-flourophenyl)-2(1H)-quinolinone 18a) 5-quinolinyl triflouromethanesulfonate

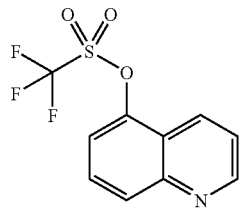

Pyridine (1.67 mL, 20.6 mmol) was added to a stirred suspension of 5-hydroxyquinoline (1.0 g, 6.89 mmol) in CH$_2$Cl$_2$ at 0° C. under an atmosphere of nitrogen. A solution of triflouromethanesulfonic anhydride (1.74 mL, 10.3 mmol) in dichloromethane (30 mL) was added dropwise over 40 min. The mixture was allowed to warm to RT and poured into 2M aqueous hydrochloric acid (50 mL) with vigorous stirring. The mixture was washed with saturated sodium bicarbonate. The organic layer was dried (MgSO$_4$) and evaporated in vacuo to give a red oil. Flash chromatography (silica gel, 1:4 ethyl acetate/cyclohexane) afforded the title compound as a yellow oil (1.62 g, 85%). MS(EI) m/e 278 [M+H]$^+$.

18b) 5-(2-flourophenyl)quinoline

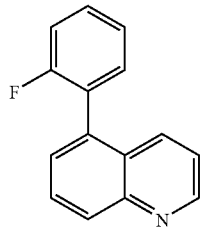

A stirred mixture of the compound of Example 18(a) (0.95 g, 3.43 mmol), 2-fluorophenylboronic acid (0.72 g, 5.14 mmol), tetrakis(triphenylphosphine)palladium(0) (0.1 g, 0.03 mmol) and potassium carbonate (1.42 g, 10.28 mmol) in 1,4-dioxane (60 mL) and water (20 mL) was refluxed for 1.5 h. The mixture was extracted with ethyl acetate. The combined extracts were dried (MgSO$_4$) and evaporated in vacuo to give a brown oil. Flash chromatography (silica gel, 1:4 ethyl acetate/cyclohexane) afforded the title compound as a pale yellow crystalline solid (0.58 g, 72%). MS(EI) m/e 224 [M+H]$^+$.

18c) 5-(2-fluorophenyl)quinoline 1-oxide

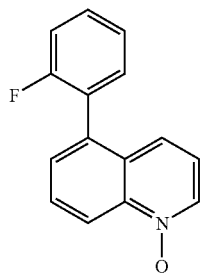

3-chloroperoxybenzoic acid (0.661 g, 3.83 mmol) was added portion-wise to a stirred solution of the compound of Example 18(b) (0.57 g, 2.55 mmol) in chloroform (6 mL) at room temperature (hereinafter "RT"). The reaction was stirred for 2 h then diluted with chloroform (100 mL), washed with saturated sodium metabisulfite, saturated sodium bicarbonate, water and saturated sodium chloride, dried (MgSO$_4$) and evaporated in vacuo to afford the title compound as a cream-coloured solid (0.475 g, 78%). MS(EI) m/e 240 [M+H]$^+$.

18d) 5-(2-fluorophenyl)-2(1H)-quinolinone

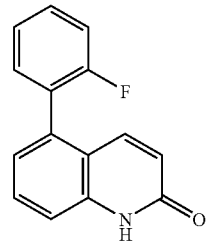

Paratoluenesulfonyl chloride (0.4 g, 2.14 mmol) and 10% aqueous potassium carbonate (20 mL) were added to a stirred solution of the compound of Example 18(c) (0.465 g, 1.94 mmol) in chloroform (10 mL). The reaction was stirred vigorously for 3 h then diluted with chloroform (100 mL). The organic layer was washed with water and saturated sodium chloride, dried (MgSO$_4$) and evaporated in vacuo. Flash chromatography (silica gel, 5% methanol/dichloromethane) afforded the title compound as a cream-coloured solid (0.349 g, 75%). MS(ES) m/e 240 [M+H]$^+$.

18e) 5-(2-fluorophenyl)-1-(4-fluorophenyl)-2(1H)-quinolinone

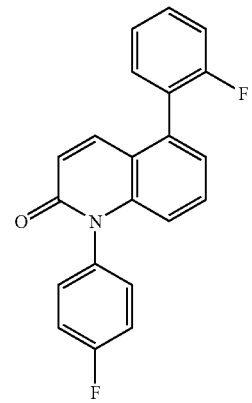

A mixture of the compound of Example 18(d) (0.1 g, 4.18 mmol), 4-fluorophenylboronic acid (0.118 g, 0.836 mmol), triethylamine (0.116 mL, 0.836 mmol), pyridine (0.068 mL, 0.836 mmol), copper (II) acetate (0.156 g, 0.836 mmol) and powdered 4 Å sieves in dichloromethane (10 mL) was stirred at RT for 7 h. Further quantities of fluorophenylboronic acid (0.06 g), copper (II) acetate (0.075 g) and powdered 4 Å sieves were added and stirring continued for 18 h. The mixture was retreated as above and stirred for a further 5 h then diluted with dichloromethane (20 mL) and filtered through a pad of celite. The filtrate was washed with saturated sodium carbonate and water, dried (Na₂SO₄) and evaporated in vacuo to give a brown solid. Flash chromatography (silica gel, 1:1 cyclohexane/ethyl acetate) afforded the title compound as a pale brown solid (0.106 g, 76%). MS(EI) m/e 334 [M+H]⁺. ¹H NMR (400 MHz, CDCl₃) δ 7.65 (d of d, J=10 and 5 Hz, 1H), 7.5-7.2 (m, 9H), 7.18 (d, J=8 Hz, 1H), 6.73 (d, J=10 Hz, 1H), 6.71 (d, J=10 Hz, 1H).

Example 19

5-(4-fluorophenyl)-1-(4-fluorophenyl)-2(1H)-quinolinone

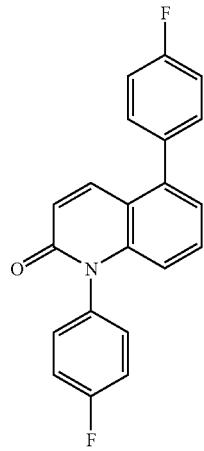

19a) 5-(4-fluorophenyl)quinoline

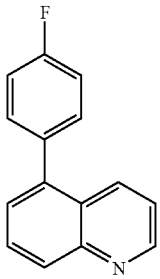

Following the procedure of Example 18(b), except substituting 4-fluorophenylboronic acid for 2-fluorophenylboronic acid, the title compound was prepared (0.78 g, 97%). MS(EI) m/e 224 [M+H]⁺.

19b) 5-(4-fluorophenyl)quinoline 1-oxide

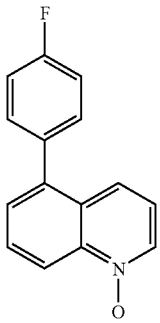

Following the procedure of Example 18(c), except substituting the compound of Example 19(a) for the compound of Example 18(b), the title compound was prepared (0.475 g, 78%). MS(EI) m/e 240 [M+H]⁺.

19c) 5-(4-fluorophenyl)-2(1H)-quinolinone

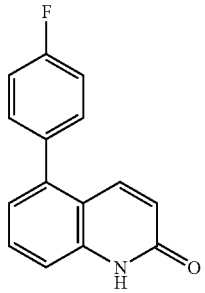

Following the procedure of Example 18(d), except substituting the compound of Example 19(b) for the compound of Example 18(c), the title compound was prepared (0.364 g, 47%). MS(EI) m/e 240 [M+H]⁺.

19d) 5-(4-fluorophenyl)-1-(4-fluorphenyl)-2(1H)-quinolinone

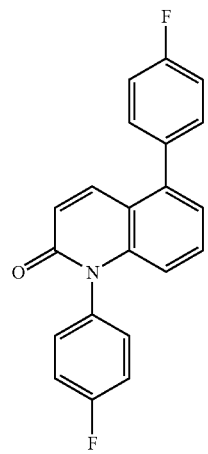

Following the procedure of Example 18(e), except substituting the compound of Example 19(c) for the compound of Example 18(d), the title compound was prepared (0.061 g, 44%). MS(EI) m/e 334 [M+H]⁺. ¹H NMR (400 MHz, CDCl₃) δ 7.82 (d of d, J=10 and 1 Hz, 1H), 7.4-6.88 (m, 10H), 6.72 (d, J=10 Hz, 1H), 6.68 (d, J=10 Hz, 1H).

Example 20

5-(2,4-difluorophenyl)-1-(4-fluorophenyl)-2(1H)-quinolinone

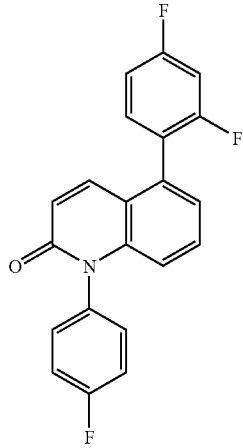

20a) 5-(2,4-difluorophenyl)quinoline

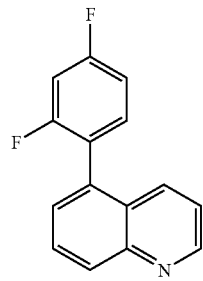

Following the procedure of Example 18(b), except substituting 2,4-difluorophenylboronic acid for 2-fluorophenylboronic acid, the title compound was prepared (0.71 g, 81%). MS(EI) m/e 242 [M+H]+.

20b) 5-(2,4-difluorophenyl)quinoline 1-oxide

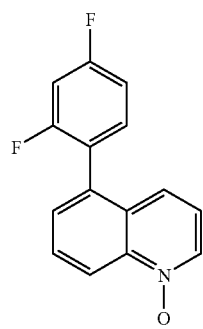

Following the procedure of Example 18(c), except substituting the compound of Example 20(a) for the compound of Example 18(b), the title compound was prepared (0.53 g, 83%). MS(EI) m/e 258 [M+H]+.

20c) 5-(2,4-difluorophenyl)-2(1H)-quinolinone

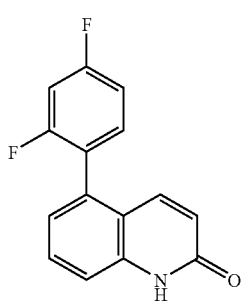

Following the procedure of Example 18(d), except substituting the compound of Example 20(b) for the compound of Example 18(c), the title compound was prepared (0.304 g, 63%). MS(EI) m/e 258 [M+H]+.

20d) 5-(2,4-difluorophenyl)-1-(4-fluorphenyl)-2(1H)-quinolinone

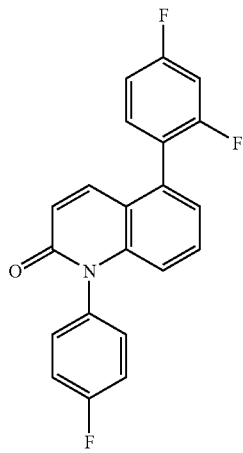

Following the procedure of Example 18(e), except substituting the compound of Example 20(c) for the compound of Example 18(d), the title compound was prepared (0.078 g, 53%). MS(EI) m/e 352 {M+H]+. 1H NMR(400 MHz, CDCl3) δ 7.6 (d of d, J=10 and 1 Hz, 1H), 7.4 (t, J=8 Hz, 1H), 7.32 (m, 6H), 7.14 (d, J=10 Hz, 1H), 2H), 6.74 (d, J=10 Hz, 1H), 6.71 (d, J=10 Hz, 1H).

Example 21

5-(4-methylphenyl)-1-(4-fluorophenyl)-2(1H)-quinolinone

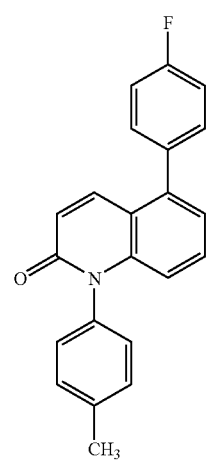

Following the procedures of Examples 18 to 20 above, the title compound was prepared.

Using the synthesis as shown in Scheme 3, the following intermediate and final compounds of Formula (I) as herein described have been made:

Example 22

7-chloro-1,5-bis(2-chlorophenyl)[1,8]naphthyridin-2(1H)-one

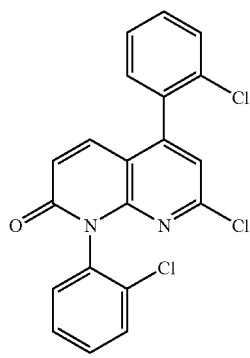

22a) 3-(Bromomethyl)-2,6-dichloro-4-(2-chlorophenyl)pyridine

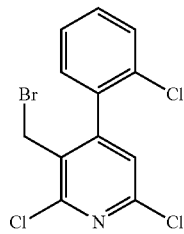

The title compound was prepared in a series of steps starting from the commercially cyanoacetamide and methyl 3-(2-chlorophenyl)-2-propynoate by known literature procedures, such as those noted in International Publication No. WO 02/058695 A1.

LC/MS Rt 3.75 min m/z 350/352/354 [MH+]

22b) tert-Butyl 3-[2,6-dichloro-4-(2-chlorophenyl)-3-pyridinyl]propanoate

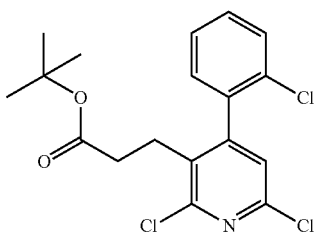

n-Butyllithium in hexanes (1.6M, 18 ml, 28.8 mmol) was added to di-isopropylamine (4.1 ml, 29.25 mmol) in dry THF (200 ml) at −10° under nitrogen. After 5 min. the solution was cooled to −70° and tert-butyl acetate (3.9 ml, 28.93 mmol) added dropwise. After stirring at −70° for 15 min. under nitrogen, 3-(bromomethyl)-2,6-dichloro-4-(2-chlorophenyl)pyridine (2.44 g, 6.942 mmol) in dry THF (18 ml) was added dropwise over 10 min., and the mixture stirred at −70° for 1 h. Glacial acetic acid (2.3 ml) was added, the temperature allowed to rise to 22° and brine (200 ml) and ethyl acetate (100 ml) added. The phases were separated and the aqueous further extracted with ethyl acetate (150 ml). The extracts were dried (Na2SO4), evaporated in vacuo and the residue purified by flash chromatography over silica eluting with cyclohexane-ethyl acetate (100:0-50:50) to give the title compound as a viscous gum (2.44 g, 91%).

LC/MS Rt 4.01 min m/z 386/388/390 [MH+]

22c) Methyl 3-[2,6-dichloro-4-(2-chlorophenyl)-3-pyridinyl]propanoate

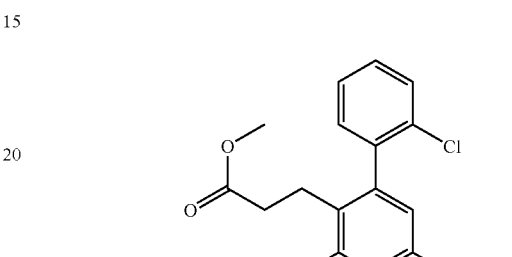

tert-Butyl 3-[2,6-dichloro-4-(2-chlorophenyl)-3-pyridinyl]propanoate (2.44 g, 6.31 mmol) was dissolved in anisole (6 ml) and trifluoroacetic acid (30 ml) added and the solution allowed to stand at 21° for 2 h, then evaporated in vacuo. The residue was dissolved in toluene (40 ml)-methanol (10 ml), and a 2M solution of trimethylsilyldiazomethane in hexanes added (8 ml), and the solution allowed to stand for 0.5 h. The solution was evaporated in vacuo, and the resulting oil purified by flash chromatography over silica eluting with cyclohexane-ethyl acetate (100:0-65:35) to give the title compound as a viscous gum (1.40 g, 64%)

LC/MS Rt 3.80 min m/z 344/346 [MH+]

22d) N-(2-chlorophenyl)-3-[2,6-dichloro-4-(2-chlorophenyl)-3-pyridinyl]propanamide

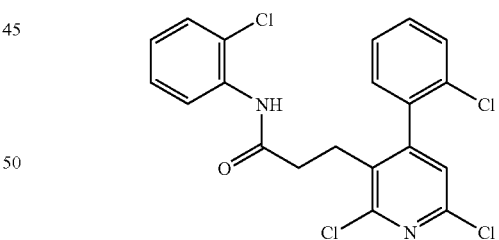

2-Chloroaniline (0.87 ml, 8.21 mmol) in dichloromethane (80 ml) was treated with 2M trimethylaluminium in toluene (4.1 ml, 8.2 mmol) at 0-5° under nitrogen. After stirring for 15 min. a solution of methyl 3-[2,6-dichloro-4-(2-chlorophenyl)-3-pyridinyl]propanoate (1.40 g, 4.063 mmol) in dichloromethane (40 ml) was added and the solution stirred at 21° for 17 h. Water (15 ml) was added (very slowly at first), followed by sufficient 2M hydrochloric acid to dissolve all the precipitated aluminium salts. The organic phase was separated and the aqueous phase further extracted with dichloromethane (50 ml). The combined organic extracts passed through a hydrophobic frit, evaporated in vacuo, and the oily residue purified by column chromatography over silica (70 g)

eluting with cyclohexane-ethyl acetate (100:0-65:35) to afford the title compound as a gum (1.52 g, 85%).

LC/MS Rt 3.84 min m/z 439/441/443 [MH+]

22e) 7-chloro-1,5-bis(2-chlorophenyl)-3,4-dihydro [1,8]naphthyridin-2(1H)-one

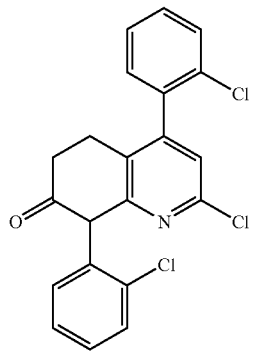

3-[6-Chloro-4-(2-chlorophenyl)-3-pyridinyl]-N-(2-chlorophenyl)propanamide (1.51 g, 3.43 mmol) was dissolved in DMF (40 ml), potassium carbonate (0.95 g, 6.87 mmol) and copper(I) iodide (1.3 g, 6.83 mmol) added and the mixture heated at reflux for 1 h. Most of the DMF was removed in vacuo, the residue was treated with water (10 ml) and brine (10 ml), and extracted with dichloromethane (2×15 ml) and ethyl acetate (15 ml). The extracts were passed through a hydrophobic frit and evaporated in vacuo to give the title compound as an off-white solid (1.6 g)

LC/MS Rt 4.01 min m/z 403/405/407 [MH+]

22f) 7-chloro-1,5-bis(2-chlorophenyl)[1,8]naphthyridin-2(1H)-one

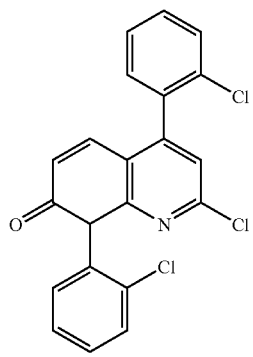

7-Chloro-1,5-bis(2-chlorophenyl)-3,4-dihydro[1,8]naphthyridin-2(1H)-one (220 mg, 0.545 mmol) in carbon tetrachloride (3 ml) was treated with NBS (110 mg; 0.618 mmol) and AlBN (1 mg) and heated under reflux for 1 h. Further NBS (110 mg, 0.618 mmol) and AlBN (2 mg) were added and heating under reflux continued for a further 2 h. DBU (0.2 ml) was added, the mixture cooled, filtered, and further carbon tetrachloride (3 ml) added, followed by 2M hydrochloric acid (3 ml). The mixture was purified by column chromatography over silica (20 g) eluting with cyclohexane-ethyl acetate (100: 0-60:40) to afford the title compound as a white solid (151 mg, 69%).

LC/MS Rt 3.75 min m/z 401/403/405 [MH+]

Example 23

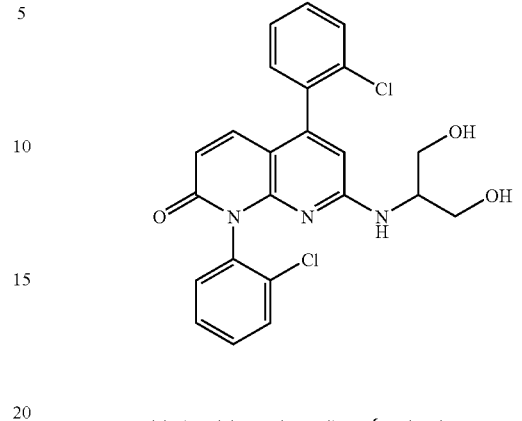

1,5-bis(2-chlorophenyl)-7-{[2-hydroxy-1-(hydroxymethyl)ethyl]amino}[1,8]naphthyridin-2(1H)-one formate 7-chloro-1,5-bis(2-chlorophenyl)[1,8]naphthyridin-2(1 h-one (73 mg, 0.182 mmol) and serinol (75 mg, 0.823 mmol) were dissolved in N-methylpyrrolidinone (2 ml) and heated in a Smith Creator microwave at 220° for 30 min. The mixture was evaporated in vacuo using a vacuum centrifuge, and the residue purified by mass directed autoprep HPLC (per general procedure B) to afford the title compound as a white solid (33 mg, 36%) NMR (400 MHz, CDCl$_3$) δ 7.65-7.55 (2H,m), 7.52-7.42 (4H,m), 7.40-7.29 (3H,m), 6.40 (1H,s), 6.35 (1H, dd), 3.55-3.42 (5H,m)

LC/MS R$_t$ 2.84 min m/z 456/458 [MH$^+$]

Example 24

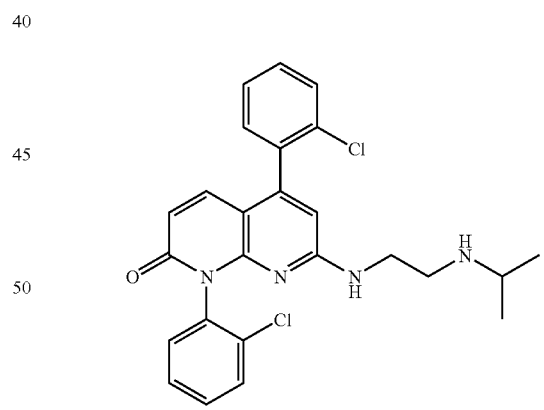

1,5-bis(2-chlorophenyl)-7-{[2-(isopropylamino) ethyl]amino}[1,8]naphthyridin-2(1H)-one formate 7-chloro-1,5-bis(2-chlorophenyl)[1,8]naphthyridin-2 (1H)-one (73 mg, 0.182 mmol) and N-isopropylethylenediamine (0.14 ml, 1.122 mmol) were dissolved in N-methylpyrrolidinone (2 ml) and heated in a Smith Creator microwave at 220° for 30 min. The solution was passed down an SCX-2 cartridge (10 g) and eluted with methanol, followed by 2M ammonia in methanol. The latter eluate was evaporated in vacuo and the residue purified by mass directed autoprep HPLC (per General procedure B) to afford the title compound as a clear gum (24 mg, 26%)

NMR (400 MHz, CDCl$_3$) δ 7.58-7.48 (2H,m), 7.45-7.22 (7H,m), 6.43 (1H,d), 6.28,6.25 (1H,2×s), 3.37-3.19 (2H,m), 3.12 (1H,m), 2.83-2.58 (2H,m), 1.20 (6H,d)

LC/MS R$_t$ 2.49 min m/z 467/469 [MH$^+$]

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

n is 0 or an integer having a value of 1 to 10;
m is 0 or an integer having a value of 1 or 2;
q is 0 or an integer having a value of 1 to 10;
R$_2$ is independently selected from a hydrogen, C$_{1-10}$ alkyl, aryl, arylC$_{1-10}$ alkyl, heteroaryl, or heteroarylC$_{1-10}$ alkyl moiety, which moieties, excluding hydrogen, are all optionally substituted; or R$_2$ is the moiety X$_1$(CR$_{10}$R$_{20}$)$_q$C(A$_1$)(A$_2$)(A$_3$), or C(A$_1$)(A$_2$)(A$_3$);
X$_1$ is N(R$_{10}$), O, S(O)$_m$, or CR$_{10}$R$_{20}$;
X$_2$ is independently hydrogen, halogen or C$_{1-4}$ alkyl;
A$_1$ is an optionally substituted C$_{1-10}$ alkyl;
A$_2$ is an optionally substituted C$_{1-10}$ alkyl;
A$_3$ is hydrogen or is an optionally substituted C$_{1-10}$ alkyl;
G$_1$ is C—X$_2$;
R$_3$ is C$_{1-10}$ alkyl, C$_{3-7}$ cycloalkyl, C$_{3-7}$ cycloalkylC$_{1-4}$alkyl, aryl, arylC$_{1-10}$ alkyl, heteroaryl, heteroarylC$_{1-10}$ alkyl, heterocyclic, or a heterocyclylC$_{1-10}$ alkyl moiety, which moieties are optionally substituted;
R$_4$ and R$_{14}$ are each independently selected from hydrogen, optionally substituted C$_{1-4}$ alkyl, optionally substituted aryl, or optionally substituted aryl-C$_{1-4}$ alkyl, arylC$_{1-10}$ alkyl, heteroaryl or heteroarylC$_{1-10}$ alkyl, wherein each of these moieties may be optionally substituted;

What is claimed is:

1. A compound of the formula:

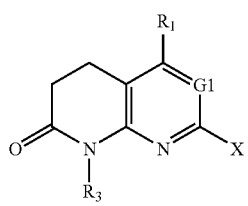

(II)

wherein
R$_1$ is an optionally substituted aryl or an optionally substituted heteroaryl ring;
X is R$_2$, OR$_2$, S(O)$_m$R$_2$, (CH$_2$)$_n$N(R$_{10}$)S(O)$_m$R$_2$, (CH$_2$)$_n$N(R$_{10}$)C(O)R$_2$, (CH$_2$)$_n$NR$_4$R$_{14}$, NR$_2$(CH$_2$)$_n$NR$_4$R$_{14}$, O(CH$_2$)$_n$NR$_4$R$_{14}$, S(CH$_2$)$_n$NR$_4$R$_{14}$, (CH$_2$)$_n$J, NR$_2$(CH$_2$)$_n$J, O(CH$_2$)$_n$J, S(CH$_2$)$_n$J, or (CH$_2$)$_n$N(R$_2$)$_2$;
J is an optionally substituted heteroaryl ring;
R$_{10}$ and R$_{20}$ are independently selected from hydrogen or C$_{1-4}$alkyl; or
a pharmaceutically acceptable salt thereof.

2. The compound according to claim 1 wherein R$_1$ is an optionally substituted phenyl or naphthyl.

3. The compound according to claim 2 wherein the phenyl is substituted one or more times independently by halogen, alkyl, hydroxy, alkoxy, amino, or halosubstituted alkyl.

4. The compound according to claim 3 wherein the substituents are independently chlorine, fluorine, C$_{1-4}$ alkyl, or CF$_3$.

5. The compound according to claim 3 wherein the phenyl ring is substituted in the 2, 4, or 6-position, di-substituted in the 2,4-position, or tri-substituted in the 2,4,6-position.

6. The compound according to claim 1 wherein X is OR$_2$, or S(O)$_m$R$_2$.

7. The compound according to claim 1 wherein X is (CH$_2$)$_n$NR$_4$R$_{14}$, or (CH$_2$)$_n$N(R$_2$)$_2$.

8. The compound according to claim 1 wherein X is R$_2$ or (CH$_2$)$_n$N(R$_{10}$)S(O)$_m$R$_2$, or (CH$_2$)$_n$N(R$_{10}$)C(O)R$_2$.

9. The compound according to claim 1 wherein R$_2$, other than hydrogen, is optionally substituted independently one or more times with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$cycloalkenyl$C_{1-10}$ alkyl, halogen, —C(O), cyano, nitro, $(CR_{10}R_{20})_nOR_6$, $(CR_{10}R_{20})_nSH$, $(CR_{10}R_{20})_nS(O)_mR_7$, $(CR_{10}R_{20})_nNR_{10}S(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nC(=NOR_6)NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$;

and wherein
- $R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or a heteroaryl$C_{1-10}$ alkyl moiety, and wherein these moieties, excluding hydrogen, are optionally substituted;
- $R_7$ is $C_{1-6}$alkyl, aryl, aryl$C_{1-6}$alkyl, heterocyclic, heterocyclyl$C_{1-6}$ alkyl, heteroaryl, or a heteroaryl$C_{1-6}$alkyl moiety; and wherein each of these moieties are optionally substituted; and
- Z is oxygen or sulfur.

10. The compound according to claim 6 wherein $R_2$ is an optionally substituted $C_{1-10}$alkyl.

11. The compound according to claim 10 wherein the alkyl is substituted by $(CR_{10}R_{20})_nC(Z)OR_6$, $(CR_{10}R_{20})_nOR_6$, or $(CR_{10}R_{20})_nNR_4R_{14}$ and $R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or a heteroaryl$C_{1-10}$ alkyl moiety, and wherein the $R_6$ moieties, excluding hydrogen, are optionally substituted.

12. The compound according to claim 1 wherein $R_2$ is the $X_1(CR_{10}R_{20})_qC(A_1)(A_2)(A_3)$, or $C(A_1)(A_2)(A_3)$.

13. The compound according to claim 12 wherein $X_1$ is oxygen or $N(R_{10})$.

14. The compound according to claim 12 wherein at least one of $A_1$, $A_2$ or $A_3$ is substituted by $(CR_{10}R_{20})_nOR_6$ and $R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or a heteroaryl$C_{1-10}$alkyl moiety, and wherein the $R_6$ moieties, excluding hydrogen, are optionally substituted.

15. The compound according to claim 14, wherein q is 0, 1 or 2.

16. The compound according to claim 1 wherein $R_3$ is an optionally substituted $C_{1-10}$ alkyl, $C_{3-7}$ cycloalkyl, $C_{3-7}$cycloalkyl$C_{1-4}$alkyl, aryl, aryl$C_{1-10}$ alkyl.

17. The compound according to claim 16 wherein $R_3$ is optionally substituted one or more times independently with $C_{1-10}$ alkyl, halo-substituted $C_{1-10}$ alkyl, $C_{2-10}$ alkenyl, $C_{2-10}$alkynyl, $C_{3-7}$cycloalkyl, $C_{3-7}$cycloalkyl$C_{1-10}$ alkyl, $C_{5-7}$cycloalkenyl, $C_{5-7}$cycloalkenyl$C_{1-10}$ alkyl, halogen, cyano, nitro, $(CR_{10}R_{20})_nOR_6$, $(CR_{10}R_{20})_nSH$, $(CR_{10}R_{20})_nS(O)_mR_7$, $(CR_{10}R_{20})_nNR_{10}S(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$;

and wherein
- $R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or a heteroaryl$C_{1-10}$ alkyl moiety, and wherein these moieties, excluding hydrogen, are optionally substituted;
- $R_7$ is $C_{1-6}$alkyl, aryl, aryl$C_{1-6}$alkyl, heterocyclic, heterocyclyl$C_{1-6}$ alkyl, heteroaryl, or a heteroaryl$C_{1-6}$alkyl moiety; and wherein each of these moieties are optionally substituted.

18. The compound according to claim 17 wherein the optional substituent is halogen, $C_{1-10}$ alkyl, hydroxy, alkoxy, amino, or halosubstituted $C_{1-10}$ alkyl.

19. The compound according to claim 1 wherein $X_2$ is hydrogen.

20. The compound according to claim 1, which is:
- 1,5-bis(4-fluorophenyl)[1,8]naphthyridin-2(1H)-one;
- 5-(2,4-difluorophenyl)-1-(4-fluorophenyl)[1,8]naphthyridin-2(1H)-one;
- 1,5-bis(2-chlorophenyl)-7-{[2-(isopropylamino)ethyl]amino}[1,8]naphthyridin-2(1H)-one;
- 1,5-bis(2-chlorophenyl)-7-{[2-hydroxy-1-(hydroxymethyl)ethyl]amino}[1,8]-naphthyridin-2(1H)-one;

or a pharmaceutically acceptable salt thereof.

21. A pharmaceutical composition comprising an effective amount of a compound according to claim 1 and a pharmaceutically acceptable carrier or diluent.

* * * * *